United States Patent [19]

Hartung et al.

[11] 3,983,173

[45] Sept. 28, 1976

[54] 2-CARBOXAMIDO-SUBSTITUTED TETRACYCLINES AND PROCESS FOR THEIR MANUFACTURE

[75] Inventors: Herbert Hartung, Kriftel, Taunus; Walter Durckheimer, Hattersheim am Main; Elmar Schrinner, Wiesbaden; Hermann Gerhards, Hofheim, Taunus, all of Germany

[73] Assignee: Hoechst Aktiengesellschaft, Frankfurt am Main, Germany

[22] Filed: Oct. 31, 1974

[21] Appl. No.: 519,843

[30] Foreign Application Priority Data

Nov. 3, 1973 Germany............................ 2355118

[52] U.S. Cl.................... 260/559 AT; 260/247.2 B; 260/268 PT; 260/293.76; 260/326.8; 424/227
[51] Int. Cl.².................................. C07C 103/19
[58] Field of Search.............. 260/559 AT, 247.2 B, 260/268 PT, 293.76, 326.8; 424/227

[56] References Cited

UNITED STATES PATENTS 3,456,007  7/1969  Rondelet...................... 260/559 AT

*Primary Examiner*—C. Davis
*Attorney, Agent, or Firm*—Curtis, Morris & Safford

[57] ABSTRACT

2-Carboxamido-substituted tetracyclines of the general formula

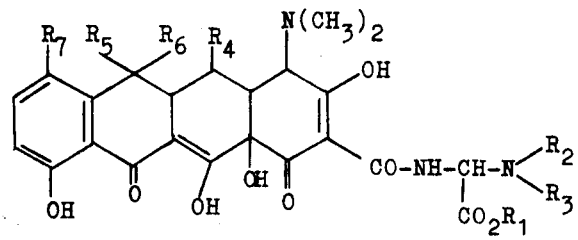

a process for their preparation and compositions containing these compounds.

25 Claims, No Drawings

2-CARBOXAMIDO-SUBSTITUTED TETRACYCLINES AND PROCESS FOR THEIR MANUFACTURE

The present invention relates to 2-carboxamido-substituted tetracyclines of the general formula

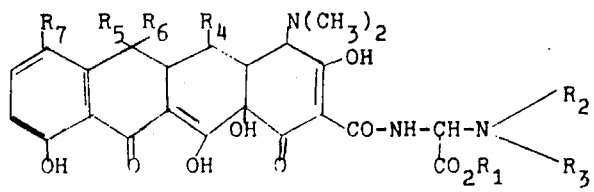

in which $R_1$ stands for a lower, optionally branched alkyl group, $R_2$ and $R_3$ may be identical or different and each stands for hydrogen, an optionally branched alkyl group of 1 to 6, preferably 1 to 4 carbon atoms, which may carry one or more identical or different groups, such as a hydroxy group, a lower dialkylamino group, a lower dialkylcarbamoyl group, a lower alkoxycarbonyl group, a phenyl group, a heterocyclic group, especially a 5- or 6-membered ring which may include oxygen and/or nitrogen, and a carboxyl group, in this latter case the alkyl moiety may also be substituted by an amino group, or a cycloalkyl group of 5 to 7 carbon atoms, and in which $R_2$ and $R_3$ may also be closed to form a saturated or unsaturated, 5- or 6-membered ring which may include a nitrogen or oxygen atom and which may carry one or more lower alkyl groups, lower hydroxyalkyl groups, lower carboxyalkyl groups, hydroxyl or carboxyl groups, $R_4$ and $R_5$ may be identical or different and each stands for hydrogen or a hydroxy group, $R_6$ stands for hydrogen or the methyl group, $R_5$ and $R_6$ together may also stand for a methylene group, and $R_7$ stands for a hydrogen, chlorine or bromine atom or for the dimethylamino or diethylamino group, as well as to the physiologically acceptable salts thereof.

By lower groups, there are to be understood those containing 1 to 4 carbon atoms in the alkyl moiety.

This invention further relates to a process for the manufacture of the said compounds, which comprises reacting a tetracycline of the formula II

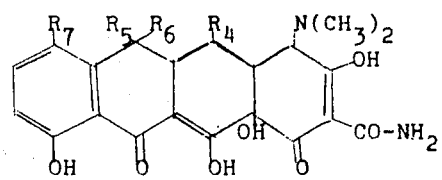

in which $R_4$ to $R_7$ are defined as above, with a glyoxylic acid ester of the formula III

or with a semi-acetal thereof corresponding to the formula IV

in which $R_1$ are defined as above, and $R_8$ stands for a lower alkyl group, preferably the ethyl group, and with an amine of the formula V

in which $R_2$ and $R_3$ are defined as above.

As compounds of formula II, there may be used any tetracyclines having an unsubstituted 2-carboxamido group, which can be prepared by fermentation or by partial synthesis, for example tetracycline, oxytetracycline, 7-chlorotetracycline, 7-bromotetracycline, 7-chloro-6-desmethyl-tetracycline, 6-desmethyl-tetracycline, 6-desoxy-5-oxytetracycline, 7-dimethylamino-6-desmethyl-6-desoxytetracycline, 7-diethylamino-6-desmethyl-6-desoxy-tetracycline, 6-methylene-6-desmethyl-6-desoxy-oxytetracycline; preferably tetracycline, oxytetracycline, chlorotetracycline, 6-desoxy-5-oxytetracycline and 7-chloro-6-desmethyl-tetracycline.

As amine components of formula V to be used according to the invention, there are mentioned, in addition to ammonia, for example, the following primary or secondary aliphatic or heterocyclic amines: methylamine, ethylamine, n-propylamine, i-propylamine, n-butylamine, i-butylamine, pentylamine, hexylamine, dimethylamine, diethylamine, di-n-butylamine, di-i-butylamine, di-i-hexylamine; cyclopentylamine, cyclohexylamine, cycloheptylamine, diethylamino-ethylamine, bis-(diethylaminoethyl)-amine, ethanolamine, diethanol-amine, methyl-hydroxyethylamine, benzylamine, dibenzylamine, β-phenyl-ethylamine, β-phenyl-propylamine, 2-morpholino-ethylamine, 2-morpholino-propylamine, 2-piperidino-propylamine, 4-morpholino-butylamine, 2-pyrrolidino-ethylamine, dimethylcarbamoyl-ethylamine, glycine ethyl ester, glycine, alanine, leucine, threonine, valine, phenylalanine, aspartic acid, glutamic acid, lysine, ornithine, histidine, proline, hydroxyproline, piperidine, pyrrolidine, piperazine, morpholine, α-methyl-pyrrolidine, α,β- or α,α-dimethyl-pyrrolidine, β-n-propyl-pyrrolidine, N-methyl-piperazine, N-(β-hydroxyethyl)-piperazine and 4carboxy-ethyl-piperidine.

Among the primary and secondary amines of formula V, which have been disclosed hereinbefore by some typical examples, the secondary amines in which $R_2$ and $R_3$ stand for alkyl of 1 to 4 carbon atoms, which may optionally be substituted by lower alkoxy-carbonyl, carboxyl and, optionally at the same time as carboxyl, also by an amino group, or in which $R_2$ and $R_3$ may optionally be closed to form a 5- or 6-membered ring which may include oxygen or nitrogen and may be substituted, in particular, by lower alkyl or lower hydroxyalkyl, are preferably used according to the invention.

As examples of the glyoxylic acid esters of formula III, there may be mentioned the methyl ester, ethyl ester, propyl ester, i-propyl ester, i-butyl ester, or n-butyl ester, especially the methyl ester, ethyl ester and n-butyl ester, as well as their semiacetals of formula IV, for example the methyl-acetal, propyl-acetal or butyl acetal, especially the methyl semi-acetal, ethyl semiacetal and n-butyl semiacetal.

The starting products of formula II and V are products well known in the art, those of formula III can be obtained in simple manner for example according to "Organic Synthesis Coll." Vol. IV, page 124 (1963). The starting compounds of formula IV can be prepared, for example according to Organikum, 6th edition 1967, page 352.

The reaction of the invention is carried out, for example by dissolving or suspending a compound of formula II in a suitable solvent, for example chloroform, dimethylformamide, methylene chloride, formamide, glycol dimethyl ether, dioxan, tetrahydrofuran, acetone, tetramethyl urea or N-methylpyrrolidone, and reacting this solution or suspension at temperatures of about 0° to 100°C, preferably about 20° to 50°C, with stoichiometric amounts or an excess amount of a glyoxylic acid derivative of formula III or IV and stoichiometric amounts or an excess amount of an amine of formula V. If excess amounts of compounds of formula III or IV or V are used, this excess may vary greatly, for example between 1 and 10 mols.

The compounds of formula III or IV or V may be added directly or in solution. It does not matter in which succession the reaction components are mixed together, but it is advantageous first to mix the amine component of formula V with the glyoxylic acid derivative and then to add the tetracycline component of formula II.

After having been mixed for several hours, where required under an inert gas, the reaction mixture may be concentrated by evaporation in vacuo at temperatures of about 20° to 50°C, and the remaining crude product may be dissolved preferably in a polar aprotic solvent, for example ethyl acetate, butyl acetate, dichloromethane, chloroform, dioxan or tetrahydrofuran. Precipitation with a less polar aprotic solvent, for example diethyl ether, diisopropyl ether, di-n-butyl ether, benzene, toluene, petrol ether or cyclohexane yields the reaction product in a solid pure form.

As physiologically acceptable salt-forming agents of the products of formula I, there are mentioned, for example, mineral acids, such as hydrochloric acid, sulfuric acid, nitric acid, phosphoric acid or boric acid; and organic acids, such as acetic acid, lactic acid, citric acid, maleic acid, succinic acid, malic acid and tartaric acid. The organic salt-forming agents may themselves have pharmaceutical activity, for example penicillins, especially penicillins G and V, as well as carbenicillin, cephalosporins, pantothenoic acid, chloramphenicol semisuccinate, salilylic acid, ascorbic acid and nalidixinic acid. The salts may be prepared, for example by mixing stoichiometric amounts of the components in a polar solvent, for example water, alcohol or dimethylformamide, whereupon the salt either precipitates or can be isolated by evaporation, lyophilization or precipitation.

2-Carboxamido-substituted tetracycline derivatives have successfully been employed for many years in the treatment of bacterial infections. In contradistinction to the compounds from which they are derived, they can also be administered in simple manner by the parenteral route. This route ensures a rapid and high concentration of the active substances in the blood, which is important especially in critical cases.

The compounds of formula I are valuable chemotherapeutic substances which have the same antibacterial activity spectrum as the starting antibiotics of formula II, they have no influence on the cardiovascular system, when administered parenterally, for example no suppression of the blood pressure nor of the cardiac frequency, and they are, however, very well absorbed when administered orally.

Another advantage of the compounds of the invention is their good stability in the dissolved state.

The individual dosage unit in which the compounds of formula I are to be administered depends on the nature and degree of the infection and may vary from about 2 to 20 mg/kg, preferably from about 3 to 10 mg/kg of body weight.

As pharmaceutical preparations, there are mentioned, for example tablets, dragees or capsules, which may contain, in addition to the products of the invention, the usual carriers and adjuvants, for example talc, starch, lactose or magnesium stearate. The active substances may also be administered as solutions, for example in water or in aqueous buffer solutions at pH-values of from 4 to 9, these solutions having to be prepared prior to their administration. It is also possible to combine the products of the invention with other chemotherapeutic substances, for example those having antibacterial activity, such as penicillins, chloroamphenicol, gentamycin or sulfonamides.

As examples of compounds of formula I to be prepared according to the invention, there may especially be mentioned the derivatives of the tetracyclines mentioned in Table I, oxytetracyclines mentioned in Table II, chlorotetracyclines mentioned in Table III, 6-desoxy-oxytetracyclines mentioned in Table IV and 6-desmethyl-7-chloro-tetracyclines mentioned in Table V; those parts of the tables marked with A contain particularly preferable compounds of the invention.

For the purpose of a better survey, the following Tables only contain the substituents $R_1$ to $R_7$ instead of naming each individual compound. These substituents seen together with the general formula I

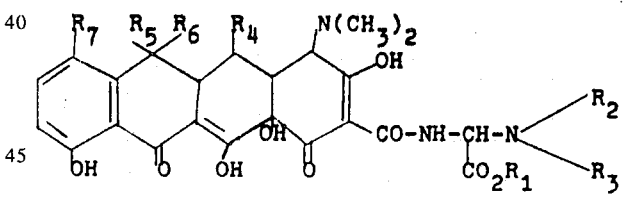

(I)

immediately reveal the constitution of the individual compounds.

TABLE IA

| $R_1$ | $R_2$ | $R_3$ | $R_4$ | $R_5$ | $R_6$ | $R_7$ |
|---|---|---|---|---|---|---|
| $CH_3$ | $CH_3$ | $CH_3$ | H | OH | $CH_3$ | H |
| $CH_3$ | $CH_3$ | $C_2H_5$ | H | OH | $CH_3$ | H |
| $CH_3$ | $C_2H_5$ | $C_2H_5$ | H | OH | $CH_3$ | H |
| $CH_3$ | $n\text{-}C_3H_7$ | $n\text{-}C_3H_7$ | H | OH | $CH_3$ | H |
| $CH_3$ | $n\text{-}C_4H_9$ | $n\text{-}C_4H_9$ | H | OH | $CH_3$ | H |
| $CH_3$ | H | $CH_2\text{—}COOH$ | H | OH | $CH_3$ | H |
| $CH_3$ | H | $CH_2\text{—}COOC_2H_5$ | H | OH | $CH_3$ | H |
| $CH_3$ | H | $CH_3\text{—}CH\text{—}COOH$ | H | OH | $CH_3$ | H |
| $CH_3$ | H | $CH_3\text{—}CH\text{—}COOC_2H_5$ | H | OH | $CH_3$ | H |
| $CH_3$ | H | $-CH_2\text{—}CH_2\text{—}COOH$ | H | OH | $CH_3$ | H |
| $CH_3$ | H | $-CH_2\text{—}CH_2\text{—}COOC_2H_5$ | H | OH | $CH_3$ | H |
| $CH_3$ | H | $-(CH_2)_4\text{—}CH\text{—}COOH$ $\;\;\;\;\;\;\;\;\;\;\;\;\;\;\;\;\;\;\;\;\;\;\;\;\;\;\;\;\;NH_2$ | H | OH | $CH_3$ | H |
| $CH_3$ | ⌐⌐ | | H | OH | $CH_3$ | H |

TABLE IA-continued

| R₁ | R₂ | R₃ | R₄ | R₅ | R₆ | R₇ |
|---|---|---|---|---|---|---|
| $CH_3$ | | cyclohexyl | H | OH | $CH_3$ | H |
| $CH_3$ | | tetrahydropyranyl (O) | H | OH | $CH_3$ | H |
| $CH_3$ | | piperidinyl (NH) | H | OH | $CH_3$ | H |
| $CH_3$ | | N-methylpiperidinyl | H | OH | $CH_3$ | H |
| $CH_3$ | | N-ethylpiperidinyl | H | OH | $CH_3$ | H |
| $CH_3$ | | N-(2-hydroxyethyl)piperidinyl | H | OH | $CH_3$ | H |
| $C_2H_5$ | $CH_3$ | $CH_3$ | H | OH | $CH_3$ | H |
| $C_2H_5$ | $CH_3$ | $C_2H_5$ | H | OH | $CH_3$ | H |
| $C_2H_5$ | $C_2H_5$ | $C_2H_5$ | H | OH | $CH_3$ | H |
| $C_2H_5$ | $n\text{-}C_3H_7$ | $n\text{-}C_3H_7$ | H | OH | $CH_3$ | H |
| $C_2H_5$ | $n\text{-}C_4H_9$ | $n\text{-}C_4H_9$ | H | OH | $CH_3$ | H |
| $C_2H_5$ | H | $CH_2\text{—COOH}$ | H | OH | $CH_3$ | H |
| $C_2H_5$ | H | $CH_2\text{—COOC}_2H_5$ | H | OH | $CH_3$ | H |
| $C_2H_5$ | H | $CH_3\text{—CH—COOH}$ | H | OH | $CH_3$ | H |
| $C_2H_5$ | H | $CH_3\text{—CH—COOC}_2H_5$ | H | OH | $CH_3$ | H |
| $C_2H_5$ | H | $\text{—}CH_2\text{—}CH_2\text{—COOH}$ | H | OH | $CH_3$ | H |
| $C_2H_5$ | H | $\text{—}CH_2\text{—}CH_2\text{—COOC}_2H_5$ | H | OH | $CH_3$ | H |
| $C_2H_5$ | H | $\text{—}(CH_2)_4\text{—CH—COOH}$ (with $NH_2$) | H | OH | $CH_3$ | H |
| $C_2H_5$ | | cyclopentyl | H | OH | $CH_3$ | H |
| $C_2H_5$ | | cyclohexyl | H | OH | $CH_3$ | H |
| $C_2H_5$ | | tetrahydropyranyl (O) | H | OH | $CH_3$ | H |
| $C_2H_5$ | | piperidinyl (NH) | H | OH | $CH_3$ | H |
| $C_2H_5$ | | N-methylpiperidinyl | H | OH | $CH_3$ | H |
| $C_2H_5$ | | N-ethylpiperidinyl | H | OH | $CH_3$ | H |
| $C_2H_5$ | | N-(2-hydroxyethyl)piperidinyl | H | OH | $CH_3$ | H |
| $n\text{-}C_3H_7$ | $CH_3$ | $CH_3$ | H | OH | $CH_3$ | H |
| $n\text{-}C_3H_7$ | $CH_3$ | $C_2H_5$ | H | OH | $CH_3$ | H |
| $n\text{-}C_3H_7$ | $C_2H_5$ | $C_2H_5$ | H | OH | $CH_3$ | H |
| $n\text{-}C_3H_7$ | $n\text{-}C_3H_7$ | $n\text{-}C_3H_7$ | H | OH | $CH_3$ | H |
| $n\text{-}C_3H_7$ | $n\text{-}C_4H_9$ | $n\text{-}C_4H_9$ | H | OH | $CH_3$ | H |
| $n\text{-}C_3H_7$ | H | $CH_2\text{—COOH}$ | H | OH | $CH_3$ | H |
| $n\text{-}C_3H_7$ | H | $CH_2\text{—COOC}_2H_5$ | H | OH | $CH_3$ | H |
| $n\text{-}C_3H_7$ | H | $CH_3\text{—CH—COOH}$ | H | OH | $CH_3$ | H |
| $n\text{-}C_3H_7$ | H | $CH_3\text{—CH—COOC}_2H_5$ | H | OH | $CH_3$ | H |
| $n\text{-}C_3H_7$ | H | $\text{—}CH_2\text{—}CH_2\text{—COOH}$ | H | OH | $CH_3$ | H |
| $n\text{-}C_3H_7$ | H | $\text{—}CH_2\text{—}CH_2\text{—COOC}_2H_5$ | H | OH | $CH_3$ | H |
| $n\text{-}C_3H_7$ | H | $\text{—}(CH_2)_4\text{—CH—COOH}$ (with $NH_2$) | H | OH | $CH_3$ | H |
| $n\text{-}C_3H_7$ | | cyclopentyl | H | OH | $CH_3$ | H |
| $n\text{-}C_3H_7$ | | cyclohexyl | H | OH | $CH_3$ | H |
| $n\text{-}C_3H_7$ | | tetrahydropyranyl (O) | H | OH | $CH_3$ | H |
| $n\text{-}C_3H_7$ | | piperidinyl (NH) | H | OH | $CH_3$ | H |
| $n\text{-}C_3H_7$ | | N-methylpiperidinyl | H | OH | $CH_3$ | H |
| $n\text{-}C_3H_7$ | | N-ethylpiperidinyl | H | OH | $CH_3$ | H |
| $n\text{-}C_3H_7$ | | N-(2-hydroxyethyl)piperidinyl | H | OH | $CH_3$ | H |
| $n\text{-}C_4H_9$ | $CH_3$ | $CH_3$ | H | OH | $CH_3$ | H |
| $n\text{-}C_4H_9$ | $CH_3$ | $C_2H_5$ | H | OH | $CH_3$ | H |
| $n\text{-}C_4H_9$ | $C_2H_5$ | $C_2H_5$ | H | OH | $CH_3$ | H |
| $n\text{-}C_4H_9$ | $n\text{-}C_3H_7$ | $n\text{-}C_3H_7$ | H | OH | $CH_3$ | H |
| $n\text{-}C_4H_9$ | $n\text{-}C_4H_9$ | $n\text{-}C_4H_9$ | H | OH | $CH_3$ | H |
| $n\text{-}C_4H_9$ | H | $CH_2\text{—COOH}$ | H | OH | $CH_3$ | H |
| $n\text{-}C_4H_9$ | H | $CH_2\text{—COOC}_2H_5$ | H | OH | $CH_3$ | H |
| $n\text{-}C_4H_9$ | H | $CH_3\text{—CH—COOH}$ | H | OH | $CH_3$ | H |
| $n\text{-}C_4H_9$ | H | $CH_3\text{—CH—COOC}_2H_5$ | H | OH | $CH_3$ | H |
| $n\text{-}C_4H_9$ | H | $\text{—}CH_2\text{—}CH_2\text{—COOH}$ | H | OH | $CH_3$ | H |
| $n\text{-}C_4H_9$ | H | $\text{—}CH_2\text{—}CH_2\text{—COOC}_2H_5$ | H | OH | $CH_3$ | H |
| $n\text{-}C_4H_9$ | H | $\text{—}(CH_2)_4\text{—CH—COOH}$ (with $NH_2$) | H | OH | $CH_3$ | H |
| $n\text{-}C_4H_9$ | | cyclopentyl | H | OH | $CH_3$ | H |
| $n\text{-}C_4H_9$ | | cyclohexyl | H | OH | $CH_3$ | H |
| $n\text{-}C_4H_9$ | | tetrahydropyranyl (O) | H | OH | $CH_3$ | H |
| $n\text{-}C_4H_9$ | | piperidinyl (NH) | H | OH | $CH_3$ | H |
| $n\text{-}C_4H_9$ | | N-methylpiperidinyl | H | OH | $CH_3$ | H |
| $n\text{-}C_4H_9$ | | N-ethylpiperidinyl | H | OH | $CH_3$ | H |
| $n\text{-}C_4H_9$ | | N-(2-hydroxyethyl)piperidinyl | H | OH | $CH_3$ | H |

TABLE IB

| $R_1$ | $R_2$ | $R_3$ | $R_4$ | $R_5$ | $R_6$ | $R_7$ |
|---|---|---|---|---|---|---|
| $CH_3$ | H | H | H | OH | $CH_3$ | H |
| $CH_3$ | H | $CH_3$ | H | OH | $CH_3$ | H |
| $CH_3$ | H | $C_2H_5$ | H | OH | $CH_3$ | H |
| $CH_3$ | H | $n\text{-}C_3H_7$ | H | OH | $CH_3$ | H |
| $CH_3$ | H | $n\text{-}C_4H_9$ | H | OH | $CH_3$ | H |
| $CH_3$ | H | $i\text{-}C_3H_7$ | H | OH | $CH_3$ | H |
| $CH_3$ | H | $i\text{-}C_4H_9$ | H | OH | $CH_3$ | H |
| $CH_3$ | H | $n\text{-}C_5H_{11}$ | H | OH | $CH_3$ | H |
| $CH_3$ | H | $n\text{-}C_6H_{13}$ | H | OH | $CH_3$ | H |
| $CH_3$ | H | $C_2H_4OH$ | H | OH | $CH_3$ | H |
| $CH_3$ | H | $-CH_2-CH(OH)-CH_3$ | H | OH | $CH_3$ | H |
| $CH_3$ | H | $-CH_2-CH_2-CH_2OH$ | H | OH | $CH_3$ | H |
| $CH_3$ | H | $-CH_2-CH_2-N(CH_3)_2$ | H | OH | $CH_3$ | H |
| $CH_3$ | H | $-CH_2-CH_2-N(C_2H_5)_2$ | H | OH | $CH_3$ | H |
| $CH_3$ | H | $-CH_2-CH_2-N(C_4H_9)_2$ | H | OH | $CH_3$ | H |
| $CH_3$ | H | $-CH_2-CH_2-CH_2-N(CH_3)_2$ | H | OH | $CH_3$ | H |
| $CH_3$ | H | $-CH_2-CH_2-CH_2-N(C_2H_5)_2$ | H | OH | $CH_3$ | H |
| $CH_3$ | H | $-CH_2CON(CH_3)_2$ | H | OH | $CH_3$ | H |
| $CH_3$ | H | $-CH_2-CH_2-CON(CH_3)_2$ | H | OH | $CH_3$ | H |
| $CH_3$ | H | $-CH_2-CON(C_2H_5)_2$ | H | OH | $CH_3$ | H |
| $CH_3$ | H | $-CH_2-C_6H_5$ | H | OH | $CH_3$ | H |
| $CH_3$ | H | $-CH_2-CH_2-C_6H_5$ | H | OH | $CH_3$ | H |
| $CH_3$ | H | $-CH_2-CH_2-\text{pyrrolidinyl}$ | H | OH | $CH_3$ | H |
| $CH_3$ | H | $-CH_2-CH_2-\text{morpholinyl}$ | H | OH | $CH_3$ | H |
| $CH_3$ | H | $-CH_2-CH_2-\text{piperidinyl}$ | H | OH | $CH_3$ | H |
| $CH_3$ | H | $-CH_2-CH_2-\text{(4-methylpiperazinyl)}$ | H | OH | $CH_3$ | H |
| $CH_3$ | $n\text{-}C_5H_{11}$ | $n\text{-}C_5H_{11}$ | H | OH | $CH_3$ | H |
| $CH_3$ | $n\text{-}C_6H_{13}$ | $n\text{-}C_6H_{13}$ | H | OH | $CH_3$ | H |
| $CH_3$ | $i\text{-}C_3H_7$ | $i\text{-}C_3H_7$ | H | OH | $CH_3$ | H |
| $CH_3$ | $i\text{-}C_4H_9$ | $i\text{-}C_4H_9$ | H | OH | $CH_3$ | H |
| $CH_3$ | $C_2H_4OH$ | $C_2H_4OH$ | H | OH | $CH_3$ | H |
| $CH_3$ | $-CH_2-CH(OH)-CH_3$ | $-CH_2-CH(OH)-CH_3$ | H | OH | $CH_3$ | H |
| $CH_3$ | $-CH_3$ | $C_2H_4OH$ | H | OH | $CH_3$ | H |
| $CH_3$ | $-CH_2-CH_2-CH_2OH$ | $-CH_2-CH_2-CH_2OH$ | H | OH | $CH_3$ | H |
| $CH_3$ | $-CH_2-C_6H_5$ | $-CH_2-C_6H_5$ | H | OH | $CH_3$ | H |
| $CH_3$ | $-CH_2-CH_2-C_6H_5$ | $-CH_2-CH_2-C_6H_5$ | H | OH | $CH_3$ | H |
| $CH_3$ | H | cyclopentyl | H | OH | $CH_3$ | H |
| $CH_3$ | H | cyclohexyl | H | OH | $CH_3$ | H |
| $CH_3$ | H | cycloheptyl | H | OH | $CH_3$ | H |
| $CH_3$ | \multicolumn{2}{c}{$R_2$ and $R_3$ together: cyclohexyl-COOH} | H | OH | $CH_3$ | H |
| $CH_3$ | \multicolumn{2}{c}{cyclohexyl-$CH_2$-COOH} | H | OH | $CH_3$ | H |
| $CH_3$ | \multicolumn{2}{c}{cyclohexyl-$CH_2$-$CH_2$-COOH} | H | OH | $CH_3$ | H |

TABLE IB-continued

| $R_1$ | $R_2$ | $R_3$ | $R_4$ | $R_5$ | $R_6$ | $R_7$ |
|---|---|---|---|---|---|---|
| $CH_3$ | cyclopentyl-COOH | | H | OH | $CH_3$ | H |
| $CH_3$ | cyclohexyl with COOH and OH | | H | OH | $CH_3$ | H |
| $C_2H_5$ | H | H | H | OH | $CH_3$ | H |
| $C_2H_5$ | H | $CH_3$ | H | OH | $CH_3$ | H |
| $C_2H_5$ | H | $C_2H_5$ | H | OH | $CH_3$ | H |
| $C_2H_5$ | H | $n\text{-}C_3H_7$ | H | OH | $CH_3$ | H |
| $C_2H_5$ | H | $n\text{-}C_4H_9$ | H | OH | $CH_3$ | H |
| $C_2H_5$ | H | $i\text{-}C_3H_7$ | H | OH | $CH_3$ | H |
| $C_2H_5$ | H | $i\text{-}C_4H_9$ | H | OH | $CH_3$ | H |
| $C_2H_5$ | H | $n\text{-}C_5H_{11}$ | H | OH | $CH_3$ | H |
| $C_2H_5$ | H | $n\text{-}C_6H_{13}$ | H | OH | $CH_3$ | H |
| $C_2H_5$ | H | $C_2H_4OH$ | H | OH | $CH_3$ | H |
| $C_2H_5$ | H | $-CH_2-CH(OH)-CH_3$ | H | OH | $CH_3$ | H |
| $C_2H_5$ | H | $-CH_2-CH_2-CH_2OH$ | H | OH | $CH_3$ | H |
| $C_2H_5$ | H | $-CH_2-CH_2-N(CH_3)_2$ | H | OH | $CH_3$ | H |
| $C_2H_5$ | H | $-CH_2-CH_2-N(C_2H_5)_2$ | H | OH | $CH_3$ | H |
| $C_2H_5$ | H | $-CH_2-CH_2-N(C_4H_9)_2$ | H | OH | $CH_3$ | H |
| $C_2H_5$ | H | $-CH_2-CH_2-CH_2-N(CH_3)_2$ | H | OH | $CH_3$ | H |
| $C_2H_5$ | H | $-CH_2-CH_2-CH_2-N(C_2H_5)_2$ | H | OH | $CH_3$ | H |
| $C_2H_5$ | H | $-CH_2-CON(CH_3)_2$ | H | OH | $CH_3$ | H |
| $C_2H_5$ | H | $-CH_2-CH_2-CON(CH_3)_2$ | H | OH | $CH_3$ | H |
| $C_2H_5$ | H | $-CH_2-CON(C_2H_5)_2$ | H | OH | $CH_3$ | H |
| $C_2H_5$ | H | $-CH_2-C_6H_5$ | H | OH | $CH_3$ | H |
| $C_2H_5$ | H | $-CH_2-CH_2-C_6H_5$ | H | OH | $CH_3$ | H |
| $C_2H_5$ | H | $-CH_2-CH_2-\text{pyrrolidinyl}$ | H | OH | $CH_3$ | H |
| $C_2H_5$ | H | $-CH_2-CH_2-\text{morpholinyl}$ | H | OH | $CH_3$ | H |
| $C_2H_5$ | H | $-CH_2-CH_2-\text{piperidinyl}$ | H | OH | $CH_3$ | H |
| $C_2H_5$ | H | $-CH_2-CH_2-\text{N-methylpiperazinyl}$ | H | OH | $CH_3$ | H |
| $C_2H_5$ | $n\text{-}C_5H_{11}$ | $n\text{-}C_5H_{11}$ | H | OH | $CH_3$ | H |
| $C_2H_5$ | $n\text{-}C_6H_{13}$ | $n\text{-}C_6H_{13}$ | H | OH | $CH_3$ | H |
| $C_2H_5$ | $i\text{-}C_3H_7$ | $i\text{-}C_3H_7$ | H | OH | $CH_3$ | H |
| $C_2H_5$ | $i\text{-}C_4H_9$ | $i\text{-}C_4H_9$ | H | OH | $CH_3$ | H |
| $C_2H_5$ | $C_2H_4OH$ | $C_2H_4OH$ | H | OH | $CH_3$ | H |
| $C_2H_5$ | $-CH_2-CH(OH)-CH_3$ | $-CH_2-CH(OH)-CH_3$ | H | OH | $CH_3$ | H |
| $C_2H_5$ | $-CH_3$ | $C_2H_4OH$ | H | OH | $CH_3$ | H |
| $C_2H_5$ | $-CH_2-CH_2-CH_2OH$ | $-CH_2-CH_2-CH_2OH$ | H | OH | $CH_3$ | H |
| $C_2H_5$ | $-CH_2-C_6H_5$ | $-CH_2-C_6H_5$ | H | OH | $CH_3$ | H |
| $C_2H_5$ | $-CH_2-CH_2-C_6H_5$ | $-CH_2-CH_2-C_6H_5$ | H | OH | $CH_3$ | H |
| $C_2H_5$ | H | cyclopentyl | H | OH | $CH_3$ | H |
| $C_2H_5$ | H | cyclohexyl | H | OH | $CH_3$ | H |
| $C_2H_5$ | H | cycloheptyl | H | OH | $CH_3$ | H |

TABLE IB-continued

| $R_1$ | $R_2$ | $R_3$ | $R_4$ | $R_5$ | $R_6$ | $R_7$ |
|---|---|---|---|---|---|---|
| $C_2H_5$ | |  cyclohexyl-COOH | H | OH | $CH_3$ | H |
| $C_2H_5$ | |  cyclohexyl-$CH_2$-COOH | H | OH | $CH_3$ | H |
| $C_2H_5$ | |  cyclohexyl-$CH_2$-$CH_2$-COOH | H | OH | $CH_3$ | H |
| $C_2H_5$ | | 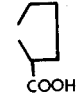 cyclopentyl-COOH | H | OH | $CH_3$ | H |
| $C_2H_5$ | | 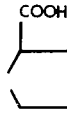 cyclopentyl(COOH)(OH) | H | OH | $CH_3$ | H |
| n-$C_3H_7$ | H | H | H | OH | $CH_3$ | H |
| n-$C_3H_7$ | H | $CH_3$ | H | OH | $CH_3$ | H |
| n-$C_3H_7$ | H | $C_2H_5$ | H | OH | $CH_3$ | H |
| n-$C_3H_7$ | H | n-$C_3H_7$ | H | OH | $CH_3$ | H |
| n-$C_3H_7$ | H | n-$C_4H_9$ | H | OH | $CH_3$ | H |
| n-$C_3H_7$ | H | i-$C_3H_7$ | H | OH | $CH_3$ | H |
| n-$C_3H_7$ | H | i-$C_4H_9$ | H | OH | $CH_3$ | H |
| n-$C_3H_7$ | H | n-$C_5H_{11}$ | H | OH | $CH_3$ | H |
| n-$C_3H_7$ | H | n-$C_6H_{13}$ | H | OH | $CH_3$ | H |
| n-$C_3H_7$ | H | $C_2H_4OH$ | H | OH | $CH_3$ | H |
| n-$C_3H_7$ | H | $-CH_2-CH(OH)-CH_3$ | H | OH | $CH_3$ | H |
| n-$C_3H_7$ | H | $-CH_2-CH_2-CH_2OH$ | H | OH | $CH_3$ | H |
| n-$C_3H_7$ | H | $-CH_2-CH_2-N(CH_3)_2$ | H | OH | $CH_3$ | H |
| n-$C_3H_7$ | H | $-CH_2-CH_2-N(C_2H_5)_2$ | H | OH | $CH_3$ | H |
| n-$C_3H_7$ | H | $-CH_2-CH_2-N(C_4H_9)_2$ | H | OH | $CH_3$ | H |
| n-$C_3H_7$ | H | $-CH_2-CH_2-CH_2-N(CH_3)_2$ | H | OH | $CH_3$ | H |
| n-$C_3H_7$ | H | $-CH_2-CH_2-CH_2-N(C_2H_5)_2$ | H | OH | $CH_3$ | H |
| n-$C_3H_7$ | H | $-CH_2-CON(CH_3)_2$ | H | OH | $CH_3$ | H |
| n-$C_3H_7$ | H | $-CH_2-CH_2-CON(CH_3)_2$ | H | OH | $CH_3$ | H |
| n-$C_3H_7$ | H | $-CH_2-CON(C_2H_5)_2$ | H | OH | $CH_3$ | H |
| n-$C_3H_7$ | H | $-CH_2-C_6H_5$ | H | OH | $CH_3$ | H |
| n-$C_3H_7$ | H | $-CH_2-CH_2-C_6H_5$ | H | OH | $CH_3$ | H |
| n-$C_3H_7$ | H | $-CH_2-CH_2-N$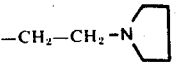 (pyrrolidinyl) | H | OH | $CH_3$ | H |
| n-$C_3H_7$ | H | $-CH_2-CH_2-N$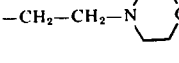 (morpholinyl) | H | OH | $CH_3$ | H |
| n-$C_3H_7$ | H | $-CH_2-CH_2-N$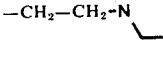 (piperidinyl) | H | OH | $CH_3$ | H |
| n-$C_3H_7$ | H | $-CH_2-CH_2-N$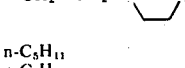$N-CH_3$ (N-methylpiperazinyl) | H | OH | $CH_3$ | H |
| n-$C_3H_7$ | n-$C_5H_{11}$ | n-$C_5H_{11}$ | H | OH | $CH_3$ | H |
| n-$C_3H_7$ | n-$C_6H_{13}$ | n-$C_6H_{13}$ | H | OH | $CH_3$ | H |
| n-$C_3H_7$ | i-$C_3H_7$ | i-$C_3H_7$ | H | OH | $CH_3$ | H |
| n-$C_3H_7$ | i-$C_4H_9$ | i-$C_4H_9$ | H | OH | $CH_3$ | H |
| n-$C_3H_7$ | $C_2H_4OH$ | $C_2H_4OH$ | H | OH | $CH_3$ | H |
| n-$C_3H_7$ | $-CH_2-CH(OH)-CH_3$ | $-CH_2-CH(OH)-CH_3$ | H | OH | $CH_3$ | H |
| n-$C_3H_7$ | $-CH_3$ | $C_2H_4OH$ | H | OH | $CH_3$ | H |
| n-$C_3H_7$ | $-CH_2-CH_2-CH_2OH$ | $-CH_2-CH_2-CH_2OH$ | H | OH | $CH_3$ | H |
| n-$C_3H_7$ | $-CH_2-C_6H_5$ | $-CH_2-C_6H_5$ | H | OH | $CH_3$ | H |
| n-$C_3H_7$ | $-CH_2-CH_2-C_6H_5$ | $-CH_2-CH_2-C_6H_5$ | H | OH | $CH_3$ | H |
| n-$C_3H_7$ | H |  cyclopentyl | H | OH | $CH_3$ | H |

TABLE IB-continued

| $R_1$ | $R_2$ | $R_3$ | $R_4$ | $R_5$ | $R_6$ | $R_7$ |
|---|---|---|---|---|---|---|
| n-$C_3H_7$ | H | cyclohexyl | H | OH | $CH_3$ | H |
| n-$C_3H_7$ | H | cycloheptyl | H | OH | $CH_3$ | H |
| n-$C_3H_7$ | H | cyclohexyl-COOH | H | OH | $CH_3$ | H |
| n-$C_3H_7$ | H | cyclohexyl-$CH_2$-COOH | H | OH | $CH_3$ | H |
| n-$C_3H_7$ | H | cyclohexyl-$CH_2$-$CH_2$-COOH | H | OH | $CH_3$ | H |
| n-$C_3H_7$ | cyclopentyl-COOH | | H | OH | $CH_3$ | H |
| n-$C_3H_7$ | cyclopentyl(COOH)(OH) | | H | OH | $CH_3$ | H |
| n-$C_4H_9$ | H | H | H | OH | $CH_3$ | H |
| n-$C_4H_9$ | H | $CH_3$ | H | OH | $CH_3$ | H |
| n-$C_4H_9$ | H | $C_2H_5$ | H | OH | $CH_3$ | H |
| n-$C_4H_9$ | H | n-$C_3H_7$ | H | OH | $CH_3$ | H |
| n-$C_4H_9$ | H | n-$C_4H_9$ | H | OH | $CH_3$ | H |
| n-$C_4H_9$ | H | i-$C_3H_7$ | H | OH | $CH_3$ | H |
| n-$C_4H_9$ | H | i-$C_4H_9$ | H | OH | $CH_3$ | H |
| n-$C_4H_9$ | H | n-$C_5H_{11}$ | H | OH | $CH_3$ | H |
| n-$C_4H_9$ | H | n-$C_6H_{13}$ | H | OH | $CH_3$ | H |
| n-$C_4H_9$ | H | $C_2H_4OH$ | H | OH | $CH_3$ | H |
| n-$C_4H_9$ | H | $-CH_2-CH(OH)-CH_3$ | H | OH | $CH_3$ | H |
| n-$C_4H_9$ | H | $-CH_2-CH_2-CH_2OH$ | H | OH | $CH_3$ | H |
| n-$C_4H_9$ | H | $-CH_2-CH_2-N(CH_3)_2$ | H | OH | $CH_3$ | H |
| n-$C_4H_9$ | H | $-CH_2-CH_2-N(C_2H_5)_2$ | H | OH | $CH_3$ | H |
| n-$C_4H_9$ | H | $-CH_2-CH_2-N(C_4H_9)_2$ | H | OH | $CH_3$ | H |
| n-$C_4H_9$ | H | $-CH_2-CH_2-CH_2-N(CH_3)_2$ | H | OH | $CH_3$ | H |
| n-$C_4H_9$ | H | $-CH_2-CH_2-CH_2-N(C_2H_5)_2$ | H | OH | $CH_3$ | H |
| n-$C_4H_9$ | H | $-CH_2-CON(CH_3)_2$ | H | OH | $CH_3$ | H |
| n-$C_4H_9$ | H | $-CH_2-CH_2-CON(CH_3)_2$ | H | OH | $CH_3$ | H |
| n-$C_4H_9$ | H | $-CH_2-CON(C_2H_5)_2$ | H | OH | $CH_3$ | H |
| n-$C_4H_9$ | H | $-CH_2-C_6H_5$ | H | OH | $CH_3$ | H |
| n-$C_4H_9$ | H | $-CH_2-CH_2-C_6H_5$ | H | OH | $CH_3$ | H |
| n-$C_4H_9$ | H | $-CH_2-CH_2-$pyrrolidinyl | H | OH | $CH_3$ | H |
| n-$C_4H_9$ | H | $-CH_2-CH_2-$morpholinyl | H | OH | $CH_3$ | H |
| n-$C_4H_9$ | H | $-CH_2-CH_2-$piperidinyl | H | OH | $CH_3$ | H |
| n-$C_4H_9$ | H | $-CH_2-CH_2-$N-methylpiperazinyl | H | OH | $CH_3$ | H |
| n-$C_4H_9$ | n-$C_5H_{11}$ | n-$C_5H_{11}$ | H | OH | $CH_3$ | H |
| n-$C_4H_9$ | n-$C_6H_{13}$ | n-$C_6H_{13}$ | H | OH | $CH_3$ | H |
| n-$C_4H_9$ | i-$C_3H_7$ | i-$C_3H_7$ | H | OH | $CH_3$ | H |
| n-$C_4H_9$ | i-$C_4H_9$ | i-$C_4H_9$ | H | OH | $CH_3$ | H |
| n-$C_4H_9$ | $C_2H_4OH$ | $C_2H_4OH$ | H | OH | $CH_3$ | H |
| n-$C_4H_9$ | $-CH_2-CH(OH)-CH_3$ | $-CH_2-CH(OH)-CH_3$ | H | OH | $CH_3$ | H |

TABLE IB-continued

| R₁ | R₂ | R₃ | R₄ | R₅ | R₆ | R₇ |
|---|---|---|---|---|---|---|
| n-C₄H₉ | —CH₃ | C₂H₄OH | H | OH | CH₃ | H |
| n-C₄H₉ | —CH₂—CH₂—CH₂OH | —CH₂—CH₂—CH₂OH | H | OH | CH₃ | H |
| n-C₄H₉ | —CH₂—C₆H₅ | —CH₂—C₆H₅ | H | OH | CH₃ | H |
| n-C₄H₉ | —CH₂—CH₂—C₆H₅ | —CH₂—CH₂—C₆H₅ | H | OH | CH₃ | H |
| n-C₄H₉ | H |  | H | OH | CH₃ | H |
| n-C₄H₉ | H |  | H | OH | CH₃ | H |
| n-C₄H₉ | H |  | H | OH | CH₃ | H |
| n-C₄H₉ | 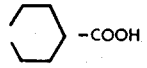 | | H | OH | CH₃ | H |
| n-C₄H₉ | 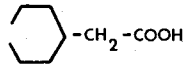 | | H | OH | CH₃ | H |
| n-C₄H₉ | 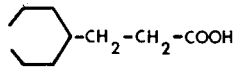 | | H | OH | CH₃ | H |
| n-C₄H₉ | 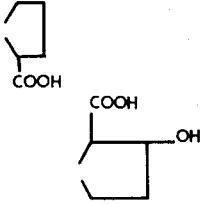 | | H | OH | CH₃ | H |
| n-C₄H₉ | 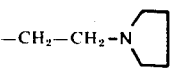 | | H | OH | CH₃ | H |
| i-C₃H₇ | H | H | H | OH | CH₃ | H |
| i-C₃H₇ | H | CH₃ | H | OH | CH₃ | H |
| i-C₃H₇ | H | C₂H₅ | H | OH | CH₃ | H |
| i-C₃H₇ | H | n-C₃H₇ | H | OH | CH₃ | H |
| i-C₃H₇ | H | n-C₄H₉ | H | OH | CH₃ | H |
| i-C₃H₇ | H | i-C₃H₇ | H | OH | CH₃ | H |
| i-C₃H₇ | H | i-C₄H₉ | H | OH | CH₃ | H |
| i-C₃H₇ | H | n-C₅H₁₁ | H | OH | CH₃ | H |
| i-C₃H₇ | H | n-C₆H₁₃ | H | OH | CH₃ | H |
| i-C₃H₇ | H | C₂H₄OH | H | OH | CH₃ | H |
| i-C₃H₇ | H | —CH₂—CH(OH)—CH₃ | H | OH | CH₃ | H |
| i-C₃H₇ | H | —CH₂—CH₂—CH₂OH | H | OH | CH₃ | H |
| i-C₃H₇ | H | —CH₂—CH₂—N(CH₃)₂ | H | OH | CH₃ | H |
| i-C₃H₇ | H | —CH₂—CH₂—N(C₂H₅)₂ | H | OH | CH₃ | H |
| i-C₃H₇ | H | —CH₂—CH₂—N(C₄H₉)₂ | H | OH | CH₃ | H |
| i-C₃H₇ | H | —CH₂—CH₂—CH₂—N(CH₃)₂ | H | OH | CH₃ | H |
| i-C₃H₇ | H | —CH₂—CH₂—CH₂—N(C₂H₅)₂ | H | OH | CH₃ | H |
| i-C₃H₇ | H | —CH₂—CON(CH₃)₂ | H | OH | CH₃ | H |
| i-C₃H₇ | H | —CH₂—CH₂—CON(CH₃)₂ | H | OH | CH₃ | H |
| i-C₃H₇ | H | —CH₂—CON(C₂H₅)₂ | H | OH | CH₃ | H |
| i-C₃H₇ | H | —CH₂—C₆H₅ | H | OH | CH₃ | H |
| i-C₃H₇ | H | —CH₂—CH₂—C₆H₅ | H | OH | CH₃ | H |
| i-C₃H₇ | H | 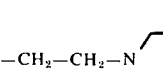 | H | OH | CH₃ | H |
| i-C₃H₇ | H |  | H | OH | CH₃ | H |
| i-C₃H₇ | H |  | H | OH | CH₃ | H |

TABLE IB-continued

| R₁ | R₂ | R₃ | R₄ | R₅ | R₆ | R₇ |
|---|---|---|---|---|---|---|
| i-C₃H₇ | H | —CH₂—CH₂—N(piperazine)N—CH₃ | H | OH | CH₃ | H |
| i-C₃H₇ | n-C₅H₁₁ | n-C₅H₁₁ | H | OH | CH₃ | H |
| i-C₃H₇ | n-C₆H₁₃ | n-C₆H₁₃ | H | OH | CH₃ | H |
| i-C₃H₇ | i-C₃H₇ | i-C₃H₇ | H | OH | CH₃ | H |
| i-C₃H₇ | i-C₄H₉ | i-C₄H₉ | H | OH | CH₃ | H |
| i-C₃H₇ | C₂H₄OH | C₂H₄OH | H | OH | CH₃ | H |
| i-C₃H₇ | —CH₂—CH(OH)—CH₃ | —CH₂—CH(OH)—CH₃ | H | OH | CH₃ | H |
| i-C₃H₇ | —CH₃ | C₂H₄OH | H | OH | CH₃ | H |
| i-C₃H₇ | —CH₂—CH₂—CH₂OH | —CH₂—CH₂—CH₂OH | H | OH | CH₃ | H |
| i-C₃H₇ | —CH₂—C₆H₅ | —CH₂—C₆H₅ | H | OH | CH₃ | H |
| i-C₃H₇ | —CH₂—CH₂—C₆H₅ | —CH₂—CH₂—C₆H₅ | H | OH | CH₃ | H |
| i-C₃H₇ | H | cyclopentyl | H | OH | CH₃ | H |
| i-C₃H₇ | H | cyclohexyl | H | OH | CH₃ | H |
| i-C₃H₇ | H | cycloheptyl | H | OH | CH₃ | H |
| i-C₃H₇ | | cyclohexyl—COOH | H | OH | CH₃ | H |
| i-C₃H₇ | | cyclohexyl—CH₂—COOH | H | OH | CH₃ | H |
| i-C₃H₇ | | cyclohexyl—CH₂—CH₂—COOH | H | OH | CH₃ | H |
| i-C₃H₇ | cyclopentyl-COOH | | H | OH | CH₃ | H |
| i-C₃H₇ | | cyclopentyl(COOH)(OH) | H | OH | CH₃ | H |
| i-C₄H₉ | H | H | H | OH | CH₃ | H |
| i-C₄H₉ | H | CH₃ | H | OH | CH₃ | H |
| i-C₄H₉ | H | C₂H₅ | H | OH | CH₃ | H |
| i-C₄H₉ | H | n-C₃H₇ | H | OH | CH₃ | H |
| i-C₄H₉ | H | n-C₄H₉ | H | OH | CH₃ | H |
| i-C₄H₉ | H | i-C₃H₇ | H | OH | CH₃ | H |
| i-C₄H₉ | H | i-C₄H₉ | H | OH | CH₃ | H |
| i-C₄H₉ | H | n-C₅H₁₁ | H | OH | CH₃ | H |
| i-C₄H₉ | H | n-C₆H₁₃ | H | OH | CH₃ | H |
| i-C₄H₉ | H | C₂H₄OH | H | OH | CH₃ | H |
| i-C₄H₉ | H | —CH₂—CH(OH)—CH₃ | H | OH | CH₃ | H |
| i-C₄H₉ | H | —CH₂—CH₂—CH₂OH | H | OH | CH₃ | H |
| i-C₄H₉ | H | —CH₂—CH₂—N(CH₃)₂ | H | OH | CH₃ | H |
| i-C₄H₉ | H | —CH₂—CH₂—N(C₂H₅)₂ | H | OH | CH₃ | H |
| i-C₄H₉ | H | —CH₂—CH₂—N(C₄H₉)₂ | H | OH | CH₃ | H |
| i-C₄H₉ | H | —CH₂—CH₂—CH₂—N(CH₃)₂ | H | OH | CH₃ | H |
| i-C₄H₉ | H | —CH₂—CH₂—CH₂—N(C₂H₅)₂ | H | OH | CH₃ | H |
| i-C₄H₉ | H | —CH₂—CON(CH₃)₂ | H | OH | CH₃ | H |
| i-C₄H₉ | H | —CH₂—CH₂—CON(CH₃)₂ | H | OH | CH₃ | H |
| i-C₄H₉ | H | —CH₂—CON(C₂H₅)₂ | H | OH | CH₃ | H |
| i-C₄H₉ | H | —CH₂—C₆H₅ | H | OH | CH₃ | H |
| i-C₄H₉ | H | —CH₂—CH₂—C₆H₅ | H | OH | CH₃ | H |
| i-C₄H₉ | H | —CH₂—CH₂—N(pyrrolidine) | H | OH | CH₃ | H |

TABLE IB-continued

| R₁ | R₂ | R₃ | R₄ | R₅ | R₆ | R₇ |
|---|---|---|---|---|---|---|
| i-C₄H₉ | H | —CH₂—CH₂—NO | H | OH | CH₃ | H |
| i-C₄H₉ | H | —CH₂—CH₂—N | H | OH | CH₃ | H |
| i-C₄H₉ | H | —CH₂—CH₂—NN—CH₃ | H | OH | CH₃ | H |
| i-C₄H₉ | n-C₅H₁₁ | n-C₅H₁₁ | H | OH | CH₃ | H |
| i-C₄H₉ | n-C₆H₁₃ | n-C₆H₁₃ | H | OH | CH₃ | H |
| i-C₄H₉ | i-C₃H₇ | i-C₃H₇ | H | OH | CH₃ | H |
| i-C₄H₉ | i-C₄H₉ | i-C₄H₉ | H | OH | CH₃ | H |
| i-C₄H₉ | C₂H₄OH | C₂H₄OH | H | OH | CH₃ | H |
| i-C₄H₉ | —CH₂—CH(OH)—CH₃ | —CH₂—CH(OH)—CH₃ | H | OH | CH₃ | H |
| i-C₄H₉ | —CH₃ | C₂H₄OH | H | OH | CH₃ | H |
| i-C₄H₉ | —CH₂—CH₂—CH₂OH | —CH₂—CH₂—CH₂OH | H | OH | CH₃ | H |
| i-C₄H₉ | —CH₂—C₆H₅ | —CH₂—C₆H₅ | H | OH | CH₃ | H |
| i-C₄H₉ | —CH₂—CH₂—C₆H₅ | —CH₂—CH₂—C₆H₅ | H | OH | CH₃ | H |
| i-C₄H₉ | H |  | H | OH | CH₃ | H |
| i-C₄H₉ | H |  | H | OH | CH₃ | H |
| i-C₄H₉ | H |  | H | OH | CH₃ | H |
| i-C₄H₉ | | —COOH | H | OH | CH₃ | H |
| i-C₄H₉ | | —CH₂—COOH | H | OH | CH₃ | H |
| i-C₄H₉ | | —CH₂—CH₂—COOH | H | OH | CH₃ | H |
| i-C₄H₉ | COOH | | H | OH | CH₃ | H |
| i-C₄H₉ | |  | H | OH | CH₃ | H |
| sec.-C₄H₉ | H | H | H | OH | CH₃ | H |
| sec.-C₄H₉ | H | CH₃ | H | OH | CH₃ | H |
| sec.-C₄H₉ | H | C₂H₅ | H | OH | CH₃ | H |
| sec.-C₄H₉ | H | n-C₃H₇ | H | OH | CH₃ | H |
| sec.-C₄H₉ | H | n-C₄H₉ | H | OH | CH₃ | H |
| sec.-C₄H₉ | H | i-C₃H₇ | H | OH | CH₃ | H |
| sec.-C₄H₉ | H | i-C₄H₉ | H | OH | CH₃ | H |
| sec.-C₄H₉ | H | n-C₅H₁₁ | H | OH | CH₃ | H |
| sec.-C₄H₉ | H | n-C₆H₁₃ | H | OH | CH₃ | H |
| sec.-C₄H₉ | H | C₂H₄OH | H | OH | CH₃ | H |
| sec.-C₄H₉ | H | —CH₂—CH(OH)—CH₃ | H | OH | CH₃ | H |
| sec.-C₄H₉ | H | —CH₂—CH₂—CH₂OH | H | OH | CH₃ | H |
| sec.-C₄H₉ | H | —CH₂—CH₂—N(CH₃)₂ | H | OH | CH₃ | H |
| sec.-C₄H₉ | H | —CH₂—CH₂—N(C₂H₅)₂ | H | OH | CH₃ | H |
| sec.-C₄H₉ | H | —CH₂—CH₂—N(C₄H₉)₂ | H | OH | CH₃ | H |
| sec.-C₄H₉ | H | —CH₂—CH₂—CH₂—N(CH₃)₂ | H | OH | CH₃ | H |
| sec.-C₄H₉ | H | —CH₂—CH₂—CH₂—N(C₂H₅)₂ | H | OH | CH₃ | H |
| sec.-C₄H₉ | H | —CH₂—CON(CH₃)₂ | H | OH | CH₃ | H |
| sec.-C₄H₉ | H | —CH₂—CON(CH₃)₂ | H | OH | CH₃ | H |
| sec.-C₄H₉ | H | —CH₂—CON(C₂H₅)₂ | H | OH | CH₃ | H |
| sec.-C₄H₉ | H | —CH₂—C₆H₅ | H | OH | CH₃ | H |
| sec.-C₄H₉ | H | —CH₂—CH₂—C₆H₅ | H | OH | CH₃ | H |

TABLE IB-continued

| R₁ | R₂ | R₃ | R₄ | R₅ | R₆ | R₇ |
|---|---|---|---|---|---|---|
| sec.-C₄H₉ | H | —CH₂—CH₂—N(pyrrolidinyl) | H | OH | CH₃ | H |
| sec.-C₄H₉ | H | —CH₂—CH₂—N(morpholinyl) | H | OH | CH₃ | H |
| sec.-C₄H₉ | H | —CH₂—CH₂—N(piperidinyl) | H | OH | CH₃ | H |
| sec.-C₄H₉ | H | —CH₂—CH₂—N(N′-methylpiperazinyl) | H | OH | CH₃ | H |
| sec.-C₄H₉ | n-C₅H₁₁ | n-C₅H₁₁ | H | OH | CH₃ | H |
| sec.-C₄H₉ | n-C₆H₁₃ | n-C₆H₁₃ | H | OH | CH₃ | H |
| sec.-C₄H₉ | i-C₃H₇ | i-C₃H₇ | H | OH | CH₃ | H |
| sec.-C₄H₉ | i-C₄H₉ | i-C₄H₉ | H | OH | CH₃ | H |
| sec.-C₄H₉ | C₂H₄OH | C₂H₄OH | H | OH | CH₃ | H |
| sec.-C₄H₉ | —CH₂—CH(OH)—CH₃ | —CH₂—CH(OH)—CH₃ | H | OH | CH₃ | H |
| sec.-C₄H₉ | —CH₃ | C₂H₄OH | H | OH | CH₃ | H |
| sec.-C₄H₉ | —CH₂—CH₂—CH₂OH | —CH₂—CH₂—CH₂OH | H | OH | CH₃ | H |
| sec.-C₄H₉ | —CH₂—CH₂—CH₂OH | —CH₂—CH₂—CH₂OH | H | OH | CH₃ | H |
| sec.-C₄H₉ | —CH₂—C₆H₅ | —CH₂—C₆H₅ | H | OH | CH₃ | H |
| sec.-C₄H₉ | —CH₂—CH₂—C₆H₅ | —CH₂—CH₂—C₆H₅ | H | OH | CH₃ | H |
| sec.-C₄H₉ | H | cyclopentyl | H | OH | CH₃ | H |
| sec.-C₄H₉ | H | cyclohexyl | H | OH | CH₃ | H |
| sec.-C₄H₉ | H | cycloheptyl | H | OH | CH₃ | H |
| sec.-C₄H₉ | H | cyclohexyl—COOH | H | OH | CH₃ | H |
| sec.-C₄H₉ | H | cyclohexyl—CH₂—COOH | H | OH | CH₃ | H |
| sec.-C₄H₉ | H | cyclohexyl—CH₂—CH₂—COOH | H | OH | CH₃ | H |
| sec.-C₄H₉ | cyclopentyl-COOH | | H | OH | CH₃ | H |
| sec.-C₄H₉ | | cyclopentyl(COOH)(OH) | H | OH | CH₃ | H |

TABLE IIA

| R₁ | R₂ | R₃ | R₄ | R₅ | R₆ | R₇ |
|---|---|---|---|---|---|---|
| CH₃ | CH₃ | CH₃ | OH | OH | CH₃ | H |
| CH₃ | CH₃ | C₂H₅ | OH | OH | CH₃ | H |
| CH₃ | C₂H₅ | C₂H₅ | OH | OH | CH₃ | H |
| CH₃ | n-C₃H₇ | n-C₃H₇ | OH | OH | CH₃ | H |
| CH₃ | n-C₄H₉ | n-C₄H₉ | OH | OH | CH₃ | H |
| CH₃ | H | CH₂—COOH | OH | OH | CH₃ | H |
| CH₃ | H | CH₂—COOC₂H₅ | OH | OH | CH₃ | H |
| CH₃ | H | CH₃—CH—COOH | OH | OH | CH₃ | H |
| CH₃ | H | CH₃—CH(—)—COOC₂H₅ | OH | OH | CH₃ | H |
| CH₃ | H | —CH₂—CH₂—COOH | OH | OH | CH₃ | H |
| CH₃ | H | —CH₂—CH₂—COOC₂H₅ | OH | OH | CH₃ | H |
| CH₃ | H | —(CH₂)₄—CH(NH₂)—COOH | OH | OH | CH₃ | H |

TABLE IIA-continued

| R₁ | R₂ | R₃ | R₄ | R₅ | R₆ | R₇ |
|---|---|---|---|---|---|---|
| CH₃ | [cyclohexyl structure] | | OH | OH | CH₃ | H |
| CH₃ | [cyclohexyl structure] | | OH | OH | CH₃ | H |
| CH₃ | [morpholine structure with O] | | OH | OH | CH₃ | H |
| CH₃ | [piperidine N structure] | | OH | OH | CH₃ | H |
| CH₃ | [N-CH₃ piperazine] | | OH | OH | CH₃ | H |
| CH₃ | [N-C₂H₅ piperazine] | | OH | OH | CH₃ | H |
| CH₃ | [N-C₂H₅OH piperazine] | | OH | OH | CH₃ | H |
| C₂H₅ | CH₃ | CH₃ | OH | OH | CH₃ | H |
| C₂H₅ | CH₃ | C₂H₅ | OH | OH | CH₃ | H |
| C₂H₅ | C₂H₅ | C₂H₅ | OH | OH | CH₃ | H |
| C₂H₅ | n-C₃H₇ | n-C₃H₇ | OH | OH | CH₃ | H |
| C₂H₅ | n-C₄H₉ | n-C₄H₉ | OH | OH | CH₃ | H |
| C₂H₅ | H | CH₂—COOH | OH | OH | CH₃ | H |
| C₂H₅ | H | CH₂—COOC₂H₅ | OH | OH | CH₃ | H |
| C₂H₅ | H | CH₃—CH—COOH | OH | OH | CH₃ | H |
| C₂H₅ | H | CH₃—CH—COOC₂H₅ | OH | OH | CH₃ | H |
| C₂H₅ | H | —CH₂—CH₂—COOH | OH | OH | CH₃ | H |
| C₂H₅ | H | —CH₂—CH₂—COOC₂H₅ | OH | OH | CH₃ | H |
| C₂H₅ | H | —(CH₂)₄—CH(NH₂)—COOH | OH | OH | CH₃ | H |
| C₂H₅ | [cyclohexyl structure] | | OH | OH | CH₃ | H |
| C₂H₅ | [morpholine structure] | | OH | OH | CH₃ | H |
| C₂H₅ | [piperidine N] | | OH | OH | CH₃ | H |
| C₂H₅ | [N-CH₃ piperazine] | | OH | OH | CH₃ | H |
| C₂H₅ | [N-C₂H₅ piperazine] | | OH | OH | CH₃ | H |
| C₂H₅ | [N-C₂H₅OH piperazine] | | OH | OH | CH₃ | H |
| n-C₃H₇ | CH₃ | CH₃ | OH | OH | CH₃ | H |
| n-C₃H₇ | CH₃ | C₂H₅ | OH | OH | CH₃ | H |
| n-C₃H₇ | C₂H₅ | C₂H₅ | OH | OH | CH₃ | H |
| n-C₃H₇ | n-C₃H₇ | n-C₃H₇ | OH | OH | CH₃ | H |
| n-C₃H₇ | n-C₄H₉ | n-C₄H₉ | OH | OH | CH₃ | H |
| n-C₃H₇ | H | CH₂—COOH | OH | OH | CH₃ | H |
| n-C₃H₇ | H | CH₂—COOC₂H₅ | OH | OH | CH₃ | H |
| n-C₃H₇ | H | CH₃—CH—COOH | OH | OH | CH₃ | H |
| n-C₃H₇ | H | CH₃—CH—COOC₂H₅ | OH | OH | CH₃ | H |
| n-C₃H₇ | H | —CH₂—CH₂—COOH | OH | OH | CH₃ | H |
| n-C₃H₇ | H | —CH₂—CH₂—COOC₂H₅ | OH | OH | CH₃ | H |
| n-C₃H₇ | H | —(CH₂)₄—CH(NH₂)—COOH | OH | OH | CH₃ | H |
| n-C₃H₇ | [cyclohexyl structure] | | OH | OH | CH₃ | H |
| n-C₃H₇ | [cyclohexyl structure] | | OH | OH | CH₃ | H |
| n-C₃H₇ | [morpholine structure] | | OH | OH | CH₃ | H |
| n-C₃H₇ | [N-CH₃ piperazine] | | OH | OH | CH₃ | H |
| n-C₃H₇ | [N-C₂H₅ piperazine] | | OH | OH | CH₃ | H |
| n-C₃H₇ | [N-C₂H₅OH piperazine] | | OH | OH | CH₃ | H |
| n-C₄H₉ | CH₃ | CH₃ | OH | OH | CH₃ | H |
| n-C₄H₉ | CH₃ | C₂H₅ | OH | OH | CH₃ | H |
| n-C₄H₉ | C₂H₅ | C₂H₅ | OH | OH | CH₃ | H |
| n-C₄H₉ | n-C₃H₇ | n-C₃H₇ | OH | OH | CH₃ | H |
| n-C₄H₉ | n-C₄H₉ | n-C₄H₉ | OH | OH | CH₃ | H |
| n-C₄H₉ | H | CH₂—COOH | OH | OH | CH₃ | H |
| n-C₄H₉ | H | CH₂—COOC₂H₅ | OH | OH | CH₃ | H |
| n-C₄H₉ | H | CH₃—CH—COOH | OH | OH | CH₃ | H |
| n-C₄H₉ | H | CH₃—CH—COOC₂H₅ | OH | OH | CH₃ | H |
| n-C₄H₉ | H | —CH₂—CH₂—COOH | OH | OH | CH₃ | H |
| n-C₄H₉ | H | —CH₂—CH₂—COOC₂H₅ | OH | OH | CH₃ | H |
| n-C₄H₉ | H | —(CH₂)₄—CH(NH₂)—COOH | OH | OH | CH₃ | H |
| n-C₄H₉ | [cyclohexyl structure] | | OH | OH | CH₃ | H |
| n-C₄H₉ | [cyclohexyl structure] | | OH | OH | CH₃ | H |
| n-C₄H₉ | [morpholine structure] | | OH | OH | CH₃ | H |
| n-C₄H₉ | [piperidine N] | | OH | OH | CH₃ | H |
| n-C₄H₉ | [N-CH₃ piperazine] | | OH | OH | CH₃ | H |
| n-C₄H₉ | [N-C₂H₅ piperazine] | | OH | OH | CH₃ | H |
| n-C₄H₉ | [N-C₂H₅OH piperazine] | | OH | OH | CH₃ | H |

TABLE IIB

| R₁ | R₂ | R₃ | R₄ | R₅ | R₆ | R₇ |
|---|---|---|---|---|---|---|
| CH₃ | H | H | OH | OH | CH₃ | H |
| CH₃ | H | CH₃ | OH | OH | CH₃ | H |
| CH₃ | H | C₂H₅ | OH | OH | CH₃ | H |
| CH₃ | H | n-C₃H₇ | OH | OH | CH₃ | H |
| CH₃ | H | n-C₄H₉ | OH | OH | CH₃ | H |
| CH₃ | H | i-C₃H₇ | OH | OH | CH₃ | H |
| CH₃ | H | i-C₄H₉ | OH | OH | CH₃ | H |
| CH₃ | H | n-C₅H₁₁ | OH | OH | CH₃ | H |
| CH₃ | H | n-C₆H₁₃ | OH | OH | CH₃ | H |
| CH₃ | H | C₂H₄OH | OH | OH | CH₃ | H |
| CH₃ | H | —CH₂—CH(OH)—CH₃ | OH | OH | CH₃ | H |
| CH₃ | H | —CH₂—CH₂—CH₂OH | OH | OH | CH₃ | H |
| CH₃ | H | —CH₂—CH₂—N(CH₃)₂ | OH | OH | CH₃ | H |

TABLE IIB—continued

| R₁ | R₂ | R₃ | R₄ | R₅ | R₆ | R₇ |
|---|---|---|---|---|---|---|
| CH₃ | H | —CH₂—CH₂—N(C₂H₅)₂ | OH | OH | CH₃ | H |
| CH₃ | H | —CH₂—CH₂—N(C₄H₉)₂ | OH | OH | CH₃ | H |
| CH₃ | H | —CH₂—CH₂—CH₂—N(CH₃)₂ | OH | OH | CH₃ | H |
| CH₃ | H | —CH₂—CH₂—CH₂—N(C₂H₅)₂ | OH | OH | CH₃ | H |
| CH₃ | H | —CH₂—CON(CH₃)₂ | OH | OH | CH₃ | H |
| CH₃ | H | —CH₂—CH₂—CON(CH₃)₂ | OH | OH | CH₃ | H |
| CH₃ | H | —CH₂—CON(C₂H₅)₂ | OH | OH | CH₃ | H |
| CH₃ | H | —CH₂—C₆H₅ | OH | OH | CH₃ | H |
| CH₃ | H | —CH₂—CH₂—C₆H₅ | OH | OH | CH₃ | H |
| CH₃ | H | —CH₂—CH₂—N(pyrrolidinyl) | OH | OH | CH₃ | H |
| CH₃ | H | —CH₂—CH₂—N(morpholinyl) | OH | OH | CH₃ | H |
| CH₃ | H | —CH₂—CH₂—N(piperidinyl) | OH | OH | CH₃ | H |
| CH₃ | H | —CH₂—CH₂—N(N'-methylpiperazinyl) | OH | OH | CH₃ | H |
| CH₃ | n-C₅H₁₁ | n-C₅H₁₁ | OH | OH | CH₃ | H |
| CH₃ | n-C₆H₁₃ | n-C₆H₁₃ | OH | OH | CH₃ | H |
| CH₃ | i-C₃H₇ | i-C₃H₇ | OH | OH | CH₃ | H |
| CH₃ | i-C₄H₉ | i-C₄H₉ | OH | OH | CH₃ | H |
| CH₃ | C₂H₄OH | C₂H₄OH | OH | OH | CH₃ | H |
| CH₃ | —CH₂—CH(OH)—CH₃ | —CH₂—CH(OH)—CH₃ | OH | OH | CH₃ | H |
| CH₃ | —CH₃ | C₂H₄OH | OH | OH | CH₃ | H |
| CH₃ | —CH₂—CH₂—CH₂OH | —CH₂—CH₂—CH₂OH | OH | OH | CH₃ | H |
| CH₃ | —CH₂—C₆H₅ | —CH₂—C₆H₅ | OH | OH | CH₃ | H |
| CH₃ | —CH₂—CH₂—C₆H₅ | —CH₂—CH₂—C₆H₅ | OH | OH | CH₃ | H |
| CH₃ | H | cyclopentyl | OH | OH | CH₃ | H |
| CH₃ | H | cyclohexyl | OH | OH | CH₃ | H |
| CH₃ | H | cycloheptyl | OH | OH | CH₃ | H |
| CH₃ | cyclohexyl-COOH (R₂ and R₃ bracketed together) | | OH | OH | CH₃ | H |
| CH₃ | cyclohexyl-CH₂-COOH | | OH | OH | CH₃ | H |
| CH₃ | cyclohexyl-CH₂-CH₂-COOH | | OH | OH | CH₃ | H |
| CH₃ | cyclopentyl-COOH | | OH | OH | CH₃ | H |
| CH₃ | cyclopentyl(COOH)(OH) | | OH | OH | CH₃ | H |
| C₂H₅ | H | H | OH | OH | CH₃ | H |
| C₂H₅ | H | CH₃ | OH | OH | CH₃ | H |
| C₂H₅ | H | C₂H₅ | OH | OH | CH₃ | H |
| C₂H₅ | H | n-C₃H₇ | OH | OH | CH₃ | H |
| C₂H₅ | H | n-C₄H₉ | OH | OH | CH₃ | H |

TABLE IIB—continued

| $R_1$ | $R_2$ | $R_3$ | $R_4$ | $R_5$ | $R_6$ | $R_7$ |
|---|---|---|---|---|---|---|
| $C_2H_5$ | H | $i$-$C_3H_7$ | OH | OH | $CH_3$ | H |
| $C_2H_5$ | H | $i$-$C_4H_9$ | OH | OH | $CH_3$ | H |
| $C_2H_5$ | H | $n$-$C_5H_{11}$ | OH | OH | $CH_3$ | H |
| $C_2H_5$ | H | $n$-$C_6H_{13}$ | OH | OH | $CH_3$ | H |
| $C_2H_5$ | H | $C_2H_4OH$ | OH | OH | $CH_3$ | H |
| $C_2H_5$ | H | —$CH_2$—CH—$CH_3$<br>         $\|$<br>        OH | OH | OH | $CH_3$ | H |
| $C_2H_5$ | H | —$CH_2$—$CH_2$—$CH_2OH$ | OH | OH | $CH_3$ | H |
| $C_2H_5$ | H | —$CH_2$—$CH_2$—$N(CH_3)_2$ | OH | OH | $CH_3$ | H |
| $C_2H_5$ | H | —$CH_2$—$CH_2$—$N(C_2H_5)_2$ | OH | OH | $CH_3$ | H |
| $C_2H_5$ | H | —$CH_2$—$CH_2$—$N(C_4H_9)_2$ | OH | OH | $CH_3$ | H |
| $C_2H_5$ | H | —$CH_2$—$CH_2$—$CH_2$—$N(CH_3)_2$ | OH | OH | $CH_3$ | H |
| $C_2H_5$ | H | —$CH_2$—$CH_2$—$CH_2$—$N(C_2H_5)_2$ | OH | OH | $CH_3$ | H |
| $C_2H_5$ | H | —$CH_2$—$CON(CH_3)_2$ | OH | OH | $CH_3$ | H |
| $C_2H_5$ | H | —$CH_2$—$CH_2$—$CON(CH_3)_2$ | OH | OH | $CH_3$ | H |
| $C_2H_5$ | H | —$CH_2$—$CON(C_2H_5)_2$ | OH | OH | $CH_3$ | H |
| $C_2H_5$ | H | —$CH_2$—$C_6H_5$ | OH | OH | $CH_3$ | H |
| $C_2H_5$ | H | —$CH_2$—$CH_2$—$C_6H_5$ | OH | OH | $CH_3$ | H |
| $C_2H_5$ | H | —$CH_2$—$CH_2$—N⟨pyrrolidinyl⟩ | OH | OH | $CH_3$ | H |
| $C_2H_5$ | H | —$CH_2$—$CH_2$—N⟨morpholinyl⟩ | OH | OH | $CH_3$ | H |
| $C_2H_5$ | H | —$CH_2$—$CH_2$—N⟨piperidinyl⟩ | OH | OH | $CH_3$ | H |
| $C_2H_5$ | H | —$CH_2$—$CH_2$—N⟨N-methylpiperazinyl⟩ | OH | OH | $CH_3$ | H |
| $C_2H_5$ | $n$-$C_5H_{11}$ | $n$-$C_5H_{11}$ | OH | OH | $CH_3$ | H |
| $C_2H_5$ | $n$-$C_6H_{13}$ | $n$-$C_6H_{13}$ | OH | OH | $CH_3$ | H |
| $C_2H_5$ | $i$-$C_3H_7$ | $i$-$C_3H_7$ | OH | OH | $CH_3$ | H |
| $C_2H_5$ | $i$-$C_4H_9$ | $i$-$C_4H_9$ | OH | OH | $CH_3$ | H |
| $C_2H_5$ | $C_2H_4OH$ | $C_2H_4OH$ | OH | OH | $CH_3$ | H |
| $C_2H_5$ | —$CH_2$—CH—$CH_3$<br>         $\|$<br>        OH | —$CH_2$—CH—$CH_3$<br>         $\|$<br>        OH | OH | OH | $CH_3$ | H |
| $C_2H_5$ | —$CH_3$ | $C_2H_4OH$ | OH | OH | $CH_3$ | H |
| $C_2H_5$ | —$CH_2$—$CH_2$—$CH_2OH$ | —$CH_2$—$CH_2$—$CH_2OH$ | OH | OH | $CH_3$ | H |
| $C_2H_5$ | —$CH_2$—$C_6H_5$ | —$CH_2$—$C_6H_5$ | OH | OH | $CH_3$ | H |
| $C_2H_5$ | —$CH_2$—$CH_2$—$C_6H_5$ | —$CH_2$—$CH_2$—$C_6H_5$ | OH | OH | $CH_3$ | H |
| $C_2H_5$ | H | cyclopentyl | OH | OH | $CH_3$ | H |
| $C_2H_5$ | H | cyclohexyl | OH | OH | $CH_3$ | H |
| $C_2H_5$ | H | cycloheptyl | OH | OH | $CH_3$ | H |
| $C_2H_5$ | cyclohexyl-COOH | | OH | OH | $CH_3$ | H |
| $C_2H_5$ | cyclohexyl-$CH_2$-COOH | | OH | OH | $CH_3$ | H |
| $C_2H_5$ | cyclohexyl-$CH_2$-$CH_2$-COOH / cyclopentyl-COOH | | OH | OH | $CH_3$ | H |
| $C_2H_5$ | cyclopentyl(COOH)(OH) | | OH | OH | $CH_3$ | H |

TABLE IIB—continued

| R₁ | R₂ | R₃ | R₄ | R₅ | R₆ | R₇ |
|---|---|---|---|---|---|---|
| n-C₃H₇ | H | H | OH | OH | CH₃ | H |
| n-C₃H₇ | H | CH₃ | OH | OH | CH₃ | H |
| n-C₃H₇ | H | C₂H₅ | OH | OH | CH₃ | H |
| n-C₃H₇ | H | n-C₃H₇ | OH | OH | CH₃ | H |
| n-C₃H₇ | H | n-C₄H₉ | OH | OH | CH₃ | H |
| n-C₃H₇ | H | i-C₃H₇ | OH | OH | CH₃ | H |
| n-C₃H₇ | H | i-C₄H₉ | OH | OH | CH₃ | H |
| n-C₃H₇ | H | n-C₅H₁₁ | OH | OH | CH₃ | H |
| n-C₃H₇ | H | n-C₆H₁₃ | OH | OH | CH₃ | H |
| n-C₃H₇ | H | C₂H₄OH | OH | OH | CH₃ | H |
| n-C₃H₇ | H | —CH₂—CH(OH)—CH₃ | OH | OH | CH₃ | H |
| n-C₃H₇ | H | —CH₂—CH₂—CH₂OH | OH | OH | CH₃ | H |
| n-C₃H₇ | H | —CH₂—CH₂—N(CH₃)₂ | OH | OH | CH₃ | H |
| n-C₃H₇ | H | —CH₂—CH₂—N(C₂H₅)₂ | OH | OH | CH₃ | H |
| n-C₃H₇ | H | —CH₂—CH₂—N(C₄H₉)₂ | OH | OH | CH₃ | H |
| n-C₃H₇ | H | —CH₂—CH₂—CH₂—N(CH₃)₂ | OH | OH | CH₃ | H |
| n-C₃H₇ | H | —CH₂—CH₂—CH₂—N(C₂H₅)₂ | OH | OH | CH₃ | H |
| n-C₃H₇ | H | —CH₂—CON(CH₃)₂ | OH | OH | CH₃ | H |
| n-C₃H₇ | H | —CH₂—CH₂—CON(CH₃)₂ | OH | OH | CH₃ | H |
| n-C₃H₇ | H | —CH₂—CON(C₂H₅)₂ | OH | OH | CH₃ | H |
| n-C₃H₇ | H | —CH₂—C₆H₅ | OH | OH | CH₃ | H |
| n-C₃H₇ | H | —CH₂—CH₂—C₆H₅ | OH | OH | CH₃ | H |
| n-C₃H₇ | H | —CH₂—CH₂—N(pyrrolidinyl) | OH | OH | CH₃ | H |
| n-C₃H₇ | H | —CH₂—CH₂—N(morpholinyl) | OH | OH | CH₃ | H |
| n-C₃H₇ | H | —CH₂—CH₂—N(piperidinyl) | OH | OH | CH₃ | H |
| n-C₃H₇ | H | —CH₂—CH₂—N(N'-methylpiperazinyl) | OH | OH | CH₃ | H |
| n-C₃H₇ | n-C₅H₁₁ | n-C₅H₁₁ | OH | OH | CH₃ | H |
| n-C₃H₇ | n-C₆H₁₃ | n-C₆H₁₃ | OH | OH | CH₃ | H |
| n-C₃H₇ | i-C₃H₇ | i-C₃H₇ | OH | OH | CH₃ | H |
| n-C₃H₇ | i-C₄H₉ | i-C₄H₉ | OH | OH | CH₃ | H |
| n-C₃H₇ | C₂H₄OH | C₂H₄OH | OH | OH | CH₃ | H |
| n-C₃H₇ | —CH₂—CH(OH)—CH₃ | —CH₂—CH(OH)—CH₃ | OH | OH | CH₃ | H |
| n-C₃H₇ | —CH₃ | C₂H₄OH | OH | OH | CH₃ | H |
| n-C₃H₇ | —CH₂—CH₂—CH₂OH | —CH₂—CH₂—CH₂OH | OH | OH | CH₃ | H |
| n-C₃H₇ | —CH₂—C₆H₅ | —CH₂—C₆H₅ | OH | OH | CH₃ | H |
| n-C₃H₇ | —CH₂—CH₂—C₆H₅ | —CH₂—CH₂—C₆H₅ | OH | OH | CH₃ | H |
| n-C₃H₇ | H | cyclopentyl | OH | OH | CH₃ | H |
| n-C₃H₇ | H | cyclohexyl | OH | OH | CH₃ | H |
| n-C₃H₇ | H | cycloheptyl | OH | OH | CH₃ | H |
| n-C₃H₇ | H | cyclohexyl-COOH | OH | OH | CH₃ | H |
| n-C₃H₇ | H | cyclohexyl-CH₂-COOH | OH | OH | CH₃ | H |
| n-C₃H₇ | H | cyclohexyl-CH₂-CH₂-COOH | OH | OH | CH₃ | H |
| n-C₃H₇ | H | cyclopentyl-COOH | OH | OH | CH₃ | H |

TABLE IIB—continued

| R₁ | R₂ | R₃ | R₄ | R₅ | R₆ | R₇ |
|---|---|---|---|---|---|---|
| n-C₃H₇ | | 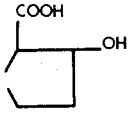 (cyclopentane with COOH and OH) | OH | OH | CH₃ | H |
| n-C₄H₉ | H | H | OH | OH | CH₃ | H |
| n-C₄H₉ | H | CH₃ | OH | OH | CH₃ | H |
| n-C₄H₉ | H | C₂H₅ | OH | OH | CH₃ | H |
| n-C₄H₉ | H | n-C₃H₇ | OH | OH | CH₃ | H |
| n-C₄H₉ | H | n-C₄H₉ | OH | OH | CH₃ | H |
| n-C₄H₉ | H | i-C₃H₇ | OH | OH | CH₃ | H |
| n-C₄H₉ | H | i-C₄H₉ | OH | OH | CH₃ | H |
| n-C₄H₉ | H | n-C₅H₁₁ | OH | OH | CH₃ | H |
| n-C₄H₉ | H | n-C₆H₁₃ | OH | OH | CH₃ | H |
| n-C₄H₉ | H | C₂H₄OH | OH | OH | CH₃ | H |
| n-C₄H₉ | H | —CH₂—CH(OH)—CH₃ | OH | OH | CH₃ | H |
| n-C₄H₉ | H | —CH₂—CH₂—CH₂OH | OH | OH | CH₃ | H |
| n-C₄H₉ | H | —CH₂—CH₂—N(CH₃)₂ | OH | OH | CH₃ | H |
| n-C₄H₉ | H | —CH₂—CH₂—N(C₂H₅)₂ | OH | OH | CH₃ | H |
| n-C₄H₉ | H | —CH₂—CH₂—N(C₄H₉)₂ | OH | OH | CH₃ | H |
| n-C₄H₉ | H | —CH₂—CH₂—CH₂—N(CH₃)₂ | OH | OH | CH₃ | H |
| n-C₄H₉ | H | —CH₂—CH₂—CH₂—N(C₂H₅)₂ | OH | OH | CH₃ | H |
| n-C₄H₉ | H | —CH₂—CON(CH₃)₂ | OH | OH | CH₃ | H |
| n-C₄H₉ | H | —CH₂—CH₂—CON(CH₃)₂ | OH | OH | CH₃ | H |
| n-C₄H₉ | H | —CH₂—CON(C₂H₅)₂ | OH | OH | CH₃ | H |
| n-C₄H₉ | H | —CH₂—C₆H₅ | OH | OH | CH₃ | H |
| n-C₄H₉ | H | —CH₂—CH₂—C₆H₅ | OH | OH | CH₃ | H |
| n-C₄H₉ | H | —CH₂—CH₂—N(pyrrolidinyl) 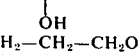 | OH | OH | CH₃ | H |
| n-C₄H₉ | H | —CH₂—CH₂—N(morpholinyl) 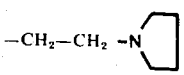 | H | OH | CH₃ | H |
| n-C₄H₉ | H | —CH₂—CH₂—N(piperidinyl) 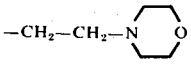 | OH | OH | CH₃ | H |
| n-C₄H₉ | H | —CH₂—CH₂—N(N-methylpiperazinyl) 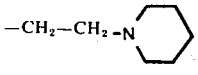 | OH | OH | CH₃ | H |
| n-C₄H₉ | n-C₅H₁₁ | n-C₅H₁₁ | OH | OH | CH₃ | H |
| n-C₄H₉ | n-C₆H₁₃ | n-C₆H₁₃ | OH | OH | CH₃ | H |
| n-C₄H₉ | i-C₃H₇ | i-C₃H₇ | OH | OH | CH₃ | H |
| n-C₄H₉ | i-C₄H₉ | i-C₄H₉ | OH | OH | CH₃ | H |
| n-C₄H₉ | C₂H₄OH | C₂H₄OH | OH | OH | CH₃ | H |
| n-C₄H₉ | —CH₂—CH(OH)—CH₃ | —CH₂—CH(OH)—CH₃ | OH | OH | CH₃ | H |
| n-C₄H₉ | —CH₃ | C₂H₄OH | OH | OH | CH₃ | H |
| n-C₄H₉ | —CH₂—CH₂—CH₂OH | —CH₂—CH₂—CH₂OH | OH | OH | CH₃ | H |
| n-C₄H₉ | —CH₂—C₆H₅ | —CH₂—C₆H₅ | OH | OH | CH₃ | H |
| n-C₄H₉ | —CH₂—CH₂—C₆H₅ | —CH₂—CH₂—C₆H₅ | OH | OH | CH₃ | H |
| n-C₄H₉ | H | 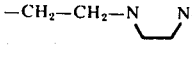 (cyclopentyl) | OH | OH | CH₃ | H |
| n-C₄H₉ | H |  (cyclohexyl) | OH | OH | CH₃ | H |
| n-C₄H₉ | H |  (cycloheptyl) | OH | OH | CH₃ | H |
| n-C₄H₉ | | 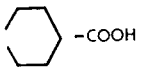 (cyclohexyl-COOH) | OH | OH | CH₃ | H |

TABLE IIB—continued

| R₁ | R₂ | R₃ | R₄ | R₅ | R₆ | R₇ |
|---|---|---|---|---|---|---|
| n-C₄H₉ | | ⌬-CH₂-COOH | OH | OH | CH₃ | H |
| n-C₄H₉ | | ⌬-CH₂-CH₂-COOH | OH | OH | CH₃ | H |
| n-C₄H₉ | | ⌬-COOH | OH | OH | CH₃ | H |
| n-C₄H₉ | | ⌬(COOH)(OH) | OH | OH | CH₃ | H |
| i-C₃H₇ | H | H | OH | OH | CH₃ | H |
| i-C₃H₇ | H | CH₃ | OH | OH | CH₃ | H |
| i-C₃H₇ | H | C₂H₅ | OH | OH | CH₃ | H |
| i-C₃H₇ | H | n-C₃H₇ | OH | OH | CH₃ | H |
| i-C₃H₇ | H | n-C₃H₉ | OH | OH | CH₃ | H |
| i-C₃H₇ | H | i-C₃H₇ | OH | OH | CH₃ | H |
| i-C₃H₇ | H | i-C₄H₉ | OH | OH | CH₃ | H |
| i-C₃H₇ | H | n-C₅H₁₁ | OH | OH | CH₃ | H |
| i-C₃H₇ | H | n-C₆H₁₃ | OH | OH | CH₃ | H |
| i-C₃H₇ | H | C₂H₄OH | OH | OH | CH₃ | H |
| i-C₃H₇ | H | —CH₂—CH(OH)—CH₃ | OH | OH | CH₃ | H |
| i-C₃H₇ | H | —CH₂—CH₂—CH₂OH | OH | OH | CH₃ | H |
| i-C₃H₇ | H | —CH₂—CH₂—N(CH₃)₂ | OH | OH | CH₃ | H |
| i-C₃H₇ | H | —CH₂—CH₂—N(C₂H₅)₂ | OH | OH | CH₃ | H |
| i-C₃H₇ | H | —CH₂—CH₂—N(C₄H₉)₂ | OH | OH | CH₃ | H |
| i-C₃H₇ | H | —CH₂—CH₂—CH₂—N(CH₃)₂ | OH | OH | CH₃ | H |
| i-C₃H₇ | H | —CH₂—CH₂—CH₂—N(C₂H₅)₂ | OH | OH | CH₃ | H |
| i-C₃H₇ | H | —CH₂—CON(CH₃)₂ | OH | OH | CH₃ | H |
| i-C₃H₇ | H | —CH₂—CH₂—CON(CH₃)₂ | OH | OH | CH₃ | H |
| i-C₃H₇ | H | —CH₂—CON(C₂H₅)₂ | OH | OH | CH₃ | H |
| i-C₃H₇ | H | —CH₂—C₆H₅ | OH | OH | CH₃ | H |
| i-C₃H₇ | H | —CH₂—CH₂—C₆H₅ | OH | OH | CH₃ | H |
| i-C₃H₇ | H | —CH₂—CH₂—N(pyrrolidinyl) | OH | OH | CH₃ | H |
| i-C₃H₇ | H | —CH₂—CH₂—N(morpholinyl) | OH | OH | CH₃ | H |
| i-C₃H₇ | H | —CH₂—CH₂—N(piperidinyl) | OH | OH | CH₃ | H |
| i-C₃H₇ | H | —CH₂—CH₂—N(N'-methylpiperazinyl) | OH | OH | CH₃ | H |
| i-C₃H₇ | n-C₅H₁₁ | n-C₅H₁₁ | OH | OH | CH₃ | H |
| i-C₃H₇ | n-C₆H₁₃ | n-C₆H₁₃ | OH | OH | CH₃ | H |
| i-C₃H₇ | i-C₃H₇ | i-C₃H₇ | OH | OH | CH₃ | H |
| i-C₃H₇ | i-C₄H₉ | i-C₄H₉ | OH | OH | CH₃ | H |
| i-C₃H₇ | CH₄OH | C₂H₄OH | OH | OH | CH₃ | H |
| i-C₃H₇ | —CH₂—CH(OH)—CH₃ | —CH₂—CH(OH)—CH₃ | OH | OH | CH₃ | H |
| i-C₃H₇ | —CH₃ | C₂H₄OH | OH | OH | CH₃ | H |
| i-C₃H₇ | —CH₂—CH₂—CH₂OH | —CH₂—CH₂—CH₂OH | OH | OH | CH₃ | H |
| i-C₃H₇ | —CH₂—C₆H₅ | —CH₂—C₆H₅ | OH | OH | CH₃ | H |
| i-C₃H₇ | —CH₂—CH₂—C₆H₅ | —CH₂—CH₂—C₆H₅ | OH | OH | CH₃ | H |
| i-C₃H₇ | H | cyclopentyl | OH | OH | CH₃ | H |
| i-C₃H₇ | H | cyclohexyl | OH | OH | CH₃ | H |

TABLE IIB—continued

| R₁ | R₂ | R₃ | R₄ | R₅ | R₆ | R₇ |
|---|---|---|---|---|---|---|
| i-C₃H₇ | H |  (cycloheptyl) | OH | OH | CH₃ | H |
| i-C₃H₇ | | 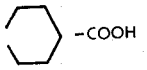 cyclohexyl-COOH | OH | OH | CH₃ | H |
| i-C₃H₇ | | 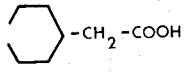 cyclohexyl-CH₂-COOH | OH | OH | CH₃ | H |
| i-C₃H₇ | | 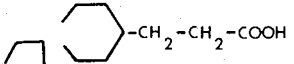 cyclohexyl-CH₂-CH₂-COOH | OH | OH | CH₃ | H |
| i-C₃H₇ | | 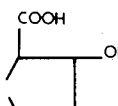 cyclopentyl-COOH | OH | OH | CH₃ | H |
| i-C₃H₇ | | 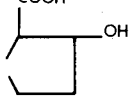 cyclopentyl-COOH, OH | OH | OH | CH₃ | H |
| i-C₄H₉ | H | H | OH | OH | CH₃ | H |
| i-C₄H₉ | H | CH₃ | OH | OH | CH₃ | H |
| i-C₄H₉ | H | C₂H₅ | OH | OH | CH₃ | H |
| i-C₄H₉ | H | n-C₃H₇ | OH | OH | CH₃ | H |
| i-C₄H₉ | H | n-C₄H₉ | OH | OH | CH₃ | H |
| i-C₄H₉ | H | i-C₃H₇ | OH | OH | CH₃ | H |
| i-C₄H₉ | H | i-C₄H₉ | OH | OH | CH₃ | H |
| i-C₄H₉ | H | n-C₅H₁₁ | OH | OH | CH₃ | H |
| i-C₄H₉ | H | n-C₆H₁₃ | OH | OH | CH₃ | H |
| i-C₄H₉ | H | C₂H₄OH | OH | OH | CH₃ | H |
| i-C₄H₉ | H | —CH₂—CH—CH₃ $\;$ OH | OH | OH | CH₃ | H |
| i-C₄H₉ | H | —CH₂—CH₂—CH₂OH | OH | OH | CH₃ | H |
| i-C₄H₉ | H | —CH₂—CH₂—N(CH₃)₂ | OH | OH | CH₃ | H |
| i-C₄H₉ | H | —CH₂—CH₂—N(C₂H₅)₂ | OH | OH | CH₃ | H |
| i-C₄H₉ | H | —CH₂—CH₂—N(C₄H₉)₂ | OH | OH | CH₃ | H |
| i-C₄H₉ | H | —CH₂—CH₂—CH₂—N(CH₃)₂ | OH | OH | CH₃ | H |
| i-C₄H₉ | H | —CH₂—CH₂—CH₂—N(C₂H₅)₂ | OH | OH | CH₃ | H |
| i-C₄H₉ | H | —CH₂—CON(CH₃)₂ | OH | OH | CH₃ | H |
| i-C₄H₉ | H | —CH₂—CH₂—CON(CH₃)₂ | OH | OH | CH₃ | H |
| i-C₄H₉ | H | —CH₂—CON(C₂H₅)₂ | OH | OH | CH₃ | H |
| i-C₄H₉ | H | —CH₂—C₆H₅ | OH | OH | CH₃ | H |
| i-C₄H₉ | H | —CH₂—CH₂—C₆H₅ | OH | OH | CH₃ | H |
| i-C₄H₉ | H | —CH₂—CH₂—N 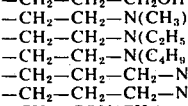 (pyrrolidinyl) | OH | OH | CH₃ | H |
| i-C₄H₉ | H | —CH₂—CH₂—N 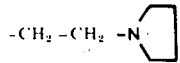 O (morpholinyl) | OH | OH | CH₃ | H |
| i-C₄H₉ | H | —CH₂—CH₂—N 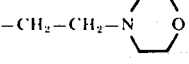 (piperidinyl) | OH | OH | CH₃ | H |
| i-C₄H₉ | H | —CH₂—CH₂—N 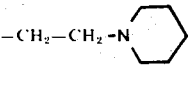 N—CH₃ (N-methylpiperazinyl) | OH | OH | CH₃ | H |
| i-C₄H₉ | n-C₅H₁₁ | n-C₅H₁₁ | OH | OH | CH₃ | H |
| i-C₄H₉ | n-C₆H₁₃ | n-C₆H₁₃ | OH | OH | CH₃ | H |
| i-C₄H₉ | i-C₃H₇ | i-C₃H₇ | OH | OH | CH₃ | H |
| i-C₄H₉ | i-C₄H₉ | i-C₄H₉ | OH | OH | CH₃ | H |
| i-C₄H₉ | C₂H₄OH | C₂H₄OH | OH | OH | CH₃ | H |
| i-C₄H₉ | —CH₂—CH—CH₃ $\;$ OH | —CH₂—CH—CH₃ $\;$ OH | OH | OH | CH₃ | H |
| i-C₄H₉ | —CH₃ | C₂H₄OH | OH | OH | CH₃ | H |
| i-C₄H₉ | —CH₂—CH₂—CH₂OH | —CH₂—CH₂—CH₂OH | OH | OH | CH₃ | H |
| i-C₄H₉ | —CH₂—C₆H₅ | —CH₂—C₆H₅ | OH | OH | CH₃ | H |
| i-C₄H₉ | —CH₂—CH₂—C₆H₅ | —CH₂—CH₂—C₆H₅ | OH | OH | CH₃ | H |

TABLE IIB—continued

| R₁ | R₂ | R₃ | R₄ | R₅ | R₆ | R₇ |
|---|---|---|---|---|---|---|
| i-C₄H₉ | H |  | OH | OH | CH₃ | H |
| i-C₄H₉ | H |  | OH | OH | CH₃ | H |
| i-C₄H₉ | H |  | OH | OH | CH₃ | H |
| i-C₄H₉ | | 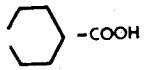 | OH | OH | CH₃ | H |
| i-C₄H₉ | | 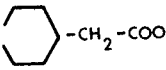 –COOH | OH | OH | CH₃ | H |
| i-C₄H₉ | | 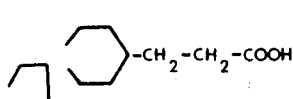 –CH₂–COOH | OH | OH | CH₃ | H |
| i-C₄H₉ | | 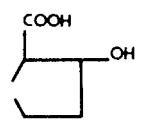 –CH₂–CH₂–COOH | OH | OH | CH₃ | H |
| i-C₄H₉ | | 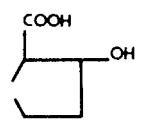 COOH | OH | OH | CH₃ | H |
| i-C₄H₉ | |  | OH | OH | CH₃ | H |
| sec.-C₄H₉ | H | H | OH | OH | CH₃ | H |
| sec.-C₄H₉ | H | CH₃ | OH | OH | CH₃ | H |
| sec.-C₄H₉ | H | C₂H₅ | OH | OH | CH₃ | H |
| sec.-C₄H₉ | H | n-C₃H₇ | OH | OH | CH₃ | H |
| sec.-C₄H₉ | H | n-C₄H₉ | OH | OH | CH₃ | H |
| sec.-C₄H₉ | H | i-C₃H₇ | OH | OH | CH₃ | H |
| sec.-C₄H₉ | H | i-C₄H₉ | OH | OH | CH₃ | H |
| sec.-C₄H₉ | H | n-C₅H₁₁ | OH | OH | CH₃ | H |
| sec.-C₄H₉ | H | n-C₆H₁₃ | OH | OH | CH₃ | H |
| sec.-C₄H₉ | H | C₂H₄OH | OH | OH | CH₃ | H |
| sec.-C₄H₉ | H | –CH₂–CH(OH)–CH₃ | OH | OH | CH₃ | H |
| sec.-C₄H₉ | H | –CH₂–CH₂–CH₂OH | OH | OH | CH₃ | H |
| sec.-C₄H₉ | H | –CH₂–CH₂–N(CH₃)₂ | OH | OH | CH₃ | H |
| sec.-C₄H₉ | H | –CH₂–CH₂–N(C₂H₅)₂ | OH | OH | CH₃ | H |
| sec.-C₄H₉ | H | –CH₂–CH₂–N(C₄H₉)₂ | OH | OH | CH₃ | H |
| sec.-C₄H₉ | H | –CH₂–CH₂–CH₂–N(CH₃)₂ | OH | OH | CH₃ | H |
| sec.-C₄H₉ | H | –CH₂–CH₂–CH₂–N(C₂H₅)₂ | OH | OH | CH₃ | H |
| sec.-C₄H₉ | H | –CH₂–CON(CH₃)₂ | OH | OH | CH₃ | H |
| sec.-C₄H₉ | H | –CH₂–CH₂–CON(CH₃)₂ | OH | OH | CH₃ | H |
| sec.-C₄H₉ | H | –CH₂–CON(C₂H₅)₂ | OH | OH | CH₃ | H |
| sec.-C₄H₉ | H | –CH₂–C₆H₅ | OH | OH | CH₃ | H |
| sec.-C₄H₉ | H | –CH₂–CH₂–C₆H₅ | OH | OH | CH₃ | H |
| sec.-C₄H₉ | H | –CH₂–CH₂–N | OH | OH | CH₃ | H |
| sec.-C₄H₉ | H | –CH₂–CH₂–NO | OH | OH | CH₃ | H |
| sec.-C₄H₉ | H | –CH₂–CH₂–N | OH | OH | CH₃ | H |
| sec.-C₄H₉ | H | –CH₂–CH₂–NN–CH₃ | OH | OH | CH₃ | H |
| sec.-C₄H₉ | n-C₅H₁₁ | n-C₅H₁₁ | OH | OH | CH₃ | H |
| sec.-C₄H₉ | n-C₆H₁₃ | n-C₆H₁₃ | OH | OH | CH₃ | H |
| sec.-C₄H₉ | i-C₃H₇ | i-C₃H₇ | OH | OH | CH₃ | H |
| sec.-C₄H₉ | i-C₄H₉ | i-C₄H₉ | OH | OH | CH₃ | H |

TABLE IIB—continued

| R₁ | R₂ | R₃ | R₄ | R₅ | R₆ | R₇ |
|---|---|---|---|---|---|---|
| sec.-C₄H₉ | C₂H₄OH | C₂H₄OH | OH | OH | CH₃ | H |
| sec.-C₄H₉ | —CH₂—CH—CH₃ <br>            OH | —CH₂—CH—CH₃ <br>            OH | OH | OH | CH₃ | H |
| sec.-C₄H₉ | —CH₃ | C₂H₄OH | OH | OH | CH₃ | H |
| sec.-C₄H₉ | —CH₂—CH₂—CH₂OH | —CH₂—CH₂—CH₂OH | OH | OH | CH₃ | H |
| sec.-C₄H₉ | —CH₂—C₆H₅ | —CH₂—C₆H₅ | OH | OH | CH₃ | H |
| sec.-C₄H₉ | —CH₂—CH₂—C₆H₅ | —CH₂—CH₂—C₆H₅ | OH | OH | CH₃ | H |
| sec.-C₄H₉ | H | cyclopentyl | OH | OH | CH₃ | H |
| sec.-C₄H₉ | H | cyclohexyl | OH | OH | CH₃ | H |
| sec.-C₄H₉ | H | cycloheptyl | OH | OH | CH₃ | H |
| sec.-C₄H₉ | | cyclohexyl-COOH | OH | OH | CH₃ | H |
| sec.-C₄H₉ | | cyclohexyl-CH₂-COOH | OH | OH | CH₃ | H |
| sec.-C₄H₉ | | cyclohexyl-CH₂-CH₂-COOH | OH | OH | CH₃ | H |
| sec.-C₄H₉ | | cyclopentyl-COOH | OH | OH | CH₃ | H |
| sec.-C₄H₉ | | cyclohexyl(COOH)(OH) | OH | OH | CH₃ | H |

TABLE IIIA

| R₁ | R₂ | R₃ | R₄ | R₅ | R₆ | R₇ |
|---|---|---|---|---|---|---|
| CH₃ | CH₃ | CH₃ | H | OH | CH₃ | Cl |
| CH₃ | CH₃ | C₂H₅ | H | OH | CH₃ | Cl |
| CH₃ | C₂H₅ | C₂H₅ | H | OH | CH₃ | Cl |
| CH₃ | n-C₃H₇ | n-C₃H₇ | H | OH | CH₃ | Cl |
| CH₃ | n-C₄H₉ | n-C₄H₉ | H | OH | CH₃ | Cl |
| CH₃ | H | CH₂—COOH | H | OH | CH₃ | Cl |
| CH₃ | H | CH₂—COOC₂H₅ | H | OH | CH₃ | Cl |
| CH₃ | H | CH₃—CH—COOH | H | OH | CH₃ | Cl |
| CH₃ | H | CH₃—CH—COOC₂H₅ | H | OH | CH₃ | Cl |
| CH₃ | H | —CH₂—CH₂—COOH | H | OH | CH₃ | Cl |
| CH₃ | H | —CH₂—CH₂—COOC₂H₅ | H | OH | CH₃ | Cl |
| CH₃ | H | —(CH₂)₄—CH(NH₂)—COOH | H | OH | CH₃ | Cl |
| CH₃ | cyclopentyl | | H | OH | CH₃ | Cl |
| CH₃ | cyclohexyl | | H | OH | CH₃ | Cl |
| CH₃ | tetrahydropyranyl (O) | | H | OH | CH₃ | Cl |
| CH₃ | piperidinyl (N) | | H | OH | CH₃ | Cl |
| CH₃ | N-methylpiperazinyl | | H | OH | CH₃ | Cl |
| CH₃ | N-ethylpiperazinyl | | H | OH | CH₃ | Cl |
| CH₃ | N-(2-hydroxyethyl)piperazinyl | | H | OH | CH₃ | Cl |
| C₂H₅ | CH₃ | CH₃ | H | OH | CH₃ | Cl |
| C₂H₅ | CH₃ | C₂H₅ | H | OH | CH₃ | Cl |
| C₂H₅ | C₂H₅ | C₂H₅ | H | OH | CH₃ | Cl |
| C₂H₅ | n-C₃H₇ | n-C₃H₇ | H | OH | CH₃ | Cl |
| C₂H₅ | n-C₄H₉ | n-C₄H₉ | H | OH | CH₃ | Cl |
| C₂H₅ | H | CH₂—COOH | H | OH | CH₃ | Cl |
| C₂H₅ | H | CH₂—COOC₂H₅ | H | OH | CH₃ | Cl |
| C₂H₅ | H | CH₃—CH—COOH | H | OH | CH₃ | Cl |
| C₂H₅ | H | CH₃—CH—COOC₂H₅ | H | OH | CH₃ | Cl |

TABLE IIIA-continued

| R₁ | R₂ | R₃ | R₄ | R₅ | R₆ | R₇ |
|---|---|---|---|---|---|---|
| C₂H₅ | H | —CH₂—CH₂—COOH | H | OH | CH₃ | Cl |
| C₂H₅ | H | —CH₂—CH₂—COOC₂H₅ | H | OH | CH₃ | Cl |
| C₂H₅ | H | —(CH₂)₄—CH(NH₂)—COOH | H | OH | CH₃ | Cl |
| C₂H₅ | pyrrolidino | | H | OH | CH₃ | Cl |
| C₂H₅ | piperidino | | H | OH | CH₃ | Cl |
| C₂H₅ | morpholino | | H | OH | CH₃ | Cl |
| C₂H₅ | piperazino | | H | OH | CH₃ | Cl |
| C₂H₅ | N-methylpiperazino | | H | OH | CH₃ | Cl |
| C₂H₅ | N-ethylpiperazino | | H | OH | CH₃ | Cl |
| C₂H₅ | N-(2-hydroxyethyl)piperazino | | H | OH | CH₃ | Cl |
| n-C₃H₇ | CH₃ | CH₃ | H | OH | CH₃ | Cl |
| n-C₃H₇ | CH₃ | C₂H₅ | H | OH | CH₃ | Cl |
| n-C₃H₇ | C₂H₅ | C₂H₅ | H | OH | CH₃ | Cl |
| n-C₃H₇ | n-C₃H₇ | n-C₃H₇ | H | OH | CH₃ | Cl |
| n-C₃H₇ | n-C₄H₉ | n-C₄H₉ | H | OH | CH₃ | Cl |
| n-C₃H₇ | H | CH₂—COOH | H | OH | CH₃ | Cl |
| n-C₃H₇ | H | CH₂—COOC₂H₅ | H | OH | CH₃ | Cl |
| n-C₃H₇ | H | CH₃—CH—COOH | H | OH | CH₃ | Cl |
| n-C₃H₇ | H | CH₃—CH—COOC₂H₅ | H | OH | CH₃ | Cl |
| n-C₃H₇ | H | —CH₂—CH₂—COOH | H | OH | CH₃ | Cl |
| n-C₃H₇ | H | —CH₂—CH₂—COOC₂H₅ | H | OH | CH₃ | Cl |
| n-C₃H₇ | H | —(CH₂)₄—CH(NH₂)—COOH | H | OH | CH₃ | Cl |
| n-C₃H₇ | pyrrolidino | | H | OH | CH₃ | Cl |
| n-C₃H₇ | piperidino | | H | OH | CH₃ | Cl |
| n-C₃H₇ | morpholino | | H | OH | CH₃ | Cl |
| n-C₃H₇ | piperazino | | H | OH | CH₃ | Cl |
| n-C₃H₇ | N-methylpiperazino | | H | OH | CH₃ | Cl |
| n-C₃H₇ | N-ethylpiperazino | | H | OH | CH₃ | Cl |
| n-C₃H₇ | N-(2-hydroxyethyl)piperazino | | H | OH | CH₃ | Cl |
| n-C₄H₉ | CH₃ | CH₃ | H | OH | CH₃ | Cl |
| n-C₄H₉ | CH₃ | C₂H₅ | H | OH | CH₃ | Cl |
| n-C₄H₉ | C₂H₅ | C₂H₅ | H | OH | CH₃ | Cl |
| n-C₄H₉ | n-C₃H₇ | n-C₃H₇ | H | OH | CH₃ | Cl |
| n-C₄H₉ | n-C₄H₉ | n-C₄H₉ | H | OH | CH₃ | Cl |
| n-C₄H₉ | H | CH₂—COOH | H | OH | CH₃ | Cl |
| n-C₄H₉ | H | CH₂—COOC₂H₅ | H | OH | CH₃ | Cl |
| n-C₄H₉ | H | CH₃—CH—COOH | H | OH | CH₃ | Cl |
| n-C₄H₉ | H | CH₃—CH—COOC₂H₅ | H | OH | CH₃ | Cl |
| n-C₄H₉ | H | —CH₂—CH₂—COOH | H | OH | CH₃ | Cl |
| n-C₄H₉ | H | —CH₂—CH₂—COOC₂H₅ | H | OH | CH₃ | Cl |
| n-C₄H₉ | H | —(CH₂)₄—CH(NH₂)—COOH | H | OH | CH₃ | Cl |
| n-C₄H₉ | pyrrolidino | | H | OH | CH₃ | Cl |
| n-C₄H₉ | piperidino | | H | OH | CH₃ | Cl |
| n-C₄H₉ | morpholino | | H | OH | CH₃ | Cl |
| n-C₄H₉ | piperazino | | H | OH | CH₃ | Cl |
| n-C₄H₉ | N-methylpiperazino | | H | OH | CH₃ | Cl |
| n-C₄H₉ | N-ethylpiperazino | | H | OH | CH₃ | Cl |
| n-C₄H₉ | N-(2-hydroxyethyl)piperazino | | H | OH | CH₃ | Cl |

TABLE IIIB

| R₁ | R₂ | R₃ | R₄ | R₅ | R₆ | R₇ |
|---|---|---|---|---|---|---|
| CH₃ | H | H | H | OH | CH₃ | Cl |
| CH₃ | H | CH₃ | H | OH | CH₃ | Cl |
| CH₃ | H | C₂H₅ | H | OH | CH₃ | Cl |
| CH₃ | H | n-C₃H₇ | H | OH | CH₃ | Cl |
| CH₃ | H | n-C₄H₉ | H | OH | CH₃ | Cl |
| CH₃ | H | i-C₃H₇ | H | OH | CH₃ | Cl |
| CH₃ | H | i-C₄H₉ | H | OH | CH₃ | Cl |
| CH₃ | H | n-C₅H₁₁ | H | OH | CH₃ | Cl |
| CH₃ | H | n-C₆H₁₃ | H | OH | CH₃ | Cl |
| CH₃ | H | C₂H₄OH | H | OH | CH₃ | Cl |
| CH₃ | H | —CH₂—CH(OH)—CH₃ | H | OH | CH₃ | Cl |
| CH₃ | H | —CH₂—CH₂—CH₂OH | H | OH | CH₃ | Cl |

TABLE IIIB-continued

| R₁ | R₂ | R₃ | R₄ | R₅ | R₆ | R₇ |
|---|---|---|---|---|---|---|
| CH₃ | H | —CH₂—CH₂—N(CH₃)₂ | H | OH | CH₃ | Cl |
| CH₃ | H | —CH₂—CH₂—N(C₂H₅)₂ | H | OH | CH₃ | Cl |
| CH₃ | H | —CH₂—CH₂—N(C₄H₉)₂ | H | OH | CH₃ | Cl |
| CH₃ | H | —CH₂—CH₂—CH₂—N(CH₃)₂ | H | OH | CH₃ | Cl |
| CH₃ | H | —CH₂—CH₂—CH₂—N(C₂H₅)₂ | H | OH | CH₃ | Cl |
| CH₃ | H | —CH₂—CON(CH₃)₂ | H | OH | CH₃ | Cl |
| CH₃ | H | —CH₂—CH₂—CON(CH₃)₂ | H | OH | CH₃ | Cl |
| CH₃ | H | —CH₂—CON(C₂H₅)₂ | H | OH | CH₃ | Cl |
| CH₃ | H | —CH₂—C₆H₅ | H | OH | CH₃ | Cl |
| CH₃ | H | —CH₂—CH₂—C₆H₅ | H | OH | CH₃ | Cl |
| CH₃ | H | 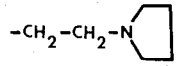 | H | OH | CH₃ | Cl |
| CH₃ | H | 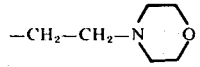 | H | OH | CH₃ | Cl |
| CH₃ | H | 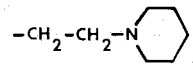 | H | OH | CH₃ | Cl |
| CH₃ | H | 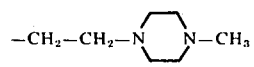 | H | OH | CH₃ | Cl |
| CH₃ | n-C₅H₁₁ | n-C₅H₁₁ | H | OH | CH₃ | Cl |
| CH₃ | n-C₆H₁₃ | n-C₆H₁₃ | H | OH | CH₃ | Cl |
| CH₃ | i-C₃H₇ | i-C₃H₇ | H | OH | CH₃ | Cl |
| CH₃ | i-C₄H₉ | i-C₄H₉ | H | OH | CH₃ | Cl |
| CH₃ | C₂H₄OH | C₂H₄OH | H | OH | CH₃ | Cl |
| CH₃ | —CH₂—CH(OH)—CH₃ | —CH₂—CH(OH)—CH₃ | H | OH | CH₃ | Cl |
| CH₃ | —CH₃ | C₂H₄OH | H | OH | CH₃ | Cl |
| CH₃ | —CH₂—CH₂—CH₂OH | —CH₂—CH₂—CH₂OH | H | OH | CH₃ | Cl |
| CH₃ | —CH₂—C₆H₅ | —CH₂—C₆H₅ | H | OH | CH₃ | Cl |
| CH₃ | —CH₂—CH₂—C₆H₅ | —CH₂—CH₂—C₆H₅ | H | OH | CH₃ | Cl |
| CH₃ | H |  | H | OH | CH₃ | Cl |
| CH₃ | H |  | H | OH | CH₃ | Cl |
| CH₃ | H |  | H | OH | CH₃ | Cl |
| CH₃ | 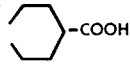 | | H | OH | CH₃ | Cl |
| CH₃ | 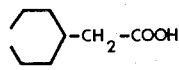 | | H | OH | CH₃ | Cl |
| CH₃ | 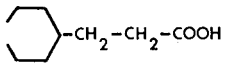 | | H | OH | CH₃ | Cl |
| CH₃ |  | | H | OH | CH₃ | Cl |
| CH₃ | | 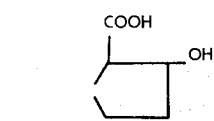 | H | OH | CH₃ | Cl |
| C₂H₅ | H | H | H | OH | CH₃ | Cl |
| C₂H₅ | H | CH₃ | H | OH | CH₃ | Cl |
| C₂H₅ | H | C₂H₅ | H | OH | CH₃ | Cl |

TABLE IIIB-continued

| R₁ | R₂ | R₃ | R₄ | R₅ | R₆ | R₇ |
|---|---|---|---|---|---|---|
| C₂H₅ | H | n-C₃H₇ | H | OH | CH₃ | Cl |
| C₂H₅ | H | n-C₄H₉ | H | OH | CH₃ | Cl |
| C₂H₅ | H | i-C₃H₇ | H | OH | CH₃ | Cl |
| C₂H₅ | H | i-C₄H₉ | H | OH | CH₃ | Cl |
| C₂H₅ | H | n-C₅H₁₁ | H | OH | CH₃ | Cl |
| C₂H₅ | H | n-C₆H₁₃ | H | OH | CH₃ | Cl |
| C₂H₅ | H | C₂H₄OH | H | OH | CH₃ | Cl |
| C₂H₅ | H | —CH₂—CH—CH₃<br>        \|<br>        OH | H | OH | CH₃ | Cl |
| C₂H₅ | H | —CH₂—CH₂—CH₂OH | H | OH | CH₃ | Cl |
| C₂H₅ | H | —CH₂—CH₂—N(CH₃)₂ | H | OH | CH₃ | Cl |
| C₂H₅ | H | —CH₂—CH₂—N(C₂H₅)₂ | H | OH | CH₃ | Cl |
| C₂H₅ | H | —CH₂—CH₂—N(C₄H₉)₂ | H | OH | CH₃ | Cl |
| C₂H₅ | H | —CH₂—CH₂—CH₂—N(CH₃)₂ | H | OH | CH₃ | Cl |
| C₂H₅ | H | —CH₂—CH₂—CH₂—N(C₂H₅)₂ | H | OH | CH₃ | Cl |
| C₂H₅ | H | —CH₂—CON(CH₃)₂ | H | OH | CH₃ | Cl |
| C₂H₅ | H | —CH₂—CH₂—CON(CH₃)₂ | H | OH | CH₃ | Cl |
| C₂H₅ | H | —CH₂—CON(C₂H₅)₂ | H | OH | CH₃ | Cl |
| C₂H₅ | H | —CH₂—C₆H₅ | H | OH | CH₃ | Cl |
| C₂H₅ | H | —CH₂—CH₂—C₆H₅ | H | OH | CH₃ | Cl |
| C₂H₅ | H | —CH₂—CH₂—N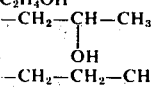 | H | OH | CH₃ | Cl |
| C₂H₅ | H | —CH₂—CH₂—N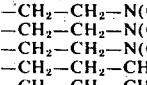O | H | OH | CH₃ | |
| C₂H₅ | H | —CH₂—CH₂—N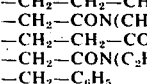 | H | OH | CH₃ | |
| C₂H₅ | H | —CH₂—CH₂—N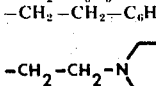N—CH₃ | H | OH | CH₃ | |
| C₂H₅ | n-C₅H₁₁ | n-C₅H₁₁ | H | OH | CH₃ | |
| C₂H₅ | n-C₆H₁₃ | n-C₆H₁₃ | H | OH | CH₃ | |
| C₂H₅ | i-C₃H₇ | i-C₃H₇ | H | OH | CH₃ | |
| C₂H₅ | i-C₄H₉ | i-C₄H₉ | H | OH | CH₃ | |
| C₂H₅ | C₂H₄OH | C₂H₄OH | H | OH | CH₃ | |
| C₂H₅ | —CH₂—CH—CH₃<br>        \|<br>        OH | —CH₂—CH—CH₃<br>        \|<br>        OH | H | OH | CH₃ | |
| C₂H₅ | —CH₃ | C₂H₄OH | H | OH | CH₃ | |
| C₂H₅ | —CH₂—CH₂—CH₂OH | —CH₂—CH₂—CH₂OH | H | OH | CH₃ | |
| C₂H₅ | —CH₂—C₆H₅ | —CH₂—C₆H₅ | H | OH | CH₃ | Cl |
| C₂H₅ | —CH₂—CH₂—C₆H₅ | —CH₂—CH₂—C₆H₅ | H | OH | CH₃ | Cl |
| C₂H₅ | H | 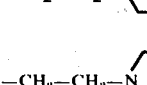 | H | OH | CH₃ | Cl |
| C₂H₅ | H | 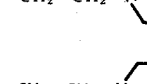 | H | OH | CH₃ | Cl |
| C₂H₅ | H | 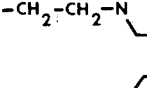 | H | OH | CH₃ | Cl |
| C₂H₅ | H | 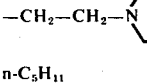—COOH | H | OH | CH₃ | Cl |
| C₂H₅ | H | 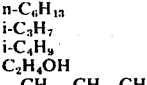—CH₂—COOH | H | OH | CH₃ | Cl |
| C₂H₅ | H | 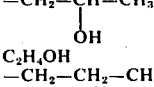—CH₂—CH₂—COOH | H | OH | CH₃ | Cl |
| C₂H₅ | 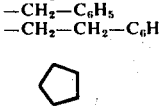<br>COOH | | H | OH | CH₃ | Cl |

TABLE IIIB-continued

| R₁ | R₂ | R₃ | R₄ | R₅ | R₆ | R₇ |
|---|---|---|---|---|---|---|
| $C_2H_5$ | COOH | (cyclopentane-OH) | H | OH | $CH_3$ | Cl |
| n-$C_3H_7$ | H | H | H | OH | $CH_3$ | Cl |
| n-$C_3H_7$ | H | $CH_3$ | H | OH | $CH_3$ | Cl |
| n-$C_3H_7$ | H | $C_2H_5$ | H | OH | $CH_3$ | Cl |
| n-$C_3H_7$ | H | n-$C_3H_7$ | H | OH | $CH_3$ | Cl |
| n-$C_3H_7$ | H | n-$C_4H_9$ | H | OH | $CH_3$ | Cl |
| n-$C_3H_7$ | H | i-$C_3H_7$ | H | OH | $CH_3$ | Cl |
| n-$C_3H_7$ | H | i-$C_4H_9$ | H | OH | $CH_3$ | Cl |
| n-$C_3H_7$ | H | n-$C_5H_{11}$ | H | OH | $CH_3$ | Cl |
| n-$C_3H_7$ | H | n-$C_6H_{13}$ | H | OH | $CH_3$ | Cl |
| n-$C_3H_7$ | H | $C_2H_4OH$ | H | OH | $CH_3$ | Cl |
| n-$C_3H_7$ | H | $-CH_2-CH(OH)-CH_3$ | H | OH | $CH_3$ | Cl |
| n-$C_3H_7$ | H | $-CH_2-CH_2-CH_2OH$ | H | OH | $CH_3$ | Cl |
| n-$C_3H_7$ | H | $-CH_2-CH_2-N(CH_3)_2$ | H | OH | $CH_3$ | Cl |
| n-$C_3H_7$ | H | $-CH_2-CH_2-N(C_2H_5)_2$ | H | OH | $CH_3$ | Cl |
| n-$C_3H_7$ | H | $-CH_2-CH_2-N(C_4H_9)_2$ | H | OH | $CH_3$ | Cl |
| n-$C_3H_7$ | H | $-CH_2-CH_2-CH_2-N(CH_3)_2$ | H | OH | $CH_3$ | Cl |
| n-$C_3H_7$ | H | $-CH_2-CH_2-CH_2-N(C_2H_5)_2$ | H | OH | $CH_3$ | Cl |
| n-$C_3H_7$ | H | $-CH_2-CON(CH_3)_2$ | H | OH | $CH_3$ | Cl |
| n-$C_3H_7$ | H | $-CH_2-CH_2-CON(CH_3)_2$ | H | OH | $CH_3$ | Cl |
| n-$C_3H_7$ | H | $-CH_2-CON(C_2H_5)_2$ | H | OH | $CH_3$ | Cl |
| n-$C_3H_7$ | H | $-CH_2-C_6H_5$ | H | OH | $CH_3$ | Cl |
| n-$C_3H_7$ | H | $-CH_2-CH_2-C_6H_5$ | H | OH | $CH_3$ | Cl |
| n-$C_3H_7$ | H | $-CH_2-CH_2-$(pyrrolidinyl) | H | OH | $CH_3$ | Cl |
| n-$C_3H_7$ | H | $-CH_2-CH_2-$(morpholinyl) | H | OH | $CH_3$ | Cl |
| n-$C_3H_7$ | H | $-CH_2-CH_2-$(piperidinyl) | H | OH | $CH_3$ | Cl |
| n-$C_3H_7$ | H | $-CH_2-CH_2-$(4-methylpiperazinyl) | H | OH | $CH_3$ | Cl |
| n-$C_3H_7$ | n-$C_5H_{11}$ | n-$C_5H_{11}$ | H | OH | $CH_3$ | Cl |
| n-$C_3H_7$ | n-$C_6H_{13}$ | n-$C_6H_{13}$ | H | OH | $CH_3$ | Cl |
| n-$C_3H_7$ | i-$C_3H_7$ | i-$C_3H_7$ | H | OH | $CH_3$ | Cl |
| n-$C_3H_7$ | i-$C_4H_9$ | i-$C_4H_9$ | H | OH | $CH_3$ | Cl |
| n-$C_3H_7$ | $C_2H_4OH$ | $C_2H_4OH$ | H | OH | $CH_3$ | Cl |
| n-$C_3H_7$ | $-CH_2-CH(OH)-CH_3$ | $-CH_2-CH(OH)-CH_3$ | H | OH | $CH_3$ | Cl |
| n-$C_3H_7$ | $-CH_3$ | $C_2H_4OH$ | H | OH | $CH_3$ | Cl |
| n-$C_3H_7$ | $-CH_2-CH_2-CH_2OH$ | $-CH_2-CH_2-CH_2OH$ | H | OH | $CH_3$ | Cl |
| n-$C_3H_7$ | $-CH_2-C_6H_5$ | $-CH_2-C_6H_5$ | H | OH | $CH_3$ | Cl |
| n-$C_3H_7$ | $-CH_2-CH_2-C_6H_5$ | $-CH_2-CH_2-C_6H_5$ | H | OH | $CH_3$ | Cl |
| n-$C_3H_7$ | H | cyclopentyl | H | OH | $CH_3$ | Cl |
| n-$C_3H_7$ | H | cyclohexyl | H | OH | $CH_3$ | Cl |
| n-$C_3H_7$ | H | cycloheptyl | H | OH | $CH_3$ | Cl |
| n-$C_3H_7$ | cyclohexyl-COOH | | H | OH | $CH_3$ | Cl |
| n-$C_3H_7$ | cyclohexyl-$CH_2$-COOH | | H | OH | $CH_3$ | Cl |

TABLE IIIB-continued

| $R_1$ | $R_2$ | $R_3$ | $R_4$ | $R_5$ | $R_6$ | $R_7$ |
|---|---|---|---|---|---|---|
| n-$C_3H_7$ |  | cyclohexyl-$CH_2$-$CH_2$-COOH | H | OH | $CH_3$ | Cl |
| n-$C_3H_7$ | cyclopentyl-COOH |  | H | OH | $CH_3$ | Cl |
| n-$C_3H_7$ |  | cyclopentyl(COOH)(OH) | H | OH | $CH_3$ | Cl |
| n-$C_4H_9$ | H | H | H | OH | $CH_3$ | Cl |
| n-$C_4H_9$ | H | $CH_3$ | H | OH | $CH_3$ | Cl |
| n-$C_4H_9$ | H | $C_2H_5$ | H | OH | $CH_3$ | Cl |
| n-$C_4H_9$ | H | n-$C_3H_7$ | H | OH | $CH_3$ | Cl |
| n-$C_4H_9$ | H | n-$C_4H_9$ | H | OH | $CH_3$ | Cl |
| n-$C_4H_9$ | H | i-$C_3H_7$ | H | OH | $CH_3$ | Cl |
| n-$C_4H_9$ | H | i-$C_4H_9$ | H | OH | $CH_3$ | Cl |
| n-$C_4H_9$ | H | n-$C_5H_{11}$ | H | OH | $CH_3$ | Cl |
| n-$C_4H_9$ | H | n-$C_6H_{13}$ | H | OH | $CH_3$ | Cl |
| n-$C_4H_9$ | H | $C_2H_4OH$ | H | OH | $CH_3$ | Cl |
| n-$C_4H_9$ | H | $-CH_2-CH(OH)-CH_3$ | H | OH | $CH_3$ | Cl |
| n-$C_4H_9$ | H | $-CH_2-CH_2-CH_2OH$ | H | OH | $CH_3$ | Cl |
| n-$C_4H_9$ | H | $-CH_2-CH_2-N(CH_3)_2$ | H | OH | $CH_3$ | Cl |
| n-$C_4H_9$ | H | $-CH_2-CH_2-N(C_2H_5)_2$ | H | OH | $CH_3$ | Cl |
| n-$C_4H_9$ | H | $-CH_2-CH_2-N(C_4H_9)_2$ | H | OH | $CH_3$ | Cl |
| n-$C_4H_9$ | H | $-CH_2-CH_2-CH_2-N(CH_3)_2$ | H | OH | $CH_3$ | Cl |
| n-$C_4H_9$ | H | $-CH_2-CH_2-CH_2-N(C_2H_5)_2$ | H | OH | $CH_3$ | Cl |
| n-$C_4H_9$ | H | $-CH_2-CON(CH_3)_2$ | H | OH | $CH_3$ | Cl |
| n-$C_4H_9$ | H | $-CH_2-CH_2-CON(CH_3)_2$ | H | OH | $CH_3$ | Cl |
| n-$C_4H_9$ | H | $-CH_2-CON(C_2H_5)_2$ | H | OH | $CH_3$ | Cl |
| n-$C_4H_9$ | H | $-CH_2-C_6H_5$ | H | OH | $CH_3$ | Cl |
| n-$C_4H_9$ | H | $-CH_2-CH_2-C_6H_5$ | H | OH | $CH_3$ | Cl |
| n-$C_4H_9$ | H | $-CH_2-CH_2-$N-pyrrolidinyl | H | OH | $CH_3$ | Cl |
| n-$C_4H_9$ | H | $-CH_2-CH_2-$N-morpholinyl | H | OH | $CH_3$ | Cl |
| n-$C_4H_9$ | H | $-CH_2-CH_2-$N-piperidinyl | H | OH | $CH_3$ | Cl |
| n-$C_4H_9$ | H | $-CH_2-CH_2-$N(4-methylpiperazinyl) | H | OH | $CH_3$ | Cl |
| n-$C_4H_9$ | n-$C_5H_{11}$ | n-$C_5H_{11}$ | H | OH | $CH_3$ | Cl |
| n-$C_4H_9$ | n-$C_6H_{13}$ | n-$C_6H_{13}$ | H | OH | $CH_3$ | Cl |
| n-$C_4H_9$ | i-$C_3H_7$ | i-$C_3H_7$ | H | OH | $CH_3$ | Cl |
| n-$C_4H_9$ | i-$C_4H_9$ | i-$C_4H_9$ | H | OH | $CH_3$ | Cl |
| n-$C_4H_9$ | $C_2H_4OH$ | $C_2H_4OH$ | H | OH | $CH_3$ | Cl |
| n-$C_4H_9$ | $-CH_2-CH(OH)-CH_3$ | $-CH_2-CH(OH)-CH_3$ | H | OH | $CH_3$ | Cl |
| n-$C_4H_9$ | $-CH_3$ | $C_2H_4OH$ | H | OH | $CH_3$ | Cl |
| n-$C_4H_9$ | $-CH_2-CH_2-CH_2OH$ | $-CH_2-CH_2-CH_2OH$ | H | OH | $CH_3$ | Cl |
| n-$C_4H_9$ | $-CH_2-C_6H_5$ | $-CH_2-C_6H_5$ | H | OH | $CH_3$ | Cl |
| n-$C_4H_9$ | $-CH_2-CH_2-C_6H_5$ | $-CH_2-CH_2-C_6H_5$ | H | OH | $CH_3$ | Cl |
| n-$C_4H_9$ | H | cyclopentyl | H | OH | $CH_3$ | Cl |
| n-$C_4H_9$ | H | cyclohexyl | H | OH | $CH_3$ | Cl |
| n-$C_4H_9$ | H | cycloheptyl | H | OH | $CH_3$ | Cl |

TABLE IIIB-continued

| R₁ | R₂ | R₃ | R₄ | R₅ | R₆ | R₇ |
|---|---|---|---|---|---|---|
| n-C₄H₉ | |  —COOH | H | OH | CH₃ | Cl |
| n-C₄H₉ | |  —CH₂—COOH | H | OH | CH₃ | Cl |
| n-C₄H₉ | |  —CH₂—CH₂—COOH | H | OH | CH₃ | Cl |
| n-C₄H₉ | |  | H | OH | CH₃ | Cl |
| n-C₄H₉ | | 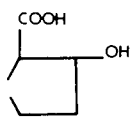 | H | OH | CH₃ | Cl |
| i-C₃H₇ | H | H | H | OH | CH₃ | Cl |
| i-C₃H₇ | H | CH₃ | H | OH | CH₃ | Cl |
| i-C₃H₇ | H | C₂H₅ | H | OH | CH₃ | Cl |
| i-C₃H₇ | H | n-C₃H₇ | H | OH | CH₃ | Cl |
| i-C₃H₇ | H | n-C₄H₉ | H | OH | CH₃ | Cl |
| i-C₃H₇ | H | i-C₃H₇ | H | OH | CH₃ | Cl |
| i-C₃H₇ | H | i-C₄H₉ | H | OH | CH₃ | Cl |
| i-C₃H₇ | H | n-C₅H₁₁ | H | OH | CH₃ | Cl |
| i-C₃H₇ | H | n-C₆H₁₃ | H | OH | CH₃ | Cl |
| i-C₃H₇ | H | C₂H₄OH | H | OH | CH₃ | Cl |
| i-C₃H₇ | H | —CH₂—CH(OH)—CH₃ | H | OH | CH₃ | Cl |
| i-C₃H₇ | H | —CH₂—CH₂—CH₂OH | H | OH | CH₃ | Cl |
| i-C₃H₇ | H | —CH₂—CH₂—N(CH₃)₂ | H | OH | CH₃ | Cl |
| i-C₃H₇ | H | —CH₂—CH₂—N(C₂H₅)₂ | H | OH | CH₃ | Cl |
| i-C₃H₇ | H | —CH₂—CH₂—N(C₄H₉)₂ | H | OH | CH₃ | Cl |
| i-C₃H₇ | H | —CH₂—CH₂—CH₂—N(CH₃)₂ | H | OH | CH₃ | Cl |
| i-C₃H₇ | H | —CH₂—CH₂—CH₂—N(C₂H₅)₂ | H | OH | CH₃ | Cl |
| i-C₃H₇ | H | —CH₂—CON(CH₃)₂ | H | OH | CH₃ | Cl |
| i-C₃H₇ | H | —CH₂—CH₂—CON(CH₃)₂ | H | OH | CH₃ | Cl |
| i-C₃H₇ | H | —CH₂—CON(C₂H₅)₂ | H | OH | CH₃ | Cl |
| i-C₃H₇ | H | —CH₂—C₆H₅ | H | OH | CH₃ | Cl |
| i-C₃H₇ | H | —CH₂—CH₂—C₆H₅ | H | OH | CH₃ | Cl |
| i-C₃H₇ | H | —CH₂—CH₂—N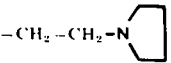 (pyrrolidinyl) | H | OH | CH₃ | Cl |
| i-C₃H₇ | H | —CH₂—CH₂—N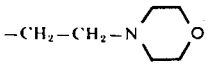 (morpholinyl) | H | OH | CH₃ | Cl |
| i-C₃H₇ | H | —CH₂—CH₂—N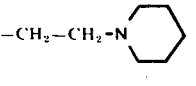 (piperidinyl) | H | OH | CH₃ | Cl |
| i-C₃H₇ | H | —CH₂—CH₂—N(piperazinyl)N—CH₃ | H | OH | CH₃ | Cl |
| i-C₃H₇ | n-C₅H₁₁ | n-C₅H₁₁ | H | OH | CH₃ | Cl |
| i-C₃H₇ | n-C₆H₁₃ | n-C₆H₁₃ | H | OH | CH₃ | Cl |
| i-C₃H₇ | i-C₃H₇ | i-C₃H₇ | H | OH | CH₃ | Cl |
| i-C₃H₇ | i-C₄H₉ | i-C₄H₉ | H | OH | CH₃ | Cl |
| i-C₃H₇ | C₂H₄OH | C₂H₄OH | H | OH | CH₃ | Cl |
| i-C₃H₇ | —CH₂—CH(OH)—CH₃ | —CH₂—CH(OH)—CH₃ | H | OH | CH₃ | Cl |
| i-C₃H₇ | —CH₃ | C₂H₄OH | H | OH | CH₃ | Cl |
| i-C₃H₇ | —CH₂—CH₂—CH₂OH | —CH₂—CH₂—CH₂OH | H | OH | CH₃ | Cl |
| i-C₃H₇ | —CH₂—C₆H₅ | —CH₂—C₆H₅ | H | OH | CH₃ | Cl |
| i-C₃H₇ | —CH₂—CH₂—C₆H₅ | —CH₂—CH₂—C₆H₅ | H | OH | CH₃ | Cl |
| i-C₃H₇ | H |  | H | OH | CH₃ | Cl |

TABLE IIIB-continued

| R₁ | R₂ | R₃ | R₄ | R₅ | R₆ | R₇ |
|---|---|---|---|---|---|---|
| i-C₃H₇ | H |  (cyclohexyl) | H | OH | CH₃ | Cl |
| i-C₃H₇ | H |  (cycloheptyl) | H | OH | CH₃ | Cl |
| i-C₃H₇ | H | 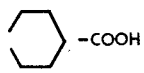 –COOH | H | OH | CH₃ | Cl |
| i-C₃H₇ | H | 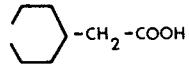 –CH₂–COOH | H | OH | CH₃ | Cl |
| i-C₃H₇ | H | 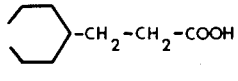 –CH₂–CH₂–COOH | H | OH | CH₃ | Cl |
| i-C₃H₇ | 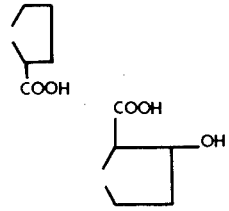 COOH | | H | OH | CH₃ | Cl |
| i-C₃H₇ | |  COOH, OH | H | OH | CH₃ | Cl |
| i-C₄H₉ | H | H | H | OH | CH₃ | Cl |
| i-C₄H₉ | H | CH₃ | H | OH | CH₃ | Cl |
| i-C₄H₉ | H | C₂H₅ | H | OH | CH₃ | Cl |
| i-C₄H₉ | H | n-C₃H₇ | H | OH | CH₃ | Cl |
| i-C₄H₉ | H | n-C₄H₉ | H | OH | CH₃ | Cl |
| i-C₄H₉ | H | i-C₃H₇ | H | OH | CH₃ | Cl |
| i-C₄H₉ | H | i-C₄H₉ | H | OH | CH₃ | Cl |
| i-C₄H₉ | H | n-C₅H₁₁ | H | OH | CH₃ | Cl |
| i-C₄H₉ | H | n-C₆H₁₃ | H | OH | CH₃ | Cl |
| i-C₄H₉ | H | C₂H₄OH | H | OH | CH₃ | Cl |
| i-C₄H₉ | H | –CH₂–CH(OH)–CH₃ | H | OH | CH₃ | Cl |
| i-C₄H₉ | H | –CH₂–CH₂–CH₂OH | H | OH | CH₃ | Cl |
| i-C₄H₉ | H | –CH₂–CH₂–N(CH₃)₂ | H | OH | CH₃ | Cl |
| i-C₄H₉ | H | –CH₂–CH₂–N(C₂H₅)₂ | H | OH | CH₃ | Cl |
| i-C₄H₉ | H | –CH₂–CH₂–N(C₄H₉)₂ | H | OH | CH₃ | Cl |
| i-C₄H₉ | H | –CH₂–CH₂–CH₂–N(CH₃)₂ | H | OH | CH₃ | Cl |
| i-C₄H₉ | H | –CH₂–CH₂–CH₂–N(C₂H₅)₂ | H | OH | CH₃ | Cl |
| i-C₄H₉ | H | –CH₂–CON(CH₃)₂ | H | OH | CH₃ | Cl |
| i-C₄H₉ | H | –CH₂–CH₂–CON(CH₃)₂ | H | OH | CH₃ | Cl |
| i-C₄H₉ | H | –CH₂–CON(C₂H₅)₂ | H | OH | CH₃ | Cl |
| i-C₄H₉ | H | –CH₂–C₆H₅ | H | OH | CH₃ | Cl |
| i-C₄H₉ | H | –CH₂–CH₂–C₆H₅ | H | OH | CH₃ | Cl |
| i-C₄H₉ | H |  –CH₂–CH₂–N(pyrrolidine) | H | OH | CH₃ | Cl |
| i-C₄H₉ | H |  –CH₂–CH₂–N(morpholine) | H | OH | CH₃ | Cl |
| i-C₄H₉ | H |  –CH₂–CH₂–N(piperidine) | H | OH | CH₃ | Cl |
| i-C₄H₉ | H |  –CH₂–CH₂–N(N-methylpiperazine)–CH₃ | H | OH | CH₃ | Cl |
| i-C₄H₉ | n-C₅H₁₁ | n-C₅H₁₁ | H | OH | CH₃ | Cl |
| i-C₄H₉ | n-C₆H₁₃ | n-C₆H₁₃ | H | OH | CH₃ | Cl |
| i-C₄H₉ | i-C₃H₇ | i-C₃H₇ | H | OH | CH₃ | Cl |
| i-C₄H₉ | i-C₄H₉ | i-C₄H₉ | H | OH | CH₃ | Cl |
| i-C₄H₉ | C₂H₄OH | C₂H₄OH | H | OH | CH₃ | Cl |
| i-C₄H₉ | –CH₂–CH(OH)–CH₃ | –CH₂–CH(OH)–CH₃ | H | OH | CH₃ | Cl |

TABLE IIIB-continued

| R₁ | R₂ | R₃ | R₄ | R₅ | R₆ | R₇ |
|---|---|---|---|---|---|---|
| i-C₄H₉ | —CH₃ | C₂H₄OH | H | OH | CH₃ | Cl |
| i-C₄H₉ | —CH₂—CH₂—CH₂OH | —CH₂—CH₂—CH₂OH | H | OH | CH₃ | Cl |
| i-C₄H₉ | —CH₂—C₆H₅ | —CH₂—C₆H₅ | H | OH | CH₃ | Cl |
| i-C₄H₉ | —CH₂—CH₂—C₆H₅ | —CH₂—CH₂—C₆H₅ | H | OH | CH₃ | Cl |
| i-C₄H₉ | H |  | H | OH | CH₃ | Cl |
| i-C₄H₉ | H |  | H | OH | CH₃ | Cl |
| i-C₄H₉ | H |  | H | OH | CH₃ | Cl |
| i-C₄H₉ | | 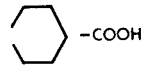 —COOH | H | OH | CH₃ | Cl |
| i-C₄H₉ | | 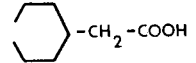 —CH₂—COOH | H | OH | CH₃ | Cl |
| i-C₄H₉ | | 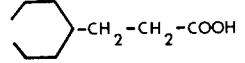 —CH₂—CH₂—COOH | H | OH | CH₃ | Cl |
| i-C₄H₉ |  COOH | | H | OH | CH₃ | Cl |
| i-C₄H₉ | | 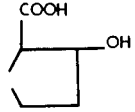 | H | OH | CH₃ | Cl |
| sec.-C₄H₉ | H | H | H | OH | CH₃ | Cl |
| sec.-C₄H₉ | H | CH₃ | H | OH | CH₃ | Cl |
| sec.-C₄H₉ | H | C₂H₅ | H | OH | CH₃ | Cl |
| sec.-C₄H₉ | H | n-C₃H₇ | H | OH | CH₃ | Cl |
| sec.-C₄H₉ | H | n-C₄H₉ | H | OH | CH₃ | Cl |
| sec.-C₄H₉ | H | i-C₃H₇ | H | OH | CH₃ | Cl |
| sec.-C₄H₉ | H | i-C₄H₉ | H | OH | CH₃ | Cl |
| sec.-C₄H₉ | H | n-C₅H₁₁ | H | OH | CH₃ | Cl |
| sec.-C₄H₉ | H | n-C₆H₁₃ | H | OH | CH₃ | Cl |
| sec.-C₄H₉ | H | C₂H₄OH | H | OH | CH₃ | Cl |
| sec.-C₄H₉ | H | —CH₂—CH—CH₃<br>　　　　OH | H | OH | CH₃ | Cl |
| sec.-C₄H₉ | H | —CH₂—CH₂—CH₂OH | H | OH | CH₃ | Cl |
| sec.-C₄H₉ | H | —CH₂—CH₂—N(CH₃)₂ | H | OH | CH₃ | Cl |
| sec.-C₄H₉ | H | —CH₂—CH₂—N(C₂H₅)₂ | H | OH | CH₃ | Cl |
| sec.-C₄H₉ | H | —CH₂—CH₂—N(C₄H₉)₂ | H | OH | CH₃ | Cl |
| sec.-C₄H₉ | H | —CH₂—CH₂—CH₂—N(CH₃)₂ | H | OH | CH₃ | Cl |
| sec.-C₄H₉ | H | —CH₂—CH₂—CH₂—N(C₂H₅)₂ | H | OH | CH₃ | Cl |
| sec.-C₄H₉ | H | —CH₂—CON(CH₃)₂ | H | OH | CH₃ | Cl |
| sec.-C₄H₉ | H | —CH₂—CH₂—CON(CH₃)₂ | H | OH | CH₃ | Cl |
| sec.-C₄H₉ | H | —CH₂—CON(C₂H₅)₂ | H | OH | CH₃ | Cl |
| sec.-C₄H₉ | H | —CH₂—C₆H₅ | H | OH | CH₃ | Cl |
| sec.-C₄H₉ | H | —CH₂—CH₂—C₆H₅ | H | OH | CH₃ | Cl |
| sec.-C₄H₉ | H | 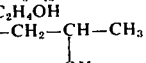 | H | OH | CH₃ | Cl |
| sec.-C₄H₉ | H | 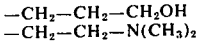 | H | OH | CH₃ | Cl |
| sec.-C₄H₉ | H | 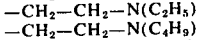 | H | OH | CH₃ | Cl |

TABLE IIIB-continued

| R₁ | R₂ | R₃ | R₄ | R₅ | R₆ | R₇ |
|---|---|---|---|---|---|---|
| sec.-C₄H₉ | H | —CH₂—CH₂—NN—CH₃ | H | OH | CH₃ | Cl |
| sec.-C₄H₉ | n-C₅H₁₁ | n-C₅H₁₁ | H | OH | CH₃ | Cl |
| sec.-C₄H₉ | n-C₆H₁₃ | n-C₆H₁₃ | H | OH | CH₃ | Cl |
| sec.-C₄H₉ | i-C₃H₇ | i-C₃H₇ | H | OH | CH₃ | Cl |
| sec.-C₄H₉ | i-C₄H₉ | i-C₄H₉ | H | OH | CH₃ | Cl |
| sec.-C₄H₉ | C₂H₄OH | C₂H₄OH | H | OH | CH₃ | Cl |
| sec.-C₄H₉ | —CH₂—CH—CH₃<br>　　　　OH | —CH₂—CH—CH₃<br>　　　　OH | H | OH | CH₃ | Cl |
| sec.-C₄H₉ | —CH₃ | C₂H₄OH | H | OH | CH₃ | Cl |
| sec.-C₄H₉ | —CH₂—CH₂—CH₂OH | —CH₂—CH₂—CH₂OH | H | OH | CH₃ | Cl |
| sec.-C₄H₉ | —CH₂—C₆H₅ | —CH₂—C₆H₅ | H | OH | CH₃ | Cl |
| sec.-C₄H₉ | —CH₂—CH₂—C₆H₅ | —CH₂—CH₂—C₆H₅ | H | OH | CH₃ | Cl |
| sec.-C₄H₉ | H |  | H | OH | CH₃ | Cl |
| sec.-C₄H₉ | H |  | H | OH | CH₃ | Cl |
| sec.-C₄H₉ | H |  | H | OH | CH₃ | Cl |
| sec.-C₄H₉ | 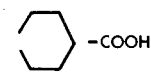 | | H | OH | CH₃ | Cl |
| sec.-C₄H₉ | 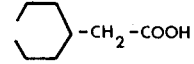 | | H | OH | CH₃ | Cl |
| sec.-C₄H₉ | 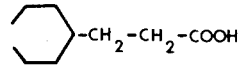 | | H | OH | CH₃ | Cl |
| sec.-C₄H₉ |  | | H | OH | CH₃ | Cl |
| sec.-C₄H₉ |  | | H | OH | CH₃ | Cl |

TABLE IVA

| R₁ | R₂ | R₃ | R₄ | R₅ | R₆ | R₇ |
|---|---|---|---|---|---|---|
| CH₃ | CH₃ | CH₃ | OH | H | CH₃ | H |
| CH₃ | CH₃ | C₂H₅ | OH | H | CH₃ | H |
| CH₃ | C₂H₅ | C₂H₅ | OH | H | CH₃ | H |
| CH₃ | n-C₃H₇ | n-C₃H₇ | OH | H | CH₃ | H |
| CH₃ | n-C₄H₉ | n-C₄H₉ | OH | H | CH₃ | H |
| CH₃ | H | CH₂—COOH | OH | H | CH₃ | H |
| CH₃ | H | CH₂—COOC₂H₅ | OH | H | CH₃ | H |
| CH₃ | H | CH₃—CH—COOH | OH | H | CH₃ | H |
| CH₃ | H | CH₃—CH—COOC₂H₅ | OH | H | CH₃ | H |
| CH₃ | H | —CH₂—CH₂—COOH | OH | H | CH₃ | H |
| CH₃ | H | —CH₂—CH₂—COOC₂H₅ | OH | H | CH₃ | H |
| CH₃ | H | —(CH₂)₄—CH—COOH<br>　　　　　　　NH₂ | OH | H | CH₃ | H |
| CH₃ | 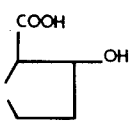 | | OH | H | CH₃ | H |
| CH₃ |  | | OH | H | CH₃ | H |
| CH₃ |  | | OH | H | CH₃ | H |
| CH₃ |  | | OH | H | CH₃ | H |
| CH₃ |  | | OH | H | CH₃ | H |
| CH₃ |  | | OH | H | CH₃ | H |
| CH₃ |  | | OH | H | CH₃ | H |

TABLE IVA-continued

| R₁ | R₂ | R₃ | R₄ | R₅ | R₆ | R₇ |
|---|---|---|---|---|---|---|
| CH₃ | | piperazinyl-N-C₂H₅OH | OH | H | CH₃ | H |
| C₂H₅ | CH₃ | CH₃ | OH | H | CH₃ | H |
| C₂H₅ | CH₃ | C₂H₅ | OH | H | CH₃ | H |
| C₂H₅ | C₂H₅ | C₂H₅ | OH | H | CH₃ | H |
| C₂H₅ | n-C₃H₇ | n-C₃H₇ | OH | H | CH₃ | H |
| C₂H₅ | n-C₄H₉ | n-C₄H₉ | OH | H | CH₃ | H |
| C₂H₅ | H | CH₂—COOH | OH | H | CH₃ | H |
| C₂H₅ | H | CH₂—COOC₂H₅ | OH | H | CH₃ | H |
| C₂H₅ | H | CH₃—CH—COOH | OH | H | CH₃ | H |
| C₂H₅ | H | CH₃—CH—COOC₂H₅ | OH | H | CH₃ | H |
| C₂H₅ | H | —CH₂—CH₂—COOH | OH | H | CH₃ | H |
| C₂H₅ | H | —CH₂—CH₂—COOC₂H₅ | OH | H | CH₃ | H |
| C₂H₅ | H | —(CH₂)₄—CH(NH₂)—COOH | OH | H | CH₃ | H |
| C₂H₅ | pyrrolidinyl | | OH | H | CH₃ | H |
| C₂H₅ | piperidinyl | | OH | H | CH₃ | H |
| C₂H₅ | morpholinyl | | OH | H | CH₃ | H |
| C₂H₅ | piperazinyl-NH | | OH | H | CH₃ | H |
| C₂H₅ | piperazinyl-N-CH₃ | | OH | H | CH₃ | H |
| C₂H₅ | piperazinyl-N-C₂H₅ | | OH | H | CH₃ | H |
| C₂H₅ | piperazinyl-N-C₂H₅OH | | OH | H | CH₃ | H |
| n-C₃H₇ | CH₃ | CH₃ | OH | H | CH₃ | H |
| n-C₃H₇ | CH₃ | C₂H₅ | OH | H | CH₃ | H |
| n-C₃H₇ | C₂H₅ | C₂H₅ | OH | H | CH₃ | H |
| n-C₃H₇ | n-C₃H₇ | n-C₃H₇ | OH | H | CH₃ | H |
| n-C₃H₇ | n-C₄H₉ | n-C₄H₉ | OH | H | CH₃ | H |
| n-C₃H₇ | H | CH₂—COOH | OH | H | CH₃ | H |
| n-C₃H₇ | H | CH₂—COOC₂H₅ | OH | H | CH₃ | H |
| n-C₃H₇ | H | CH₃—CH—COOH | OH | H | CH₃ | H |
| n-C₃H₇ | H | CH₃—CH—COOC₂H₅ | OH | H | CH₃ | H |
| n-C₃H₇ | H | —CH₂—CH₂—COOH | OH | H | CH₃ | H |
| n-C₃H₇ | H | —CH₂—CH₂—COOC₂H₅ | OH | H | CH₃ | H |
| n-C₃H₇ | H | —(CH₂)₄—CH(NH₂)—COOH | OH | H | CH₃ | H |
| n-C₃H₇ | pyrrolidinyl | | OH | H | CH₃ | H |
| n-C₃H₇ | piperidinyl | | OH | H | CH₃ | H |
| n-C₃H₇ | morpholinyl | | OH | H | CH₃ | H |
| n-C₃H₇ | piperazinyl-NH | | OH | H | CH₃ | H |
| n-C₃H₇ | piperazinyl-N-CH₃ | | OH | H | CH₃ | H |
| n-C₃H₇ | piperazinyl-N-C₂H₅ | | OH | H | CH₃ | H |
| n-C₃H₇ | piperazinyl-N-C₂H₅OH | | OH | H | CH₃ | H |
| n-C₄H₉ | CH₃ | CH₃ | OH | H | CH₃ | H |
| n-C₄H₉ | CH₃ | C₂H₅ | OH | H | CH₃ | H |
| n-C₄H₉ | C₂H₅ | C₂H₅ | OH | H | CH₃ | H |
| n-C₄H₉ | n-C₃H₇ | n-C₃H₇ | OH | H | CH₃ | H |
| n-C₄H₉ | n-C₄H₉ | n-C₃H₇ | OH | H | CH₃ | H |
| n-C₄H₉ | H | CH₂—COOH | OH | H | CH₃ | H |
| n-C₄H₉ | H | CH₂—COOC₂H₅ | OH | H | CH₃ | H |
| n-C₄H₉ | H | CH₃—CH—COOH | OH | H | CH₃ | H |
| n-C₄H₉ | H | CH₃—CH—COOC₂H₅ | OH | H | CH₃ | H |
| n-C₄H₉ | H | —CH₂—CH₂—COOH | OH | H | CH₃ | H |
| n-C₄H₉ | H | —CH₂—CH₂—COOC₂H₅ | OH | H | CH₃ | H |
| n-C₄H₉ | H | —(CH₂)₄—CH(NH₂)—COOH | OH | H | CH₃ | H |
| n-C₄H₉ | pyrrolidinyl | | OH | H | CH₃ | H |
| n-C₄H₉ | piperidinyl | | OH | H | CH₃ | H |
| n-C₄H₉ | morpholinyl | | OH | H | CH₃ | H |
| n-C₄H₉ | piperazinyl-NH | | OH | H | CH₃ | H |
| n-C₄H₉ | piperazinyl-N-CH₃ | | OH | H | CH₃ | H |
| n-C₄H₉ | piperazinyl-N-C₂H₅ | | OH | H | CH₃ | H |
| n-C₄H₉ | piperazinyl-N-C₂H₅OH | | OH | H | CH₃ | H |

TABLE IVB

| R₁ | R₂ | R₃ | R₄ | R₅ | R₆ | R₇ |
|---|---|---|---|---|---|---|
| CH₃ | H | H | OH | H | CH₃ | H |
| CH₃ | H | CH₃ | OH | H | CH₃ | H |
| CH₃ | H | C₂H₅ | OH | H | CH₃ | H |
| CH₃ | H | n-C₃H₇ | OH | H | CH₃ | H |
| CH₃ | H | n-C₄H₉ | OH | H | CH₃ | H |
| CH₃ | H | i-C₃H₇ | OH | H | CH₃ | H |

TABLE IVB-continued

| R₁ | R₂ | R₃ | R₄ | R₅ | R₆ | R₇ |
|---|---|---|---|---|---|---|
| CH₃ | H | i-C₄H₉ | OH | H | CH₃ | H |
| CH₃ | H | n-C₅H₁₁ | OH | H | CH₃ | H |
| CH₃ | H | n-C₆H₁₃ | OH | H | CH₃ | H |
| CH₃ | H | C₂H₄OH | OH | H | CH₃ | H |
| CH₃ | H | —CH₂—CH(OH)—CH₃ | OH | H | CH₃ | H |
| CH₃ | H | —CH₂—CH₂—CH₂OH | OH | H | CH₃ | H |
| CH₃ | H | —CH₂—CH₂—N(CH₃)₂ | OH | H | CH₃ | H |
| CH₃ | H | —CH₂—CH₂—N(C₂H₅)₂ | OH | H | CH₃ | H |
| CH₃ | H | —CH₂—CH₂—N(C₄H₉)₂ | OH | H | CH₃ | H |
| CH₃ | H | —CH₂—CH₂—CH₂—N(CH₃)₂ | OH | H | CH₃ | H |
| CH₃ | H | —CH₂—CH₂—CH₂—N(C₂H₅)₂ | OH | H | CH₃ | H |
| CH₃ | H | —CH₂—CON(CH₃)₂ | OH | H | CH₃ | H |
| CH₃ | H | —CH₂—CH₂—CON(CH₃)₂ | OH | H | CH₃ | H |
| CH₃ | H | —CH₂—CON(C₂H₅)₂ | OH | H | CH₃ | H |
| CH₃ | H | —CH₂—C₆H₅ | OH | H | CH₃ | H |
| CH₃ | H | —CH₂—CH₂—C₆H₅ | OH | H | CH₃ | H |
| CH₃ | H | —CH₂—CH₂—N<pyrrolidine> | OH | H | CH₃ | H |
| CH₃ | H | —CH₂—CH₂—N<morpholine> | OH | H | CH₃ | H |
| CH₃ | H | —CH₂—CH₂—N<piperidine> | OH | H | CH₃ | H |
| CH₃ | H | —CH₂—CH₂—N<N-methylpiperazine> | OH | H | CH₃ | H |
| CH₃ | n-C₅H₁₁ | n-C₅H₁₁ | OH | H | CH₃ | H |
| CH₃ | n-C₆H₁₃ | n-C₆H₁₃ | OH | H | CH₃ | H |
| CH₃ | i-C₃H₇ | i-C₃H₇ | OH | H | CH₃ | H |
| CH₃ | i-C₄H₉ | i-C₄H₉ | OH | H | CH₃ | H |
| CH₃ | C₂H₄OH | C₂H₄OH | OH | H | CH₃ | H |
| CH₃ | —CH₂—CH(OH)—CH₃ | —CH₂—CH(OH)—CH₃ | OH | H | CH₃ | H |
| CH₃ | —CH₃ | C₂H₄OH | OH | H | CH₃ | H |
| CH₃ | —CH₂—CH₂—CH₂OH | —CH₂—CH₂—CH₂OH | OH | H | CH₃ | H |
| CH₃ | —CH₂—C₆H₅ | —CH₂—C₆H₅ | OH | H | CH₃ | H |
| CH₃ | —CH₂—CH₂—C₆H₅ | —CH₂—CH₂—C₆H₅ | OH | H | CH₃ | H |
| CH₃ | H | cyclopentyl | OH | H | CH₃ | H |
| CH₃ | H | cyclohexyl | OH | H | CH₃ | H |
| CH₃ | H | cycloheptyl | OH | H | CH₃ | H |
| CH₃ | | cyclohexyl-COOH | OH | H | CH₃ | H |
| CH₃ | | cyclohexyl-CH₂-COOH | OH | H | CH₃ | H |
| CH₃ | | cyclohexyl-CH₂-CH₂-COOH | OH | H | CH₃ | H |
| CH₃ | cyclopentyl-COOH | | OH | H | CH₃ | H |
| CH₃ | | cyclopentyl(COOH)(OH) | OH | H | CH₃ | H |

TABLE IVB-continued

| R₁ | R₂ | R₃ | R₄ | R₅ | R₆ | R₇ |
|---|---|---|---|---|---|---|
| C₂H₅ | H | H | OH | H | CH₃ | H |
| C₂H₅ | H | CH₃ | OH | H | CH₃ | H |
| C₂H₅ | H | C₂H₅ | OH | H | CH₃ | H |
| C₂H₅ | H | n-C₃H₇ | OH | H | CH₃ | H |
| C₂H₅ | H | n-C₄H₉ | OH | H | CH₃ | H |
| C₂H₅ | H | i-C₃H₇ | OH | H | CH₃ | H |
| C₂H₅ | H | i-C₄H₉ | OH | H | CH₃ | H |
| C₂H₅ | H | n-C₅H₁₁ | OH | H | CH₃ | H |
| C₂H₅ | H | n-C₆H₁₃ | OH | H | CH₃ | H |
| C₂H₅ | H | C₂H₄OH | OH | H | CH₃ | H |
| C₂H₅ | H | —CH₂—CH(OH)—CH₃ | OH | H | CH₃ | H |
| C₂H₅ | H | —CH₂—CH₂—CH₂OH | OH | H | CH₃ | H |
| C₂H₅ | H | —CH₂—CH₂—N(CH₃)₂ | OH | H | CH₃ | H |
| C₂H₅ | H | —CH₂—CH₂—N(C₂H₅)₂ | OH | H | CH₃ | H |
| C₂H₅ | H | —CH₂—CH₂—N(C₄H₉)₂ | OH | H | CH₃ | H |
| C₂H₅ | H | —CH₂—CH₂—CH₂—N(CH₃)₂ | OH | H | CH₃ | H |
| C₂H₅ | H | —CH₂—CH₂—CH₂—N(C₂H₅)₂ | OH | H | CH₃ | H |
| C₂H₅ | H | —CH₂—CON(CH₃)₂ | OH | H | CH₃ | H |
| C₂H₅ | H | —CH₂—CH₂—CON(CH₃)₂ | OH | H | CH₃ | H |
| C₂H₅ | H | —CH₂—CON(C₂H₅)₂ | OH | H | CH₃ | H |
| C₂H₅ | H | —CH₂—C₆H₅ | OH | H | CH₃ | H |
| C₂H₅ | H | —CH₂—CH₂—C₆H₅ | OH | H | CH₃ | H |
| C₂H₅ | H | —CH₂—CH₂—N(pyrrolidinyl)  | OH | H | CH₃ | H |
| C₂H₅ | H | —CH₂—CH₂—N(morpholinyl)  | OH | H | CH₃ | H |
| C₂H₅ | H | —CH₂—CH₂—N(piperidinyl)  | OH | H | CH₃ | H |
| C₂H₅ | H | —CH₂—CH₂—N(N'-methylpiperazinyl)  | OH | H | CH₃ | H |
| C₂H₅ | n-C₅H₁₁ | n-C₅H₁₁ | OH | H | CH₃ | H |
| C₂H₅ | n-C₆H₁₃ | n-C₆H₁₃ | OH | H | CH₃ | H |
| C₂H₅ | i-C₃H₇ | i-C₃H₇ | OH | H | CH₃ | H |
| C₂H₅ | i-C₄H₉ | i-C₄H₉ | OH | H | CH₃ | H |
| C₂H₅ | C₂H₄OH | C₂H₄OH | OH | H | CH₃ | H |
| C₂H₅ | —CH₂—CH(OH)—CH₃ | —CH₂—CH(OH)—CH₃ | OH | H | CH₃ | H |
| C₂H₅ | —CH₃ | C₂H₄OH | OH | H | CH₃ | H |
| C₂H₅ | —CH₂—CH₂—CH₂OH | —CH₂—CH₂—CH₂OH | OH | H | CH₃ | H |
| C₂H₅ | —CH₂—C₆H₅ | —CH₂—C₆H₅ | OH | H | CH₃ | H |
| C₂H₅ | —CH₂—CH₂—C₆H₅ | —CH₂—CH₂—C₆H₅ | OH | H | CH₃ | H |
| C₂H₅ | H | cyclopentyl  | OH | H | CH₃ | H |
| C₂H₅ | H | cyclohexyl  | OH | H | CH₃ | H |
| C₂H₅ | H | cycloheptyl  | OH | H | CH₃ | H |
| C₂H₅ |  —COOH | | OH | H | CH₃ | H |
| C₂H₅ |  —CH₂—COOH | | OH | H | CH₃ | H |
| C₂H₅ |  —CH₂—CH₂—COOH | | OH | H | CH₃ | H |

TABLE IVB-continued

| R₁ | R₂ | R₃ | R₄ | R₅ | R₆ | R₇ |
|---|---|---|---|---|---|---|
| C₂H₅ | (cyclopentane-COOH) | | OH | H | CH₃ | H |
| C₂H₅ | (cyclopentane with COOH and OH) | | OH | H | CH₃ | H |
| n-C₃H₇ | H | H | OH | H | CH₃ | H |
| n-C₃H₇ | H | CH₃ | OH | H | CH₃ | H |
| n-C₃H₇ | H | C₂H₅ | OH | H | CH₃ | H |
| n-C₃H₇ | H | n-C₃H₇ | OH | H | CH₃ | H |
| n-C₃H₇ | H | n-C₄H₉ | OH | H | CH₃ | H |
| n-C₃H₇ | H | i-C₃H₇ | OH | H | CH₃ | H |
| n-C₃H₇ | H | i-C₄H₉ | OH | H | CH₃ | H |
| n-C₃H₇ | H | n-C₅H₁₁ | OH | H | CH₃ | H |
| n-C₃H₇ | H | n-C₆H₁₃ | OH | H | CH₃ | H |
| n-C₃H₇ | H | C₂H₄OH | OH | H | CH₃ | H |
| n-C₃H₇ | H | —CH₂—CH(OH)—CH₃ | OH | H | CH₃ | H |
| n-C₃H₇ | H | —CH₂—CH₂—CH₂OH | OH | H | CH₃ | H |
| n-C₃H₇ | H | —CH₂—CH₂—N(CH₃)₂ | OH | H | CH₃ | H |
| n-C₃H₇ | H | —CH₂—CH₂—N(C₂H₅)₂ | OH | H | CH₃ | H |
| n-C₃H₇ | H | —CH₂—CH₂—N(C₄H₉)₂ | OH | H | CH₃ | H |
| n-C₃H₇ | H | —CH₂—CH₂—CH₂—N(CH₃)₂ | OH | H | CH₃ | H |
| n-C₃H₇ | H | —CH₂—CH₂—CH₂—N(C₂H₅)₂ | OH | H | CH₃ | H |
| n-C₃H₇ | H | —CH₂—CON(CH₃)₂ | OH | H | CH₃ | H |
| n-C₃H₇ | H | —CH₂—CH₂—CON(CH₃)₂ | OH | H | CH₃ | H |
| n-C₃H₇ | H | —CH₂—CON(C₂H₅)₂ | OH | H | CH₃ | H |
| n-C₃H₇ | H | —CH₂—C₆H₅ | OH | H | CH₃ | H |
| n-C₃H₇ | H | —CH₂—CH₂—C₆H₅ | OH | H | CH₃ | H |
| n-C₃H₇ | H | —CH₂—CH₂—N(pyrrolidinyl) | OH | H | CH₃ | H |
| n-C₃H₇ | H | —CH₂—CH₂—N(morpholinyl) | OH | H | CH₃ | H |
| n-C₃H₇ | H | —CH₂—CH₂—N(piperidinyl) | OH | H | CH₃ | H |
| n-C₃H₇ | H | —CH₂—CH₂—N(N-methylpiperazinyl)—CH₃ | OH | H | CH₃ | H |
| n-C₃H₇ | n-C₅H₁₁ | n-C₅H₁₁ | OH | H | CH₃ | H |
| n-C₃H₇ | n-C₆H₁₃ | n-C₆H₁₃ | OH | H | CH₃ | H |
| n-C₃H₇ | i-C₃H₇ | i-C₃H₇ | OH | H | CH₃ | H |
| n-C₃H₇ | i-C₄H₉ | i-C₄H₉ | OH | H | CH₃ | H |
| n-C₃H₇ | C₂H₄OH | C₂H₄OH | OH | H | CH₃ | H |
| n-C₃H₇ | —CH₂—CH(OH)—CH₃ | —CH₂—CH(OH)—CH₃ | OH | H | CH₃ | H |
| n-C₃H₇ | —CH₃ | C₂H₄OH | OH | H | CH₃ | H |
| n-C₃H₇ | —CH₂—CH₂—CH₂OH | —CH₂—CH₂—CH₂OH | OH | H | CH₃ | H |
| n-C₃H₇ | —CH₂—C₆H₅ | —CH₂—C₆H₅ | OH | H | CH₃ | H |
| n-C₃H₇ | —CH₂—CH₂—C₆H₅ | —CH₂—CH₂—C₆H₅ | OH | H | CH₃ | H |
| n-C₃H₇ | H | (cyclopentyl) | OH | H | CH₃ | H |
| n-C₃H₇ | H | (cyclohexyl) | OH | H | CH₃ | H |
| n-C₃H₇ | H | (cycloheptyl) | OH | H | CH₃ | H |
| n-C₃H₇ | (cyclohexyl)—COOH | | OH | H | CH₃ | H |

TABLE IVB-continued

| R₁ | R₂ | R₃ | R₄ | R₅ | R₆ | R₇ |
|---|---|---|---|---|---|---|
| n-C₃H₇ |  | (cyclohexyl)-CH₂-COOH | OH | H | CH₃ | H |
| n-C₃H₇ |  | (cyclohexyl)-CH₂-CH₂-COOH | OH | H | CH₃ | H |
| n-C₃H₇ | (cyclopentyl)-COOH |  | OH | H | CH₃ | H |
| n-C₃H₇ |  | (cyclopentyl with COOH and OH) | OH | H | CH₃ | H |
| n-C₄H₉ | H | H | OH | H | CH₃ | H |
| n-C₄H₉ | H | CH₃ | OH | H | CH₃ | H |
| n-C₄H₉ | H | C₂H₅ | OH | H | CH₃ | H |
| n-C₄H₉ | H | n-C₃H₇ | OH | H | CH₃ | H |
| n-C₄H₉ | H | n-C₄H₉ | OH | H | CH₃ | H |
| n-C₄H₉ | H | i-C₃H₇ | OH | H | CH₃ | H |
| n-C₄H₉ | H | i-C₄H₉ | OH | H | CH₃ | H |
| n-C₄H₉ | H | n-C₅H₁₁ | OH | H | CH₃ | H |
| n-C₄H₉ | H | n-C₆H₁₃ | OH | H | CH₃ | H |
| n-C₄H₉ | H | C₂H₄OH | OH | H | CH₃ | H |
| n-C₄H₉ | H | —CH₂—CH(OH)—CH₃ | OH | H | CH₃ | H |
| n-C₄H₉ | H | —CH₂—CH₂—CH₂OH | OH | H | CH₃ | H |
| n-C₄H₉ | H | —CH₂—CH₂—N(CH₃)₂ | OH | H | CH₃ | H |
| n-C₄H₉ | H | —CH₂—CH₂—N(C₂H₅)₂ | OH | H | CH₃ | H |
| n-C₄H₉ | H | —CH₂—CH₂—N(C₄H₉)₂ | OH | H | CH₃ | H |
| n-C₄H₉ | H | —CH₂—CH₂—CH₂—N(CH₃)₂ | OH | H | CH₃ | H |
| n-C₄H₉ | H | —CH₂—CH₂—CH₂—N(C₂H₅)₂ | OH | H | CH₃ | H |
| n-C₄H₉ | H | —CH₂—CON(CH₃)₂ | OH | H | CH₃ | H |
| n-C₄H₉ | H | —CH₂—CH₂—CON(CH₃)₂ | OH | H | CH₃ | H |
| n-C₄H₉ | H | —CH₂—CON(C₂H₅)₂ | OH | H | CH₃ | H |
| n-C₄H₉ | H | —CH₂—C₆H₅ | OH | H | CH₃ | H |
| n-C₄H₉ | H | —CH₂—CH₂—C₆H₅ | OH | H | CH₃ | H |
| n-C₄H₉ | H | —CH₂—CH₂—N(pyrrolidine) | OH | H | CH₃ | H |
| n-C₄H₉ | H | —CH₂—CH₂—N(morpholine) | OH | H | CH₃ | H |
| n-C₄H₉ | H | —CH₂—CH₂—N(piperidine) | OH | H | CH₃ | H |
| n-C₄H₉ | H | —CH₂—CH₂—N(N-methylpiperazine)—CH₃ | OH | H | CH₃ | H |
| n-C₄H₉ | n-C₅H₁₁ | n-C₅H₁₁ | OH | H | CH₃ | H |
| n-C₄H₉ | n-C₆H₁₃ | n-C₆H₁₃ | OH | H | CH₃ | H |
| n-C₄H₉ | i-C₃H₇ | i-C₃H₇ | OH | H | CH₃ | H |
| n-C₄H₉ | i-C₄H₉ | i-C₄H₉ | OH | H | CH₃ | H |
| n-C₄H₉ | C₂H₄OH | C₂H₄OH | OH | H | CH₃ | H |
| n-C₄H₉ | —CH₂—CH(OH)—CH₃ | —CH₂—CH(OH)—CH₃ | OH | H | CH₃ | H |
| n-C₄H₉ | —CH₃ | C₂H₄OH | OH | H | CH₃ | H |
| n-C₄H₉ | —CH₂—CH₂—CH₂OH | —CH₂—CH₂—CH₂OH | OH | H | CH₃ | H |
| n-C₄H₉ | —CH₂—C₆H₅ | —CH₂—C₆H₅ | OH | H | CH₃ | H |
| n-C₄H₉ | —CH₂—CH₂—C₆H₅ | —CH₂—CH₂—C₆H₅ | OH | H | CH₃ | H |
| n-C₄H₉ | H | cyclopentyl | OH | H | CH₃ | H |
| n-C₄H₉ | H | cyclohexyl | OH | H | CH₃ | H |

TABLE IVB-continued

| R₁ | R₂ | R₃ | R₄ | R₅ | R₆ | R₇ |
|---|---|---|---|---|---|---|
| n-C₄H₉ | H |  | OH | H | CH₃ | H |
| n-C₄H₉ | | 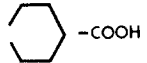-COOH | OH | H | CH₃ | H |
| n-C₄H₉ | | 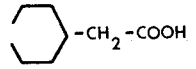-CH₂-COOH | OH | H | CH₃ | H |
| n-C₄H₉ | | 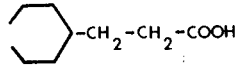-CH₂-CH₂-COOH | OH | H | CH₃ | H |
| n-C₄H₉ | 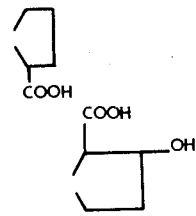 | | OH | H | CH₃ | H |
| n-C₄H₉ | | 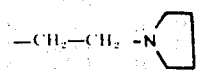 | OH | H | CH₃ | H |
| i-C₃H₇ | H | H | OH | H | CH₃ | H |
| i-C₃H₇ | H | CH₃ | OH | H | CH₃ | H |
| i-C₃H₇ | H | C₂H₅ | OH | H | CH₃ | H |
| i-C₃H₇ | H | n-C₃H₇ | OH | H | CH₃ | H |
| i-C₃H₇ | H | n-C₄H₉ | OH | H | CH₃ | H |
| i-C₃H₇ | H | i-C₃H₇ | OH | H | CH₃ | H |
| i-C₃H₇ | H | i-C₄H₉ | OH | H | CH₃ | H |
| i-C₃H₇ | H | n-C₅H₁₁ | OH | H | CH₃ | H |
| i-C₃H₇ | H | n-C₆H₁₃ | OH | H | CH₃ | H |
| i-C₃H₇ | H | C₂H₄OH | OH | H | CH₃ | H |
| i-C₃H₇ | H | —CH₂—CH(OH)—CH₃ | OH | H | CH₃ | H |
| i-C₃H₇ | H | —CH₂—CH₂—CH₂OH | OH | H | CH₃ | H |
| i-C₃H₇ | H | —CH₂—CH₂—N(CH₃)₂ | OH | H | CH₃ | H |
| i-C₃H₇ | H | —CH₂—CH₂—N(C₂H₅)₂ | OH | H | CH₃ | H |
| i-C₃H₇ | H | —CH₂—CH₂—N(C₄H₉)₂ | OH | H | CH₃ | H |
| i-C₃H₇ | H | —CH₂—CH₂—CH₂—N(CH₃)₂ | OH | H | CH₃ | H |
| i-C₃H₇ | H | —CH₂—CH₂—CH₂—N(C₂H₅)₂ | OH | H | CH₃ | H |
| i-C₃H₇ | H | —CH₂—CON(CH₃)₂ | OH | H | CH₃ | H |
| i-C₃H₇ | H | —CH₂—CH₂—CON(CH₃)₂ | OH | H | CH₃ | H |
| i-C₃H₇ | H | —CH₂—CON(C₂H₅)₂ | OH | H | CH₃ | H |
| i-C₃H₇ | H | —CH₂—C₆H₅ | OH | H | CH₃ | H |
| i-C₃H₇ | H | —CH₂—CH₂—C₆H₅ | OH | H | CH₃ | H |
| i-C₃H₇ | H | 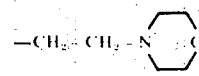 | OH | H | CH₃ | H |
| i-C₃H₇ | H | 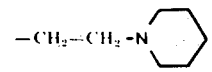 | OH | H | CH₃ | H |
| i-C₃H₇ | H | 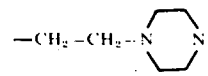 | OH | H | CH₃ | H |
| i-C₃H₇ | H | —CH₂—CH₂—N(piperazine)—CH₃ | OH | H | CH₃ | H |
| i-C₃H₇ | n-C₅H₁₁ | n-C₅H₁₁ | OH | H | CH₃ | H |
| i-C₃H₇ | n-C₆H₁₃ | n-C₆H₁₃ | OH | H | CH₃ | H |
| i-C₃H₇ | i-C₃H₇ | i-C₃H₇ | OH | H | CH₃ | H |
| i-C₃H₇ | i-C₄H₉ | i-C₄H₉ | OH | H | CH₃ | H |
| i-C₃H₇ | C₂H₄OH | C₂H₄OH | OH | H | CH₃ | H |
| i-C₃H₇ | —CH₂—CH(OH)—CH₃ | —CH₂—CH(OH)—CH₃ | OH | H | CH₃ | H |
| i-C₃H₇ | —CH₃ | C₂H₄OH | OH | H | CH₃ | H |
| i-C₃H₇ | —CH₂—CH₂—CH₂OH | —CH₂CH₂CH₂OH | OH | H | CH₃ | H |

TABLE IVB-continued

| R₁ | R₂ | R₃ | R₄ | R₅ | R₆ | R₇ |
|---|---|---|---|---|---|---|
| i-C₃H₇ | —CH₂—C₆H₅ | —CH₂—C₆H₅ | OH | H | CH₃ | H |
| i-C₃H₇ | —CH₂—CH₂—C₆H₅ | —CH₂—CH₂—C₆H₅ | OH | H | CH₃ | H |
| i-C₃H₇ | H |  (cyclopentyl) | OH | H | CH₃ | H |
| i-C₃H₇ | H |  (cyclohexyl) | OH | H | CH₃ | H |
| i-C₃H₇ | H |  (cycloheptyl) | OH | H | CH₃ | H |
| i-C₃H₇ | |  —COOH | OH | H | CH₃ | H |
| i-C₃H₇ | |  —CH₂—COOH | OH | H | CH₃ | H |
| i-C₃H₇ | |  —CH₂—CH₂—COOH | OH | H | CH₃ | H |
| i-C₃H₇ |  COOH | | OH | H | CH₃ | H |
| i-C₃H₇ |  COOH, OH | | OH | H | CH₃ | H |
| i-C₄H₉ | H | H | OH | H | CH₃ | H |
| i-C₄H₉ | H | CH₃ | OH | H | CH₃ | H |
| i-C₄H₉ | H | C₂H₅ | OH | H | CH₃ | H |
| i-C₄H₉ | H | n-C₃H₇ | OH | H | CH₃ | H |
| i-C₄H₉ | H | n-C₄H₉ | OH | H | CH₃ | H |
| i-C₄H₉ | H | i-C₃H₇ | OH | H | CH₃ | H |
| i-C₄H₉ | H | i-C₄H₉ | OH | H | CH₃ | H |
| i-C₄H₉ | H | n-C₅H₁₁ | OH | H | CH₃ | H |
| i-C₄H₉ | H | n-C₆H₁₃ | OH | H | CH₃ | H |
| i-C₄H₉ | H | C₂H₄OH | OH | H | CH₃ | H |
| i-C₄H₉ | H | —CH₂—CH(OH)—CH₃ | OH | H | CH₃ | H |
| i-C₄H₉ | H | —CH₂—CH₂—CH₂OH | OH | H | CH₃ | H |
| i-C₄H₉ | H | —CH₂—CH₂—N(CH₃)₂ | OH | H | CH₃ | H |
| i-C₄H₉ | H | —CH₂—CH₂—N(C₂H₅)₂ | OH | H | CH₃ | H |
| i-C₄H₉ | H | —CH₂—CH₂—N(C₄H₉)₂ | OH | H | CH₃ | H |
| i-C₄H₉ | H | —CH₂—CH₂—CH₂—N(CH₃)₂ | OH | H | CH₃ | H |
| i-C₄H₉ | H | —CH₂—CH₂—CH₂—N(C₂H₅)₂ | OH | H | CH₃ | H |
| i-C₄H₉ | H | —CH₂—CON(CH₃)₂ | OH | H | CH₃ | H |
| i-C₄H₉ | H | —CH₂—CH₂—CON(CH₃)₂ | OH | H | CH₃ | H |
| i-C₄H₉ | H | —CH₂—CON(C₂H₅)₂ | OH | H | CH₃ | H |
| i-C₄H₉ | H | —CH₂—C₆H₅ | OH | H | CH₃ | H |
| i-C₄H₉ | H | —CH₂—CH₂—C₆H₅ | OH | H | CH₃ | H |
| i-C₄H₉ | H | —CH₂—CH₂—N (pyrrolidino) | OH | H | CH₃ | H |
| i-C₄H₉ | H | —CH₂—CH₂—NO (morpholino) | OH | H | CH₃ | H |
| i-C₄H₉ | H | —CH₂—CH₂—N (piperidino) | OH | H | CH₃ | H |
| i-C₄H₉ | H | —CH₂—CH₂—N⌒N—CH₃ | OH | H | CH₃ | H |

TABLE IVB-continued

| R₁ | R₂ | R₃ | R₄ | R₅ | R₆ | R₇ |
|---|---|---|---|---|---|---|
| i-C₄H₉ | n-C₅H₁₁ | n-C₅H₁₁ | OH | H | CH₃ | H |
| i-C₄H₉ | n-C₆H₁₃ | n-C₆H₁₃ | OH | H | CH₃ | H |
| i-C₄H₉ | i-C₃H₇ | i-C₃H₇ | OH | H | CH₃ | H |
| i-C₄H₉ | i-C₄H₉ | i-C₄H₉ | OH | H | CH₃ | H |
| i-C₄H₉ | C₂H₄OH | C₂H₄OH | OH | H | CH₃ | H |
| i-C₄H₉ | —CH₂—CH(OH)—CH₃ | —CH₂—CH(OH)—CH₃ | OH | H | CH₃ | H |
| i-C₄H₉ | —CH₃ | C₂H₄OH | OH | H | CH₃ | H |
| i-C₄H₉ | —CH₂—CH₂—CH₂OH | —CH₂—CH₂—CH₂OH | OH | H | CH₃ | H |
| i-C₄H₉ | —CH₂—C₆H₅ | —CH₂—C₆H₅ | OH | H | CH₃ | H |
| i-C₄H₉ | —CH₂—CH₂—C₆H₅ | —CH₂—CH₂—C₆H₅ | OH | H | CH₃ | H |
| i-C₄H₉ | H | cyclopentyl | OH | H | CH₃ | H |
| i-C₄H₉ | H | cyclohexyl | OH | H | CH₃ | H |
| i-C₄H₉ | H | cycloheptyl | OH | H | CH₃ | H |
| i-C₄H₉ | | cyclohexyl-COOH | OH | H | CH₃ | H |
| i-C₄H₉ | | cyclohexyl-CH₂-COOH | OH | H | CH₃ | H |
| i-C₄H₉ | | cyclohexyl-CH₂-CH₂-COOH | OH | H | CH₃ | H |
| i-C₄H₉ | cyclopentyl-COOH | | OH | H | CH₃ | H |
| i-C₄H₉ | | cyclopentyl(COOH)(OH) | OH | H | CH₃ | H |
| sec.-C₄H₉ | H | H | OH | H | CH₃ | H |
| sec.-C₄H₉ | H | CH₃ | OH | H | CH₃ | H |
| sec.-C₄H₉ | H | C₂H₅ | OH | H | CH₃ | H |
| sec.-C₄H₉ | H | n-C₃H₇ | OH | H | CH₃ | H |
| sec.-C₄H₉ | H | n-C₄H₉ | OH | H | CH₃ | H |
| sec.-C₄H₉ | H | i-C₃H₇ | OH | H | CH₃ | H |
| sec.-C₄H₉ | H | i-C₄H₉ | OH | H | CH₃ | H |
| sec.-C₄H₉ | H | n-C₅H₁₁ | OH | H | CH₃ | H |
| sec.-C₄H₉ | H | n-C₆H₁₃ | OH | H | CH₃ | H |
| sec.-C₄H₉ | H | C₂H₄OH | OH | H | CH₃ | H |
| sec.-C₄H₉ | H | —CH₂—CH(OH)—CH₃ | OH | H | CH₃ | H |
| sec.-C₄H₉ | H | —CH₂—CH₂—CH₂OH | OH | H | CH₃ | H |
| sec.-C₄H₉ | H | —CH₂—CH₂—N(CH₃)₂ | OH | H | CH₃ | H |
| sec.-C₄H₉ | H | —CH₂—CH₂—N(C₂H₅)₂ | OH | H | CH₃ | H |
| sec.-C₄H₉ | H | —CH₂—CH₂—N(C₄H₉)₂ | OH | H | CH₃ | H |
| sec.-C₄H₉ | H | —CH₂—CH₂—CH₂N(CH₃)₂ | OH | H | CH₃ | H |
| sec.-C₄H₉ | H | —CH₂—CH₂—CH₂N(C₂H₅)₂ | OH | H | CH₃ | H |
| sec.-C₄H₉ | H | —CH₂—CON(CH₃)₂ | OH | H | CH₃ | H |
| sec.-C₄H₉ | H | —CH₂—CH₂—CON(CH₃)₂ | OH | H | CH₃ | H |
| sec.-C₄H₉ | H | —CH₂—CON(C₂H₅)₂ | OH | H | CH₃ | H |
| sec.-C₄H₉ | H | —CH₂—C₆H₅ | OH | H | CH₃ | H |
| sec.-C₄H₉ | H | —CH₂—CH₂—C₆H₅ | OH | H | CH₃ | H |
| sec.-C₄H₉ | H | —CH₂—CH₂—N(pyrrolidinyl) | OH | H | CH₃ | H |
| sec.-C₄H₉ | H | —CH₂—CH₂—N(morpholinyl) | OH | H | CH₃ | H |

TABLE IVB-continued

| R₁ | R₂ | R₃ | R₁ | R₅ | R₆ | R₇ |
|---|---|---|---|---|---|---|
| sec.-C₄H₉ | H | —CH₂—CH₂—N(piperidine) | OH | H | CH₃ | H |
| sec.-C₄H₉ | H | —CH₂—CH₂—N(N'-methylpiperazine)-CH₃ | OH | H | CH₃ | H |
| sec.-C₄H₉ | n-C₅H₁₁ | n-C₅H₁₁ | OH | H | CH₃ | H |
| sec.-C₄H₉ | n-C₆H₁₃ | n-C₆H₁₃ | OH | H | CH₃ | H |
| sec.-C₄H₉ | i-C₃H₇ | i-C₃H₇ | OH | H | CH₃ | H |
| sec.-C₄H₉ | i-C₄H₉ | i-C₄H₉ | OH | H | CH₃ | H |
| sec.-C₄H₉ | C₂H₄OH | C₂H₄OH | OH | H | CH₃ | H |
| sec.-C₄H₉ | —CH₂—CH(OH)—CH₃ | —CH₂—CH(OH)—CH₃ | OH | H | CH₃ | H |
| sec.-C₄H₉ | —CH₃ | C₂H₄OH | OH | H | CH₃ | H |
| sec.-C₄H₉ | —CH₂—CH₂—CH₂OH | —CH₂—CH₂—CH₂OH | OH | H | CH₃ | H |
| sec.-C₄H₉ | —CH₂—C₆H₅ | —CH₂—C₆H₅ | OH | H | CH₃ | H |
| sec.-C₄H₉ | —CH₂—CH₂—C₆H₅ | —CH₂—CH₂—C₆H₅ | OH | H | CH₃ | H |
| sec.-C₄H₉ | H | cyclopentyl | OH | H | CH₃ | H |
| sec.-C₄H₉ | H | cyclohexyl | OH | H | CH₃ | H |
| sec.-C₄H₉ | H | cycloheptyl | OH | H | CH₃ | H |
| sec.-C₄H₉ | cyclohexyl-COOH | | OH | H | CH₃ | H |
| sec.-C₄H₉ | cyclohexyl-CH₂-COOH | | OH | H | CH₃ | H |
| sec.-C₄H₉ | cyclohexyl-CH₂-CH₂-COOH | | OH | H | CH₃ | H |
| sec.-C₄H₉ | cyclopentyl-COOH | | OH | H | CH₃ | H |
| sec.-C₄H₉ | | cyclopentyl(COOH)(OH) | OH | H | CH₃ | H |

TABLE VA

| R₁ | R₂ | R₃ | R₄ | R₅ | R₆ | R₇ |
|---|---|---|---|---|---|---|
| CH₃ | CH₃ | CH₃ | H | OH | H | Cl |
| CH₃ | CH₃ | C₂H₅ | H | OH | H | Cl |
| CH₃ | C₂H₅ | C₂H₅ | H | OH | H | Cl |
| CH₃ | n-C₃H₇ | n-C₃H₇ | H | OH | H | Cl |
| CH₃ | n-C₄H₉ | n-C₄H₉ | H | OH | H | Cl |
| CH₃ | H | CH₂—COOH | H | OH | H | Cl |
| CH₃ | H | CH₂—COOC₂H₅ | H | OH | H | Cl |
| CH₃ | H | CH₃—CH(COOH) | H | OH | H | Cl |
| CH₃ | H | CH₃—CH(COOC₂H₅) | H | OH | H | Cl |
| CH₃ | H | —CH₂—CH₂—COOH | H | OH | H | Cl |
| CH₃ | H | —CH₂—CH₂—COOC₂H₅ | H | OH | H | Cl |

TABLE VA-continued

| R₁ | R₂ | R₃ | R₄ | R₅ | R₆ | R₇ |
|---|---|---|---|---|---|---|
| CH₃ | H | $-(CH_2)_4-CH(NH_2)-COOH$ | H | OH | H | Cl |
| CH₃ | cyclopentyl | | H | OH | H | Cl |
| CH₃ | cyclohexyl | | H | OH | H | Cl |
| CH₃ | | morpholino | H | OH | H | Cl |
| CH₃ | | piperidino | H | OH | H | Cl |
| CH₃ | | N-CH₃ piperazino | H | OH | H | Cl |
| CH₃ | | N-C₂H₅ piperazino | H | OH | H | Cl |
| CH₃ | | N-C₂H₅OH piperazino | H | OH | H | Cl |
| C₂H₅ | CH₃ | CH₃ | H | OH | H | Cl |
| C₂H₅ | CH₃ | C₂H₅ | H | OH | H | Cl |
| C₂H₅ | C₂H₅ | C₂H₅ | H | OH | H | Cl |
| C₂H₅ | n-C₃H₇ | n-C₃H₇ | H | OH | H | Cl |
| C₂H₅ | n-C₄H₉ | n-C₄H₉ | H | OH | H | Cl |
| C₂H₅ | H | CH₂—COOH | H | OH | H | Cl |
| C₂H₅ | H | CH₂—COOC₂H₅ | H | OH | H | Cl |
| C₂H₅ | H | CH₃—CH(—)—COOH | H | OH | H | Cl |
| C₂H₅ | H | CH₃—CH(—)—COOC₂H₅ | H | OH | H | Cl |
| C₂H₅ | H | —CH₂—CH₂—COOH | H | OH | H | Cl |
| C₂H₅ | H | —CH₂—CH₂—COOC₂H₅ | H | OH | H | Cl |
| C₂H₅ | H | $-(CH_2)_4-CH(NH_2)-COOH$ | H | OH | H | Cl |
| C₂H₅ | cyclopentyl | | H | OH | H | Cl |
| C₂H₅ | cyclohexyl | | H | OH | H | Cl |
| C₂H₅ | | morpholino | H | OH | H | Cl |
| C₂H₅ | | piperidino | H | OH | H | Cl |
| C₂H₅ | | N-CH₃ piperazino | H | OH | H | Cl |
| C₂H₅ | | N-C₂H₅ piperazino | H | OH | H | Cl |
| C₂H₅ | | N-C₂H₅OH piperazino | H | OH | H | Cl |

TABLE VA-continued

| R₁ | R₂ | R₃ | R₄ | R₅ | R₆ | R₇ |
|---|---|---|---|---|---|---|
| n-C₃H₇ | CH₃ | CH₃ | H | OH | H | Cl |
| n-C₃H₇ | CH₃ | C₂H₅ | H | OH | H | Cl |
| n-C₃H₇ | C₂H₅ | C₂H₅ | H | OH | H | Cl |
| n-C₃H₇ | n-C₃H₇ | n-C₃H₇ | H | OH | H | Cl |
| n-C₃H₇ | n-C₄H₉ | n-C₄H₉ | H | OH | H | Cl |
| n-C₃H₇ | H | CH₂—COOH | H | OH | H | Cl |
| n-C₃H₇ | H | CH₂—COOC₂H₅ | H | OH | H | Cl |
| n-C₃H₇ | H | CH₃—CH—COOH | H | OH | H | Cl |
| n-C₃H₇ | H | CH₃—CH—COOC₂H₅ | H | OH | H | Cl |
| n-C₃H₇ | H | —CH₂—CH₂—COOH | H | OH | H | Cl |
| n-C₃H₇ | H | —CH₂—CH₂—COOC₂H₅ | H | OH | H | Cl |
| n-C₃H₇ | H | —(CH₂)₄—CH(NH₂)—COOH | H | OH | H | Cl |
| n-C₃H₇ |  (cyclopentyl, spanning R₂–R₃) | | H | OH | H | Cl |
| n-C₃H₇ |  (cyclohexyl, spanning R₂–R₃) | | H | OH | H | Cl |
| n-C₃H₇ |  (morpholino, spanning R₂–R₃) | | H | OH | H | Cl |
| n-C₃H₇ |  (piperidino, spanning R₂–R₃) | | H | OH | H | Cl |
| n-C₃H₇ | 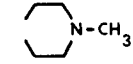 (N-CH₃ piperazino, spanning R₂–R₃) | | H | OH | H | Cl |
| n-C₃H₇ | 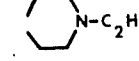 (N-C₂H₅ piperazino, spanning R₂–R₃) | | H | OH | H | Cl |
| n-C₃H₇ | 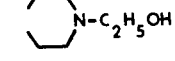 (N-C₂H₅OH piperazino, spanning R₂–R₃) | | H | OH | H | Cl |
| n-C₄H₉ | CH₃ | CH₃ | H | OH | H | Cl |
| n-C₄H₉ | CH₃ | C₂H₅ | H | OH | H | Cl |
| n-C₄H₉ | C₂H₅ | C₂H₅ | H | OH | H | Cl |
| n-C₄H₉ | n-C₃H₇ | n-C₃H₇ | H | OH | H | Cl |
| n-C₄H₉ | n-C₄H₉ | n-C₄H₉ | H | OH | H | Cl |
| n-C₄H₉ | H | CH₂—COOH | H | OH | H | Cl |
| n-C₄H₉ | H | CH₂—COOC₂H₅ | H | OH | H | Cl |
| n-C₄H₉ | H | CH₃—CH—COOH | H | OH | H | Cl |
| n-C₄H₉ | H | CH₃—CH—COOC₂H₅ | H | OH | H | Cl |
| n-C₄H₉ | H | —CH₂—CH₂—COOH | H | OH | H | Cl |
| n-C₄H₉ | H | —CH₂—CH₂—COOC₂H₅ | H | OH | H | Cl |
| n-C₄H₉ | H | —(CH₂)₄—CH(NH₂)—COOH | H | OH | H | Cl |
| n-C₄H₉ |  (cyclopentyl, spanning R₂–R₃) | | H | OH | H | Cl |
| n-C₄H₉ |  (cyclohexyl, spanning R₂–R₃) | | H | OH | H | Cl |
| n-C₄H₉ |  (morpholino, spanning R₂–R₃) | | H | OH | H | Cl |
| n-C₄H₉ |  (piperidino, spanning R₂–R₃) | | H | OH | H | Cl |

TABLE VA-continued

| $R_1$ | $R_2$ | $R_3$ | $R_4$ | $R_5$ | $R_6$ | $R_7$ |
|---|---|---|---|---|---|---|
| n-$C_4H_9$ | | piperidine-N-$CH_3$ | H | OH | H | Cl |
| n-$C_4H_9$ | | piperidine-N-$C_2H_5$ | H | OH | H | Cl |
| n-$C_4H_9$ | | piperidine-N-$C_2H_5OH$ | H | OH | H | Cl |

TABLE VB

| $R_1$ | $R_2$ | $R_3$ | $R_4$ | $R_5$ | $R_6$ | $R_7$ |
|---|---|---|---|---|---|---|
| $CH_3$ | H | H | H | OH | H | Cl |
| $CH_3$ | H | $CH_3$ | H | OH | H | Cl |
| $CH_3$ | H | $C_2H_5$ | H | OH | H | Cl |
| $CH_3$ | H | n-$C_3H_7$ | H | OH | H | Cl |
| $CH_3$ | H | n-$C_4H_9$ | H | OH | H | Cl |
| $CH_3$ | H | i-$C_3H_7$ | H | OH | H | Cl |
| $CH_3$ | H | i-$C_4H_9$ | H | OH | H | Cl |
| $CH_3$ | H | n-$C_5H_{11}$ | H | OH | H | Cl |
| $CH_3$ | H | n-$C_6H_{13}$ | H | OH | H | Cl |
| $CH_3$ | H | $C_2H_4OH$ | H | OH | H | Cl |
| $CH_3$ | H | $-CH_2-CH(OH)-CH_3$ | H | OH | H | Cl |
| $CH_3$ | H | $-CH_2-CH_2-CH_2OH$ | H | OH | H | Cl |
| $CH_3$ | H | $-CH_2-CH_2-N(CH_3)_2$ | H | OH | H | Cl |
| $CH_3$ | H | $-CH_2-CH_2-N(C_2H_5)_2$ | H | OH | H | Cl |
| $CH_3$ | H | $-CH_2-CH_2-N(C_4H_9)_2$ | H | OH | H | Cl |
| $CH_3$ | H | $-CH_2-CH_2-CH_2-N(CH_3)_2$ | H | OH | H | Cl |
| $CH_3$ | H | $-CH_2-CH_2-CH_2-N(C_2H_5)_2$ | H | OH | H | Cl |
| $CH_3$ | H | $-CH_2-CON(CH_3)_2$ | H | OH | H | Cl |
| $CH_3$ | H | $-CH_2-CH_2-CON(CH_3)_2$ | H | OH | H | Cl |
| $CH_3$ | H | $-CH_2-CON(C_2H_5)_2$ | H | OH | H | Cl |
| $CH_3$ | H | $-CH_2-C_6H_5$ | H | OH | H | Cl |
| $CH_3$ | H | $-CH_2-CH_2-C_6H_5$ | H | OH | H | Cl |
| $CH_3$ | H | $-CH_2-CH_2-N$(pyrrolidine) | H | OH | H | Cl |
| $CH_3$ | H | $-CH_2-CH_2-N$(morpholine) | H | OH | H | Cl |
| $CH_3$ | H | $-CH_2-CH_2-N$(piperidine) | H | OH | H | Cl |
| $CH_3$ | H | $-CH_2-CH_2-N$(N-methylpiperazine)$-CH_3$ | H | OH | H | Cl |
| $CH_3$ | n-$C_5H_{11}$ | n-$C_5H_{11}$ | H | OH | H | Cl |
| $CH_3$ | n-$C_6H_{13}$ | n-$C_6H_{13}$ | H | OH | H | Cl |
| $CH_3$ | i-$C_3H_7$ | i-$C_3H_7$ | H | OH | H | Cl |
| $CH_3$ | i-$C_4H_9$ | i-$C_4H_9$ | H | OH | H | Cl |
| $CH_3$ | $C_2H_4OH$ | $C_2H_4OH$ | H | OH | H | Cl |
| $CH_3$ | $-CH_2-CH(OH)-CH_3$ | $-CH_2-CH(OH)-CH_3$ | H | OH | H | Cl |
| $CH_3$ | $-CH_3$ | $C_2H_4OH$ | H | OH | H | Cl |
| $CH_3$ | $-CH_2-CH_2-CH_2OH$ | $-CH_2-CH_2-CH_2OH$ | H | OH | H | Cl |
| $CH_3$ | $-CH_2-C_6H_5$ | $-CH_2-C_6H_5$ | H | OH | H | Cl |
| $CH_3$ | $-CH_2-CH_2-C_6H_5$ | $-CH_2-CH_2-C_6H_5$ | H | OH | H | Cl |
| $CH_3$ | H | cyclopentyl | H | OH | H | Cl |
| $CH_3$ | H | cyclohexyl | H | OH | H | Cl |

TABLE VB-continued

| R₁ | R₂ | R₃ | R₄ | R₅ | R₆ | R₇ |
|---|---|---|---|---|---|---|
| CH₃ | H |  | H | OH | H | Cl |
| CH₃ | |  —COOH | H | OH | H | Cl |
| CH₃ | |  —CH₂—COOH | H | OH | H | Cl |
| CH₃ | |  —CH₂—CH₂—COOH | H | OH | H | Cl |
| CH₃ |  | | H | OH | H | Cl |
| CH₃ | | 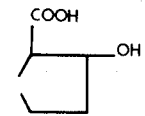 | H | OH | H | Cl |
| C₂H₅ | H | H | H | OH | H | Cl |
| C₂H₅ | H | CH₃ | H | OH | H | Cl |
| C₂H₅ | H | C₂H₅ | H | OH | H | Cl |
| C₂H₅ | H | n-C₃H₇ | H | OH | H | Cl |
| C₂H₅ | H | n-C₄H₉ | H | OH | H | Cl |
| C₂H₅ | H | i-C₃H₇ | H | OH | H | Cl |
| C₂H₅ | H | i-C₄H₉ | H | OH | H | Cl |
| C₂H₅ | H | n-C₅H₁₁ | H | OH | H | Cl |
| C₂H₅ | H | n-C₆H₁₃ | H | OH | H | Cl |
| C₂H₅ | H | C₂H₄OH | H | OH | H | Cl |
| C₂H₅ | H | —CH₂—CH—CH₃<br>        \|<br>        OH | H | OH | H | Cl |
| C₂H₅ | H | —CH₂—CH₂—CH₂OH | H | OH | H | Cl |
| C₂H₅ | H | —CH₂—CH₂—N(CH₃)₂ | H | OH | H | Cl |
| C₂H₅ | H | —CH₂—CH₂—N(C₂H₅)₂ | H | OH | H | Cl |
| C₂H₅ | H | —CH₂—CH₂—N(C₄H₉)₂ | H | OH | H | Cl |
| C₂H₅ | H | —CH₂—CH₂—CH₂—N(CH₃)₂ | H | OH | H | Cl |
| C₂H₅ | H | —CH₂—CH₂—CH₂—N(C₂H₅)₂ | H | OH | H | Cl |
| C₂H₅ | H | —CH₂—CON(CH₃)₂ | H | OH | H | Cl |
| C₂H₅ | H | —CH₂—CH₂—CON(CH₃)₂ | H | OH | H | Cl |
| C₂H₅ | H | —CH₂—CON(C₂H₅)₂ | H | OH | H | Cl |
| C₂H₅ | H | —CH₂—C₆H₅ | H | OH | H | Cl |
| C₂H₅ | H | —CH₂—CH₂—C₆H₅ | H | OH | H | Cl |
| C₂H₅ | H | 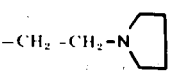 | H | OH | H | Cl |
| C₂H₅ | H | 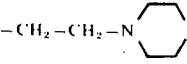 | H | OH | H | Cl |
| C₂H₅ | H | 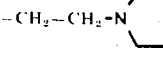 | H | OH | H | Cl |
| C₂H₅ | H | 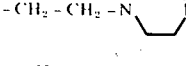 | H | OH | H | Cl |
| C₂H₅ | n-C₅H₁₁ | n-C₅H₁₁ | H | OH | H | Cl |
| C₂H₅ | n-C₆H₁₃ | n-C₆H₁₃ | H | OH | H | Cl |
| C₂H₅ | i-C₃H₇ | i-C₃H₇ | H | OH | H | Cl |
| C₂H₅ | i-C₄H₉ | i-C₄H₉ | H | OH | H | Cl |
| C₂H₅ | C₂H₄OH | C₂H₄OH | H | OH | H | Cl |
| C₂H₅ | —CH₂—CH—CH₃<br>        \|<br>        OH | —CH₂—CH—CH<br>        \|<br>        OH | H | OH | H | Cl |
| C₂H₅ | —CH₃ | C₂H₄OH | H | OH | H | Cl |
| C₂H₅ | —CH₂—CH₂—CH₂OH | —CH₂—CH₂—CH₂OH | H | OH | H | Cl |
| C₂H₅ | —CH₂—C₆H₅ | —CH₂—C₆H₅ | H | OH | H | Cl |
| C₂H₅ | —CH₂—CH₂—C₆H₅ | —CH₂—CH₂—C₆H₅ | H | OH | H | Cl |

TABLE VB-continued

| R₁ | R₂ | R₃ | R₄ | R₅ | R₆ | R₇ |
|---|---|---|---|---|---|---|
| C₂H₅ | H |  (cyclopentyl) | H | OH | H | Cl |
| C₂H₅ | H |  (cyclohexyl) | H | OH | H | Cl |
| C₂H₅ | H |  (cycloheptyl) | H | OH | H | Cl |
| C₂H₅ | 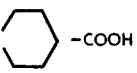 —COOH | | H | OH | H | Cl |
| C₂H₅ | 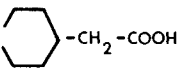 —CH₂—COOH | | H | OH | H | Cl |
| C₂H₅ | 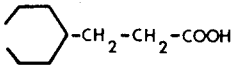 —CH₂—CH₂—COOH | | H | OH | H | Cl |
| C₂H₅ |  (cyclopentyl-COOH) | | H | OH | H | Cl |
| C₂H₅ | | 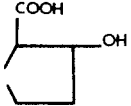 (cyclopentyl with COOH and OH) | H | OH | H | Cl |
| n-C₃H₇ | H | H | H | OH | H | Cl |
| n-C₃H₇ | H | CH₃ | H | OH | H | Cl |
| n-C₃H₇ | H | C₂H₅ | H | OH | H | Cl |
| n-C₃H₇ | H | n-C₃H₇ | H | OH | H | Cl |
| n-C₃H₇ | H | n-C₄H₉ | H | OH | H | Cl |
| n-C₃H₇ | H | i-C₃H₇ | H | OH | H | Cl |
| n-C₃H₇ | H | i-C₄H₉ | H | OH | H | Cl |
| n-C₃H₇ | H | n-C₅H₁₁ | H | OH | H | Cl |
| n-C₃H₇ | H | n-C₆H₁₃ | H | OH | H | Cl |
| n-C₃H₇ | H | C₂H₄OH | H | OH | H | Cl |
| n-C₃H₇ | H | —CH₂—CH(OH)—CH₃ | H | OH | H | Cl |
| n-C₃H₇ | H | —CH₂CH₂—CH₂OH | H | OH | H | Cl |
| n-C₃H₇ | H | —CH₂CH₂—N(CH₃)₂ | H | OH | H | Cl |
| n-C₃H₇ | H | —CH₂—CH₂—N(C₂H₅)₂ | H | OH | H | Cl |
| n-C₃H₇ | H | —CH₂—CH₂—N(C₄H₉)₂ | H | OH | H | Cl |
| n-C₃H₇ | H | —CH₂—CH₂—CH₂—N(CH₃)₂ | H | OH | H | Cl |
| n-C₃H₇ | H | —CH₂—CH₂—CH₂—N(C₂H₅)₂ | H | OH | H | Cl |
| n-C₃H₇ | H | —CH₂—CON(CH₃)₂ | H | OH | H | Cl |
| n-C₃H₇ | H | —CH₂—CH₂—CON(CH₃)₂ | H | OH | H | Cl |
| n-C₃H₇ | H | —CH₂—CON(C₂H₅)₂ | H | OH | H | Cl |
| n-C₃H₇ | H | —CH₂—C₆H₅ | H | OH | H | Cl |
| n-C₃H₇ | H | —CH₂—CH₂—C₆H₅ | H | OH | H | Cl |
| n-C₃H₇ | H | —CH₂—CH₂—N (pyrrolidine) | H | OH | H | Cl |
| n-C₃H₇ | H | —CH₂—CH₂—N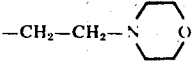O (morpholine) | H | OH | H | Cl |
| n-C₃H₇ | H | —CH₂—CH₂—N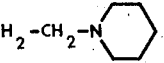 (piperidine) | H | OH | H | Cl |
| n-C₃H₇ | H | —CH₂—CH₂—NN—CH₃ (N-methylpiperazine) | H | OH | H | Cl |
| n-C₃H₇ | n-C₅H₁₁ | n-C₅H₁₁ | H | OH | H | Cl |
| n-C₃H₇ | n-C₆H₁₃ | n-C₆H₁₃ | H | OH | H | Cl |
| n-C₃H₇ | i-C₃H₇ | i-C₃H₇ | H | OH | H | Cl |
| n-C₃H₇ | i-C₄H₉ | i-C₄H₉ | H | OH | H | Cl |
| n-C₃H₇ | C₂H₄OH | C₂H₄OH | H | OH | H | Cl |

TABLE VB-continued

| R₁ | R₂ | R₃ | R₄ | R₅ | R₆ | R₇ |
|---|---|---|---|---|---|---|
| n-C₃H₇ | —CH₂—CH—CH₃<br>          \|<br>         OH | —CH₂—CH—CH₃<br>          \|<br>         OH | H | OH | H | Cl |
| n-C₃H₇ | —CH₃ | C₂H₄OH | H | OH | H | Cl |
| n-C₃H₇ | —CH₂—CH₂—CH₂OH | —CH₂—CH₂—CH₂OH | H | OH | H | Cl |
| n-C₃H₇ | —CH₂—C₆H₅ | —CH₂—C₆H₅ | H | OH | H | Cl |
| n-C₃H₇ | —CH₂—CH₂—C₆H₅ | —CH₂—CH₂—C₆H₅ | H | OH | H | Cl |
| n-C₃H₇ | H |  | H | OH | H | Cl |
| n-C₃H₇ | H |  | H | OH | H | Cl |
| n-C₃H₇ | H |  | H | OH | H | Cl |
| n-C₃H₇ | 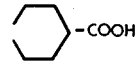 | | H | OH | H | Cl |
| n-C₃H₇ | 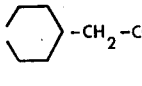 | | H | OH | H | Cl |
| n-C₃H₇ | 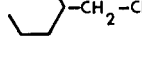 | | H | OH | H | Cl |
| n-C₃H₇ |  | | H | OH | H | Cl |
| n-C₃H₇ | 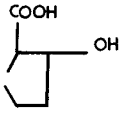 | | H | OH | H | Cl |
| n-C₄H₉ | H | H | H | OH | H | Cl |
| n-C₄H₉ | H | CH₃ | H | OH | H | Cl |
| n-C₄H₉ | H | C₂H₅ | H | OH | H | Cl |
| n-C₄H₉ | H | n-C₃H₇ | H | OH | H | Cl |
| n-C₄H₉ | H | n-C₄H₉ | H | OH | H | Cl |
| n-C₄H₉ | H | i-C₃H₇ | H | OH | H | Cl |
| n-C₄H₉ | H | i-C₄H₉ | H | OH | H | Cl |
| n-C₄H₉ | H | n-C₅H₁₁ | H | OH | H | Cl |
| n-C₄H₉ | H | n-C₆H₁₃ | H | OH | H | Cl |
| n-C₄H₉ | H | C₂H₄OH | H | OH | H | Cl |
| n-C₄H₉ | H | —CH₂—CH—CH₃<br>          \|<br>         OH | H | OH | H | Cl |
| n-C₄H₉ | H | —CH₂—CH₂—CH₂OH | H | OH | H | Cl |
| n-C₄H₉ | H | —CH₂—CH₂—N(CH₃)₂ | H | OH | H | Cl |
| n-C₄H₉ | H | —CH₂—CH₂—N(C₂H₅)₂ | H | OH | H | Cl |
| n-C₄H₉ | H | —CH₂—CH₂—N(C₄H₉)₂ | H | OH | H | Cl |
| n-C₄H₉ | H | —CH₂—CH₂—CH₂—N(CH₂)₂ | H | OH | H | Cl |
| n-C₄H₉ | H | —CH₂—CH₂—CH₂—N(C₂H₅)₂ | H | OH | H | Cl |
| n-C₄H₉ | H | —CH₂—CON(CH₃)₂ | H | OH | H | Cl |
| n-C₄H₉ | H | —CH₂—CH₂—CON(CH₃)₂ | H | OH | H | Cl |
| n-C₄H₉ | H | —CH₂—CON(C₂H₅)₂ | H | OH | H | Cl |
| n-C₄H₉ | H | —CH₂—C₆H₅ | H | OH | H | Cl |
| n-C₄H₉ | H | —CH₂—CH₂—C₆H₅ | H | OH | H | Cl |
| n-C₄H₉ | H | 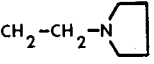 | H | OH | H | Cl |
| n-C₄H₉ | H | 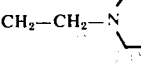 | H | OH | H | Cl |

TABLE VB-continued

| R₁ | R₂ | R₃ | R₄ | R₅ | R₆ | R₇ |
|---|---|---|---|---|---|---|
| n-C₄H₉ | H | —CH₂—CH₂—N(piperidinyl) | H | OH | H | Cl |
| n-C₄H₉ | H | —CH₂—CH₂—N(piperazinyl)N—CH₃ | H | OH | H | Cl |
| n-C₄H₉ | n-C₅H₁₁ | n-C₅H₁₁ | H | OH | H | Cl |
| n-C₄H₉ | n-C₆H₁₃ | n-C₆H₁₃ | H | OH | H | Cl |
| n-C₄H₉ | i-C₃H₇ | i-C₃H₇ | H | OH | H | Cl |
| n-C₄H₉ | i-C₄H₉ | i-C₄H₉ | H | OH | H | Cl |
| n-C₄H₉ | C₂H₄OH | C₂H₄OH | H | OH | H | Cl |
| n-C₄H₉ | —CH₂—CH(OH)—CH₃ | —CH₂—CH(OH)—CH₃ | H | OH | H | Cl |
| n-C₄H₉ | —CH₃ | C₂H₄OH | H | OH | H | Cl |
| n-C₄H₉ | —CH₂—CH₂—CH₂OH | —CH₂—CH₂—CH₂OH | H | OH | H | Cl |
| n-C₄H₉ | —CH₂—C₆H₅ | —CH₂—C₆H₅ | H | OH | H | Cl |
| n-C₄H₉ | —CH₂—CH₂—C₆H₅ | —CH₂—CH₂—C₆H₅ | H | OH | H | Cl |
| n-C₄H₉ | H | cyclopentyl | H | OH | H | Cl |
| n-C₄H₉ | H | cyclohexyl | H | OH | H | Cl |
| n-C₄H₉ | H | cycloheptyl | H | OH | H | Cl |
| n-C₄H₉ |  | cyclohexyl-COOH | H | OH | H | Cl |
| n-C₄H₉ |  | cyclohexyl-CH₂-COOH | H | OH | H | Cl |
| n-C₄H₉ |  | cyclohexyl-CH₂-CH₂-COOH | H | OH | H | Cl |
| n-C₄H₉ |  | cyclopentyl-COOH | H | OH | H | Cl |
| n-C₄H₉ |  | cyclohexyl(COOH)(OH) | H | OH | H | Cl |
| i-C₃H₇ | H | H | H | OH | H | Cl |
| i-C₃H₇ | H | CH₃ | H | OH | H | Cl |
| i-C₃H₇ | H | C₂H₅ | H | OH | H | Cl |
| i-C₃H₇ | H | n-C₃H₇ | H | OH | H | Cl |
| i-C₃H₇ | H | n-C₄H₉ | H | OH | H | Cl |
| i-C₃H₇ | H | i-C₃H₇ | H | OH | H | Cl |
| i-C₃H₇ | H | i-C₄H₉ | H | OH | H | Cl |
| i-C₃H₇ | H | n-C₅H₁₁ | H | OH | H | Cl |
| i-C₃H₇ | H | n-C₆H₁₃ | H | OH | H | Cl |
| i-C₃H₇ | H | C₂H₄OH | H | OH | H | Cl |
| i-C₃H₇ | H | —CH₂—CH(OH)—CH₃ | H | OH | H | Cl |
| i-C₃H₇ | H | —CH₂—CH₂—CH₂OH | H | OH | H | Cl |
| i-C₃H₇ | H | —CH₂—CH₂—N(CH₃)₂ | H | OH | H | Cl |
| i-C₃H₇ | H | —CH₂—CH₂—N(C₂H₅)₂ | H | OH | H | Cl |
| i-C₃H₇ | H | —CH₂—CH₂—N(C₄H₉)₂ | H | OH | H | Cl |
| i-C₃H₇ | H | —CH₂—CH₂—CH₂—N(CH₃)₂ | H | OH | H | Cl |
| i-C₃H₇ | H | —CH₂—CH₂—CH₂—N(C₂H₅)₂ | H | OH | H | Cl |
| i-C₃H₇ | H | —CH₂—CON(CH₃)₂ | H | OH | H | Cl |
| i-C₃H₇ | H | —CH₂—CH₂—CON(CH₃)₂ | H | OH | H | Cl |
| i-C₃H₇ | H | —CH₂—CON(C₂H₅)₂ | H | OH | H | Cl |
| i-C₃H₇ | H | —CH₂—C₆H₅ | H | OH | H | Cl |
| i-C₃H₇ | H | —CH₂—CH₂—C₆H₅ | H | OH | H | Cl |

TABLE VB-continued

| R₁ | R₂ | R₃ | R₄ | R₅ | R₆ | R₇ |
|---|---|---|---|---|---|---|
| i-C₃H₇ | H | −CH₂−CH₂−N | H | OH | H | Cl |
| i-C₃H₇ | H | −CH₂−CH₂−NO | H | OH | H | Cl |
| i-C₃H₇ | H | −CH₂−CH₂−N | H | OH | H | Cl |
| i-C₃H₇ | H | −CH₂−CH₂−NN−CH₃ | H | OH | H | Cl |
| i-C₃H₇ | n-C₅H₁₁ | n-C₅H₁₁ | H | OH | H | Cl |
| i-C₃H₇ | n-C₆H₁₃ | n-C₆H₁₃ | H | OH | H | Cl |
| i-C₃H₇ | i-C₃H₇ | i-C₃H₇ | H | OH | H | Cl |
| i-C₃H₇ | i-C₄H₉ | i-C₄H₉ | H | OH | H | Cl |
| i-C₃H₇ | C₂H₄OH | C₂H₄OH | H | OH | H | Cl |
| i-C₃H₇ | −CH₂−CH−CH₃<br>        OH | −CH₂−CH−CH₃<br>        OH | H | OH | H | Cl |
| i-C₃H₇ | −CH₃ | C₂H₄OH | H | OH | H | Cl |
| i-C₃H₇ | −CH₂−CH₂−CH₂OH | −CH₂−CH₂−CH₂OH | H | OH | H | Cl |
| i-C₃H₇ | −CH₂−C₆H₅ | −CH₂−C₆H₅ | H | OH | H | Cl |
| i-C₃H₇ | −CH₂−CH₂−C₆H₅ | −CH₂−CH₂−C₆H₅ | H | OH | H | Cl |
| i-C₃H₇ | H |  | H | OH | H | Cl |
| i-C₃H₇ | H |  | H | OH | H | Cl |
| i-C₃H₇ | H |  | H | OH | H | Cl |
| i-C₃H₇ | | 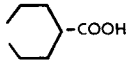-COOH | H | OH | H | Cl |
| i-C₃H₇ | | 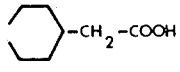-CH₂-COOH | H | OH | H | Cl |
| i-C₃H₇ | | 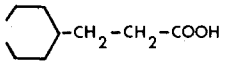-CH₂-CH₂-COOH | H | OH | H | Cl |
| i-C₃H₇ | COOH | | H | OH | H | Cl |
| i-C₃H₇ | | 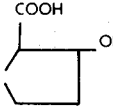 | H | OH | H | Cl |
| i-C₄H₉ | H | H | H | OH | H | Cl |
| i-C₄H₉ | H | CH₃ | H | OH | H | Cl |
| i-C₄H₉ | H | C₂H₅ | H | OH | H | Cl |
| i-C₄H₉ | H | n-C₃H₇ | H | OH | H | Cl |
| i-C₄H₉ | H | n-C₄H₉ | H | OH | H | Cl |
| i-C₄H₉ | H | i-C₃H₇ | H | OH | H | Cl |
| i-C₄H₉ | H | i-C₄H₉ | H | OH | H | Cl |
| i-C₄H₉ | H | n-C₅H₁₁ | H | OH | H | Cl |
| i-C₄H₉ | H | n-C₆H₁₃ | H | OH | H | Cl |
| i-C₄H₉ | H | C₂H₄OH | H | OH | H | Cl |
| i-C₄H₉ | H | −CH₂−CH−CH₃<br>        OH | H | OH | H | Cl |
| i-C₄H₉ | H | −CH₂−CH₂−CH₂OH | H | OH | H | Cl |
| i-C₄H₉ | H | −CH₂−CH₂−N(CH₃)₂ | H | OH | H | Cl |
| i-C₄H₉ | H | −CH₂−CH₂−N(C₂H₅)₂ | H | OH | H | Cl |

TABLE VB-continued

| R₁ | R₂ | R₃ | R₄ | R₅ | R₆ | R₇ |
|---|---|---|---|---|---|---|
| i-C₄H₉ | H | —CH₂—CH₂—N(C₄H₉)₂ | H | OH | H | Cl |
| i-C₄H₉ | H | —CH₂—CH₂—CH₂—N(CH₃)₂ | H | OH | H | Cl |
| i-C₄H₉ | H | —CH₂—CH₂—CH₂—N(C₂H₅)₂ | H | OH | H | Cl |
| i-C₄H₉ | H | —CH₂—CON(CH₃)₂ | H | OH | H | Cl |
| i-C₄H₉ | H | —CH₂—CH₂—CON(CH₃)₂ | H | OH | H | Cl |
| i-C₄H₉ | H | —CH₂—CON(C₂H₅)₂ | H | OH | H | Cl |
| i-C₄H₉ | H | —CH₂—C₆H₅ | H | OH | H | Cl |
| i-C₄H₉ | H | —CH₂—CH₂—C₆H₅ | H | OH | H | Cl |
| i-C₄H₉ | H | —CH₂—CH₂—N(pyrrolidinyl) | H | OH | H | Cl |
| i-C₄H₉ | N | —CH₂—CH₂—N(morpholinyl) | H | OH | H | Cl |
| i-C₄H₉ | H | —CH₂—CH₂—N(piperidinyl) | H | OH | H | Cl |
| i-C₄H₉ | H | —CH₂—CH₂—N(N′-methylpiperazinyl) | H | OH | H | Cl |
| i-C₄H₉ | n-C₅H₁₁ | n-C₅H₁₁ | H | OH | H | Cl |
| i-C₄H₉ | n-C₆H₁₃ | n-C₆H₁₃ | H | OH | H | Cl |
| i-C₄H₉ | i-C₃H₇ | i-C₃H₇ | H | OH | H | Cl |
| i-C₄H₉ | i-C₄H₉ | i-C₄H₉ | H | OH | H | Cl |
| i-C₄H₉ | C₂H₄OH | C₂H₄OH | H | OH | H | Cl |
| i-C₄H₉ | —CH₂—CH(OH)—CH₃ | —CH₂—CH(OH)—CH₃ | H | OH | H | Cl |
| i-C₄H₉ | —CH₃ | C₂H₄OH | H | OH | H | Cl |
| i-C₄H₉ | —CH₂—CH₂—CH₂OH | —CH₂—CH₂—CH₂OH | H | OH | H | Cl |
| i-C₄H₉ | —CH₂—C₆H₅ | —CH₂—C₆H₅ | H | OH | H | Cl |
| i-C₄H₉ | —CH₂—CH₂—C₆H₅ | —CH₂—CH₂—C₆H₅ | H | OH | H | Cl |
| i-C₄H₉ | H | cyclopentyl | H | OH | H | Cl |
| i-C₄H₉ | H | cyclohexyl | H | OH | H | Cl |
| i-C₄H₉ | H | cycloheptyl | H | OH | H | Cl |
| i-C₄H₉ | cyclohexyl—COOH | | H | OH | H | Cl |
| i-C₄H₉ | cyclohexyl—CH₂—COOH | | H | OH | H | Cl |
| i-C₄H₉ | cyclohexyl—CH₂—CH₂—COOH | | H | OH | H | Cl |
| i-C₄H₉ | cyclopentyl—COOH | | H | OH | H | Cl |
| i-C₄H₉ | cyclohexyl(COOH)(OH) | | H | OH | H | Cl |
| sec.-C₄H₉ | H | H | H | OH | H | Cl |
| sec.-C₄H₉ | H | CH₃ | H | OH | H | Cl |
| sec.-C₄H₉ | H | C₂H₅ | H | OH | H | Cl |
| sec.-C₄H₉ | H | n-C₃H₇ | H | OH | H | Cl |
| sec.-C₄H₉ | H | n-C₄H₉ | H | OH | H | Cl |
| sec.-C₄H₉ | H | i-C₃H₇ | H | OH | H | Cl |
| sec.-C₄H₉ | H | i-C₄H₉ | H | OH | H | Cl |

TABLE VB-continued

| R₁ | R₂ | R₃ | R₄ | R₅ | R₆ | R₇ |
|---|---|---|---|---|---|---|
| sec.-C₄H₉ | H | n-C₅H₁₁ | H | OH | H | Cl |
| sec.-C₄H₉ | H | n-C₆H₁₃ | H | OH | H | Cl |
| sec.-C₄H₉ | H | C₂H₄OH | H | OH | H | Cl |
| sec.-C₄H₉ | H | —CH₂—CH(OH)—CH₃ | H | OH | H | Cl |
| sec.-C₄H₉ | H | —CH₂—CH₂—CH₂OH | H | OH | H | Cl |
| sec.-C₄H₉ | H | —CH₂—CH₂—N(CH₃)₂ | H | OH | H | Cl |
| sec.-C₄H₉ | H | —CH₂—CH₂—N(C₂H₅)₂ | H | OH | H | Cl |
| sec.-C₄H₉ | H | —CH₂—CH₂—N(C₄H₉)₂ | H | OH | H | Cl |
| sec.-C₄H₉ | H | —CH₂—CH₂—CH₂—N(CH₃)₂ | H | OH | H | Cl |
| sec.-C₄H₉ | H | —CH₂—CH₂—CH₂—N(C₂H₅)₂ | H | OH | H | Cl |
| sec.-C₄H₉ | H | —CH₂—CON(CH₃)₂ | H | OH | H | Cl |
| sec.-C₄H₉ | H | —CH₂—CH₂—CON(CH₃)₂ | H | OH | H | Cl |
| sec.-C₄H₉ | H | —CH₂—CON(C₂H₅)₂ | H | OH | H | Cl |
| sec.-C₄H₉ | H | —CH₂—C₆H₅ | H | OH | H | Cl |
| sec.-C₄H₉ | H | —CH₂—CH₂—C₆H₅ | H | OH | H | Cl |
| sec.-C₄H₉ | H | —CH₂—CH₂—N(pyrrolidine) | H | OH | H | Cl |
| sec.-C₄H₉ | H | —CH₂—CH₂—N(morpholine) | H | OH | H | Cl |
| sec.-C₄H₉ | H | —CH₂—CH₂—N(piperidine) | H | OH | H | Cl |
| sec.-C₄H₉ | H | —CH₂—CH₂—N(piperazine)—CH₃ | H | OH | H | Cl |
| sec.-C₄H₉ | n-C₅H₁₁ | n-C₅H₁₁ | H | OH | H | Cl |
| sec.-C₄H₉ | n-C₆H₁₃ | n-C₆H₁₃ | H | OH | H | Cl |
| sec.-C₄H₉ | i-C₃H₇ | i-C₃H₇ | H | OH | H | Cl |
| sec.-C₄H₉ | i-C₄H₉ | i-C₄H₉ | H | OH | H | Cl |
| sec.-C₄H₉ | C₂H₄OH | C₂H₄OH | H | OH | H | Cl |
| sec.-C₄H₉ | —CH₂—CH(OH)—CH₃ | —CH₂—CH(OH)—CH₃ | H | OH | H | Cl |
| sec.-C₄H₉ | —CH₃ | C₂H₄OH | H | OH | H | Cl |
| sec.-C₄H₉ | —CH₂—CH₂—CH₂OH | —CH₂—CH₂—CH₂OH | H | OH | H | Cl |
| sec.-C₄H₉ | —CH₂—C₆H₅ | —CH₂—C₆H₅ | H | OH | H | Cl |
| sec.-C₄H₉ | —CH₂—CH₂—C₆H₅ | —CH₂—CH₂—C₆H₅ | H | OH | H | Cl |
| sec.-C₄H₉ | H | cyclopentyl | H | OH | H | Cl |
| sec.-C₄H₉ | H | cyclohexyl | H | OH | H | Cl |
| sec.-C₄H₉ | H | cycloheptyl | H | OH | H | Cl |
| sec.-C₄H₉ | | cyclohexyl-COOH | H | OH | H | Cl |
| sec.-C₄H₉ | | cyclohexyl-CH₂-COOH | H | OH | H | Cl |
| sec.-C₄H₉ | | cyclohexyl-CH₂-CH₂-COOH | H | OH | H | Cl |
| sec.-C₄H₉ | | cyclopentyl-COOH | H | OH | H | Cl |
| sec.-C₄H₉ | | cyclopentyl(COOH)(OH) | H | OH | H | Cl |

Further examples of compounds to be prepared according to the invention are the following substituted tetracyclines:

TABLE VIa

| $R_1$ | $R_2$ | $R_3$ | $R_4$ | $R_5$ | $R_6$ | $R_7$ |
|---|---|---|---|---|---|---|
| $CH_3$ | $CH_3$ | $CH_3$ | H | OH | H | H |
| $CH_3$ | $CH_3$ | $C_2H_5$ | H | OH | H | H |
| $CH_3$ | $C_2H_5$ | $C_2H_5$ | H | OH | H | H |
| $CH_3$ | $n\text{-}C_3H_7$ | $n\text{-}C_3H_7$ | H | OH | H | H |
| $CH_3$ | $n\text{-}C_4H_9$ | $n\text{-}C_4H_9$ | H | OH | H | H |
| $CH_3$ | H | $CH_2\text{—}COOH$ | H | OH | H | H |
| $CH_3$ | H | $CH_2\text{—}COOC_2H_5$ | H | OH | H | H |
| $CH_3$ | H | $CH_3\text{—}CH(\text{—}COOH)$ | H | OH | H | H |
| $CH_3$ | H | $CH_3\text{—}CH(\text{—}COOC_2H_5)$ | H | OH | H | H |
| $CH_3$ | H | $\text{—}CH_2\text{—}CH_2\text{—}COOH$ | H | OH | H | H |
| $CH_3$ | H | $\text{—}CH_2\text{—}CH_2\text{—}COOC_2H_5$ | H | OH | H | H |
| $CH_3$ | H | $\text{—}(CH_2)_4\text{—}CH(NH_2)\text{—}COOH$ | H | OH | H | H |
| $CH_3$ | \multicolumn{2}{l|}{} | H | OH | H | H |
| $CH_3$ | \multicolumn{2}{l|}{} | H | OH | H | H |
| $CH_3$ | \multicolumn{2}{l|}{} | H | OH | H | H |
| $CH_3$ | \multicolumn{2}{l|}{} | H | OH | H | H |
| $CH_3$ | \multicolumn{2}{l|}{} | H | OH | H | H |
| $CH_3$ | \multicolumn{2}{l|}{} | H | OH | H | H |
| $CH_3$ | \multicolumn{2}{l|}{} | H | OH | H | H |
| $C_2H_5$ | $CH_3$ | $CH_3$ | H | OH | H | H |
| $C_2H_5$ | $CH_3$ | $C_2H_5$ | H | OH | H | H |
| $C_2H_5$ | $C_2H_5$ | $C_2H_5$ | H | OH | H | H |
| $C_2H_5$ | $n\text{-}C_3H_7$ | $n\text{-}C_3H_7$ | H | OH | H | H |
| $C_2H_5$ | $n\text{-}C_4H_9$ | $n\text{-}C_4H_9$ | H | OH | H | H |
| $C_2H_5$ | H | $CH_2\text{—}COOH$ | H | OH | H | H |
| $C_2H_5$ | H | $CH_2\text{—}COOC_2H_5$ | H | OH | H | H |
| $C_2H_5$ | H | $CH_3\text{—}CH(\text{—}COOH)$ | H | OH | H | H |
| $C_2H_5$ | H | $CH_3\text{—}CH(\text{—}COOC_2H_5)$ | H | OH | H | H |
| $C_2H_5$ | H | $\text{—}CH_2\text{—}CH_2\text{—}COOH$ | H | OH | H | H |
| $C_2H_5$ | H | $\text{—}CH_2\text{—}CH_2\text{—}COOC_2H_5$ | H | OH | H | H |
| $C_2H_5$ | H | $\text{—}(CH_2)_4\text{—}CH(NH_2)\text{—}COOH$ | H | OH | H | H |
| $C_2H_5$ | \multicolumn{2}{l|}{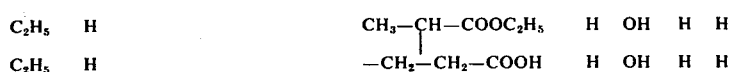} | H | OH | H | H |
| $C_2H_5$ | \multicolumn{2}{l|}{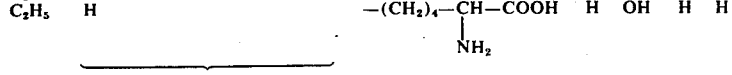} | H | OH | H | H |

TABLE VIa-continued

| R₁ | R₂ | R₃ | R₄ | R₅ | R₆ | R₇ |
|---|---|---|---|---|---|---|
| C₂H₅ |  | | H | OH | H | H |
| C₂H₅ |  | | H | OH | H | H |
| C₂H₅ |  | | H | OH | H | H |
| C₂H₅ | N—CH₃ | | H | OH | H | H |
| C₂H₅ | N—C₂H₅ | | H | OH | H | H |
| C₂H₅ | N—C₂H₅OH | | H | OH | H | H |
| n-C₃H₇ | CH₃ | CH₃ | H | OH | H | H |
| n-C₃H₇ | CH₃ | C₂H₅ | H | OH | H | H |
| n-C₃H₇ | C₂H₅ | C₂H₅ | H | OH | H | H |
| n-C₃H₇ | n-C₃H₇ | n-C₃H₇ | H | OH | H | H |
| n-C₃H₇ | n-C₄H₉ | n-C₄H₉ | H | OH | H | H |
| n-C₃H₇ | H | CH₂—COOH | H | OH | H | H |
| n-C₃H₇ | H | CH₂—COOC₂H₅ | H | OH | H | H |
| n-C₃H₇ | H | CH₃—CH—COOH | H | OH | H | H |
| n-C₃H₇ | H | CH₃—CH—COOC₂H₅ | H | OH | H | H |
| n-C₃H₇ | H | —CH₂—CH₂—COOH | H | OH | H | H |
| n-C₃H₇ | H | —CH₂—CH₂—COOC₂H₅ | H | OH | H | H |
| n-C₃H₇ | H | —(CH₂)₄—CH—COOH<br>                 NH₂ | H | OH | H | H |
| n-C₃H₇ | 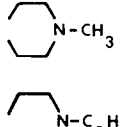 | | H | OH | H | H |
| n-C₃H₇ | 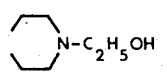 | | H | OH | H | H |
| n-C₃H₇ |  | | H | OH | H | H |
| n-C₃H₇ |  | | H | OH | H | H |
| n-C₃H₇ | N—CH₃ | | H | OH | H | H |
| n-C₃H₇ | N—C₂H₅ | | H | OH | H | H |
| n-C₃H₇ | N—C₂H₅OH | | H | OH | H | H |
| n-C₄H₉ | CH₃ | CH₃ | H | OH | H | H |
| n-C₄H₉ | CH₃ | C₂H₅ | H | OH | H | H |
| n-C₄H₉ | C₂H₅ | C₂H₅ | H | OH | H | H |
| n-C₄H₉ | n-C₃H₇ | n-C₃H₇ | H | OH | H | H |
| n-C₄H₉ | n-C₄H₉ | n-C₄H₉ | H | OH | H | H |
| n-C₄H₉ | H | CH₂—COOH | H | OH | H | H |
| n-C₄H₉ | H | CH₂—COOC₂H₅ | H | OH | H | H |

TABLE VIa-continued

| R₁ | R₂ | R₃ | R₄ | R₅ | R₆ | R₇ |
|---|---|---|---|---|---|---|
| n-C₄H₉ | H | CH₃—CH—COOH <br> \| | H | OH | H | H |
| n-C₄H₉ | H | CH₃—CH—COOC₂H₅ <br> \| | H | OH | H | H |
| n-C₄H₉ | H | —CH₂—CH₂—COOH | H | OH | H | H |
| n-C₄H₉ | H | —CH₂—CH₂—COOC₂H₅ | H | OH | H | H |
| n-C₄H₉ | H | —(CH₂)₄—CH—COOH <br>               NH₂ | H | OH | H | H |
| n-C₄H₉ |  | | H | OH | H | H |
| n-C₄H₉ |  | | H | OH | H | H |
| n-C₄H₉ |  | | H | OH | H | H |
| n-C₄H₉ |  | | H | OH | H | H |
| n-C₄H₉ | 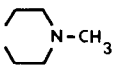 | | H | OH | H | H |
| n-C₄H₉ | 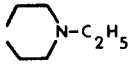 | | H | OH | H | H |
| n-C₄H₉ | 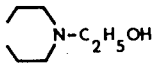 | | H | OH | H | H |

TABLE VIb

| R₁ | R₂ | R₃ | R₄ | R₅ | R₆ | R₇ |
|---|---|---|---|---|---|---|
| CH₃ | CH₃ | CH₃ | H | H | H | —N(CH₃)₂ |
| CH₃ | CH₃ | C₂H₅ | H | H | H | —N(CH₃)₂ |
| CH₃ | C₂H₅ | C₂H₅ | H | H | H | —N(CH₃)₂ |
| CH₃ | n-C₃H₇ | n-C₃H₇ | H | H | H | —N(CH₃)₂ |
| CH₃ | n-C₄H₉ | n-C₄H₉ | H | H | H | —N(CH₃)₂ |
| CH₃ | H | CH₂—COOH | H | H | H | —N(CH₃)₂ |
| CH₃ | H | CH₂—COOC₂H₅ | H | H | H | —N(CH₃)₂ |
| CH₃ | H | CH₃—CH—COOH <br> \| | H | H | H | —N(CH₃)₂ |
| CH₃ | H | CH₃—CH—COOC₂H₅ <br> \| | H | H | H | —N(CH₃)₂ |
| CH₃ | H | —CH₂—CH₂—COOH | H | H | H | —N(CH₃)₂ |
| CH₃ | H | —CH₂—CH₂—COOC₂H₅ | H | H | H | —N(CH₃)₂ |
| CH₃ | H | —(CH₂)₄—CH—COOH <br>               NH₂ | H | H | H | —N(CH₃)₂ |
| CH₃ |  | | H | H | H | —N(CH₃)₂ |
| CH₃ |  | | H | H | H | —N(CH₃)₂ |
| CH₃ |  | | H | H | H | —N(CH₃)₂ |

TABLE VIb-continued

| R₁ | R₂ | R₃ | R₄ | R₅ | R₆ | R₇ |
|---|---|---|---|---|---|---|
| $CH_3$ | |  | H | H | H | $-N(CH_3)_2$ |
| $CH_3$ | | 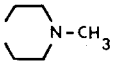 | H | H | H | $-N(CH_3)_2$ |
| $CH_3$ | | 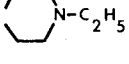 | H | H | H | $-N(CH_3)_2$ |
| $CH_3$ | | 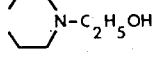 | H | H | H | $-N(CH_3)_2$ |
| $C_2H_5$ | $CH_3$ | $CH_3$ | H | H | H | $-N(CH_3)_2$ |
| $C_2H_5$ | $CH_3$ | $C_2H_5$ | H | H | H | $-N(CH_3)_2$ |
| $C_2H_5$ | $C_2H_5$ | $C_2H_5$ | H | H | H | $-N(CH_3)_2$ |
| $C_2H_5$ | $n-C_3H_7$ | $n-C_3H_7$ | H | H | H | $-N(CH_3)_2$ |
| $C_2H_5$ | $n-C_3H_9$ | $n-C_4H_9$ | H | H | H | $-N(CH_3)_2$ |
| $C_2H_5$ | H | $CH_2-COOH$ | H | H | H | $-N(CH_3)_2$ |
| $C_2H_5$ | H | $CH_2-COOC_2H_5$ | H | H | H | $-N(CH_3)_2$ |
| $C_2H_5$ | H | $CH_3-\underset{|}{C}H-COOH$ | H | H | H | $-N(CH_3)_2$ |
| $C_2H_5$ | H | $CH_3-\underset{|}{C}H-COOC_2H_5$ | H | H | H | $-N(CH_3)_2$ |
| $C_2H_5$ | H | $-CH_2-CH_2-COOH$ | H | H | H | $-N(CH_3)_2$ |
| $C_2H_5$ | H | $-CH_2-CH_2-COOC_2H_5$ | H | H | H | $-N(CH_3)_2$ |
| $C_2H_5$ | H | $-(CH_2)_1-\underset{\underset{NH_2}{|}}{C}H-COOH$ | H | H | H | $-N(CH_3)_2$ |
| $C_2H_5$ | |  | H | H | H | $-N(CH_3)_2$ |
| $C_2H_5$ | |  | H | H | H | $-N(CH_3)_2$ |
| $C_2H_5$ | |  | H | H | H | $-N(CH_3)_2$ |
| $C_2H_5$ | |  | H | H | H | $-N(CH_3)_2$ |
| $C_2H_5$ | | 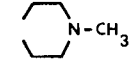 | H | H | H | $-N(CH_3)_2$ |
| $C_2H_5$ | | 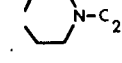 | H | H | H | $-N(CH_3)_2$ |
| $C_2H_5$ | | 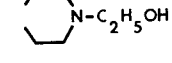 | H | H | H | $-N(CH_3)_2$ |
| $n-C_3H_7$ | $CH_3$ | $CH_3$ | H | H | H | $-N(CH_3)_2$ |
| $n-C_3H_7$ | $CH_3$ | $C_2H_5$ | H | H | H | $-N(CH_3)_2$ |
| $n-C_3H_7$ | $C_2H_5$ | $C_2H_5$ | H | H | H | $-N(CH_3)_2$ |
| $n-C_3H_7$ | $n-C_3H_7$ | $n-C_3H_7$ | H | H | H | $-N(CH_3)_2$ |
| $n-C_3H_7$ | $n-C_4H_9$ | $n-C_4H_9$ | H | H | H | $-N(CH_3)_2$ |
| $n-C_3H_7$ | H | $CH_2-COOH$ | H | H | H | $-N(CH_3)_2$ |
| $n-C_3H_7$ | H | $CH_2-COOC_2H_5$ | H | H | H | $-N(CH_3)_2$ |
| $n-C_3H_7$ | H | $CH_3-\underset{|}{C}H-COOH$ | H | H | H | $-N(CH_3)_2$ |
| $n-C_3H_7$ | H | $CH_3-\underset{|}{C}H-COOC_2H_5$ | H | H | H | $-N(CH_3)_2$ |
| $n-C_3H_7$ | H | $-CH_2-CH_2-COOH$ | H | H | H | $-N(CH_3)_2$ |
| $n-C_3H_7$ | H | $-CH_2-CH_2-COOC_2H_5$ | H | H | H | $-N(CH_3)_2$ |

TABLE VIb-continued

| R₁ | R₂ | R₃ | R₄ | R₅ | R₆ | R₇ |
|---|---|---|---|---|---|---|
| n-C₃H₇ | H | —(CH₂)₄—CH(NH₂)—COOH | H | H | H | —N(CH₃)₂ |
| n-C₃H₇ | \<cyclopentyl ring spanning R₂,R₃\> | | H | H | H | —N(CH₃)₂ |
| n-C₃H₇ | \<cyclohexyl ring spanning R₂,R₃\> | | H | H | H | —N(CH₃)₂ |
| n-C₃H₇ | \<morpholino ring spanning R₂,R₃\> | | H | H | H | —N(CH₃)₂ |
| n-C₃H₇ | \<piperidino ring spanning R₂,R₃\> | | H | H | H | —N(CH₃)₂ |
| n-C₃H₇ | \<N-CH₃ piperazino ring\> | | H | H | H | —N(CH₃)₂ |
| n-C₃H₇ | \<N-C₂H₅ piperazino ring\> | | H | H | H | —N(CH₃)₂ |
| n-C₃H₇ | \<N-C₂H₅OH piperazino ring\> | | H | H | H | —N(CH₃)₂ |
| n-C₄H₉ | CH₃ | CH₃ | H | H | H | —N(CH₃)₂ |
| n-C₄H₉ | CH₃ | C₂H₅ | H | H | H | —N(CH₃)₂ |
| n-C₄H₉ | C₂H₅ | C₂H₅ | H | H | H | —N(CH₃)₂ |
| n-C₄H₉ | n-C₃H₇ | n-C₃H₇ | H | H | H | —N(CH₃)₂ |
| n-C₄H₉ | n-C₄H₉ | n-C₄H₉ | H | H | H | —N(CH₃)₂ |
| n-C₄H₉ | H | CH₂—COOH | H | H | H | —N(CH₃)₂ |
| n-C₄H₉ | H | CH₂—COOC₂H₅ | H | H | H | —N(CH₃)₂ |
| n-C₄H₉ | H | CH₃—CH—COOH | H | H | H | —N(CH₃)₂ |
| n-C₄H₉ | H | CH₃—CH—COOC₂H₅ | H | H | H | —N(CH₃)₂ |
| n-C₄H₉ | H | —CH₂—CH₂—COOH | H | H | H | —N(CH₃)₂ |
| n-C₄H₉ | H | —CH₂—CH₂—COOC₂H₅ | H | H | H | —N(CH₃)₂ |
| n-C₄H₉ | H | —(CH₂)₄—CH(NH₂)—COOH | H | H | H | —N(CH₃)₂ |
| n-C₄H₉ | \<cyclopentyl ring spanning R₂,R₃\> | | H | H | H | —N(CH₃)₂ |
| n-C₄H₉ | \<cyclohexyl ring spanning R₂,R₃\> | | H | H | H | —N(CH₃)₂ |
| n-C₄H₉ | \<morpholino ring spanning R₂,R₃\> | | H | H | H | —N(CH₃)₂ |
| n-C₄H₉ | \<piperidino ring spanning R₂,R₃\> | | H | H | H | —N(CH₃)₂ |
| n-C₄H₉ | \<N-CH₃ piperazino ring\> | | H | H | H | —N(CH₃)₂ |
| n-C₄H₉ | \<N-C₂H₅ piperazino ring\> | | H | H | H | —N(CH₃)₂ |
| n-C₄H₉ | \<N-C₂H₅OH piperazino ring\> | | H | H | H | —N(CH₃)₂ |

TABLE VIc

| R₁ | R₂ | R₃ | R₄ | R₅ | R₆ | R₇ |
|---|---|---|---|---|---|---|
| CH₃ | CH₃ | CH₃ | OH | | =CH₂ | H |
| CH₃ | CH₃ | C₂H₅ | OH | | =CH₂ | H |
| CH₃ | C₂H₅ | C₂H₅ | OH | | =CH₂ | H |
| CH₃ | n-C₃H₇ | n-C₃H₇ | OH | | =CH₂ | H |
| CH₃ | n-C₄H₉ | n-C₄H₉ | OH | | =CH₂ | H |
| CH₃ | H | CH₂—COOH | OH | | =CH₂ | H |
| CH₃ | H | CH₂—COOC₂H₅ | OH | | =CH₂ | H |
| CH₃ | H | CH₃—CH(—)—COOH | OH | | =CH₂ | H |
| CH₃ | H | CH₃—CH(—)—COOC₂H₅ | OH | | =CH₂ | H |
| CH₃ | H | —CH₂—CH₂—COOH | OH | | =CH₂ | H |
| CH₃ | H | —CH₂—CH₂—COOC₂H₅ | OH | | =CH₂ | H |
| CH₃ | H | —(CH₂)₄—CH(NH₂)—COOH | OH | | =CH₂ | H |
| CH₃ | R₂ and R₃ form cyclopentyl  | | OH | | =CH₂ | H |
| CH₃ | R₂ and R₃ form cyclohexyl  | | OH | | =CH₂ | H |
| CH₃ | R₂ and R₃ form tetrahydropyranyl (O)  | | OH | | =CH₂ | H |
| CH₃ | R₂ and R₃ form piperidinyl (NH)  | | OH | | =CH₂ | H |
| CH₃ | R₂ and R₃ form N-CH₃ piperidinyl 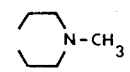 | | OH | | =CH₂ | H |
| CH₃ | R₂ and R₃ form N-C₂H₅ piperidinyl 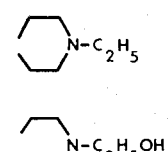 | | OH | | =CH₂ | H |
| CH₃ | R₂ and R₃ form N-C₂H₅OH piperidinyl  | | OH | | =CH₂ | H |
| C₂H₅ | CH₃ | CH₃ | OH | | =CH₂ | H |
| C₂H₅ | CH₃ | C₂H₅ | OH | | =CH₂ | H |
| C₂H₅ | C₂H₅ | C₂H₅ | OH | | =CH₂ | H |
| C₂H₅ | n-C₃H₇ | n-C₃H₇ | OH | | =CH₂ | H |
| C₂H₅ | n-C₄H₉ | n-C₄H₉ | OH | | =CH₂ | H |
| C₂H₅ | H | CH₂—COOH | OH | | =CH₂ | H |
| C₂H₅ | H | CH₂—COOC₂H₅ | OH | | =CH₂ | H |
| C₂H₅ | H | CH₃—CH(—)—COOH | OH | | =CH₂ | H |
| C₂H₅ | H | CH₃—CH(—)—COOC₂H₅ | OH | | =CH₂ | H |
| C₂H₅ | H | —CH₂—CH₂—COOH | OH | | =CH₂ | H |
| C₂H₅ | H | —CH₂—CH₂—COOC₂H₅ | OH | | =CH₂ | H |
| C₂H₅ | H | —(CH₂)₄—CH(NH₂)—COOH | OH | | =CH₂ | H |
| C₂H₅ | R₂ and R₃ form cyclopentyl  | | OH | | =CH₂ | H |
| C₂H₅ | R₂ and R₃ form cyclohexyl | | OH | | =CH₂ | H |

TABLE VIc-continued

| $R_1$ | $R_2$ | $R_3$ | $R_4$ | $R_5$ | $R_6$ | $R_7$ |
|---|---|---|---|---|---|---|
| $C_2H_5$ | | morpholinyl (6-ring with O) | | OH | $=CH_2$ | H |
| $C_2H_5$ | | piperidinyl (6-ring with N) | | OH | $=CH_2$ | H |
| $C_2H_5$ | | N-methylpiperazinyl | | OH | $=CH_2$ | H |
| $C_2H_5$ | | N-ethylpiperazinyl | | OH | $=CH_2$ | H |
| $C_2H_5$ | | N-($C_2H_5OH$)piperazinyl | | OH | $=CH_2$ | H |
| n-$C_3H_7$ | $CH_3$ | $CH_3$ | OH | $=CH_2$ | H |
| n-$C_3H_7$ | $CH_3$ | $C_2H_5$ | OH | $=CH_2$ | H |
| n-$C_3H_7$ | $C_2H_5$ | $C_2H_5$ | OH | $=CH_2$ | H |
| n-$C_3H_7$ | n-$C_3H_7$ | n-$C_3H_7$ | OH | $=CH_2$ | H |
| n-$C_3H_7$ | n-$C_4H_9$ | n-$C_4H_9$ | OH | $=CH_2$ | H |
| n-$C_3H_7$ | H | $CH_2-COOH$ | OH | $=CH_2$ | H |
| n-$C_3H_7$ | H | $CH_2-COOC_2H_5$ | OH | $=CH_2$ | H |
| n-$C_3H_7$ | H | $CH_3-CH(-)-COOH$ | OH | $=CH_2$ | H |
| n-$C_3H_7$ | H | $CH_3-CH(-)-COOC_2H_5$ | OH | $=CH_2$ | H |
| n-$C_3H_7$ | H | $-CH_2-CH_2-COOH$ | OH | $=CH_2$ | H |
| n-$C_3H_7$ | H | $-CH_2-CH_2-COOC_2H_5$ | OH | $=CH_2$ | H |
| n-$C_3H_7$ | H | $-(CH_2)_4-CH(NH_2)-COOH$ | OH | $=CH_2$ | H |
| n-$C_3H_7$ | | cyclopentyl (5-ring) | | OH | $=CH_2$ | H |
| n-$C_3H_7$ | | cyclohexyl (6-ring) | | OH | $=CH_2$ | H |
| n-$C_3H_7$ | | morpholinyl (6-ring with O) | | OH | $=CH_2$ | H |
| n-$C_3H_7$ | | piperidinyl (6-ring with N) | | OH | $=CH_2$ | H |
| n-$C_3H_7$ | | N-methylpiperazinyl | | OH | $=CH_2$ | H |
| n-$C_3H_7$ | | N-ethylpiperazinyl | | OH | $=CH_2$ | H |
| n-$C_3H_7$ | | N-($C_2H_5OH$)piperazinyl | | OH | $=CH_2$ | H |
| n-$C_4H_9$ | $CH_3$ | $CH_3$ | OH | $=CH_2$ | H |
| n-$C_4H_9$ | $CH_3$ | $C_2H_5$ | OH | $=CH_2$ | H |
| n-$C_4H_9$ | $C_2H_5$ | $C_2H_5$ | OH | $=CH_2$ | H |
| n-$C_4H_9$ | n-$C_3H_7$ | n-$C_3H_7$ | OH | $=CH_2$ | H |
| n-$C_4H_9$ | n-$C_4H_9$ | n-$C_4H_9$ | OH | $=CH_2$ | H |
| n-$C_4H_9$ | H | $CH_2-COOH$ | OH | $=CH_2$ | H |
| n-$C_4H_9$ | H | $CH_2-COOC_2H_5$ | OH | $=CH_2$ | H |
| n-$C_4H_9$ | H | $CH_3-CH(-)-COOH$ | OH | $=CH_2$ | H |
| n-$C_4H_9$ | H | $CH_3-CH(-)-COOC_2H_5$ | OH | $=CH_2$ | H |

TABLE VIc-continued

| R₁ | R₂ | R₃ | R₄ | R₅ | R₆ | R₇ |
|---|---|---|---|---|---|---|
| n-C₄H₉ | H | —CH₂—CH₂—COOH | OH | | =CH₂ | H |
| n-C₄H₉ | H | —CH₂—CH₂—COOC₂H₅ | OH | | =CH₂ | H |
| n-C₄H₉ | H | —(CH₂)₄—CH—COOH<br>                          \|<br>                         NH₂ | OH | | =CH₂ | H |
| n-C₄H₉ | |  (pyrrolidinyl) | | OH | =CH₂ | H |
| n-C₄H₉ | |  (piperidinyl) | | OH | =CH₂ | H |
| n-C₄H₉ | |  (morpholinyl, O) | | OH | =CH₂ | H |
| n-C₄H₉ | |  (piperazinyl, N) | | OH | =CH₂ | H |
| n-C₄H₉ | | 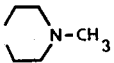 N–CH₃ | | OH | =CH₂ | H |
| n-C₄H₉ | | 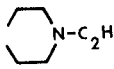 N–C₂H₅ | | OH | =CH₂ | H |
| n-C₄H₉ | | 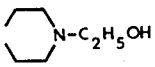 N–C₂H₅OH | | OH | =CH₂ | H |

The following Examples illustrate the invention:

EXAMPLE 1

N-(1-ethoxycarbonyl-1-dimethylamino-methyl)-tetracycline 4.4 Grams of tetracycline base were dissolved in 100 ml of chloroform and 3.2 g of ethyl semiacetal of ethyl glyoxylate and 2 ml of liquified dimethylamine were added. The mixture was refluxed for 3 hours, concentrated by evaporation in vacuo, and the residue was dissolved in about 20 ml of ethyl acetate. Precipitation with diisopropyl ether, suction-filtration and drying at greatly reduced pressure at room temperature yielded N-(1-ethoxycarbonyl-1-dimethylamino-methyl)-tetracycline which started decomposing at 130°C.

Yield: 3.5 grams, C₂₈H₃₄N₃O₁₀ . H₂O (590.6), Calculated: C 57.0 H 6.2 N 7.1 found: C 57.0 H 6.9 N 7.3.

The same result was obtained using 2.2 g of ethyl glyoxylate.

The following compounds (Examples 2 to 8) were prepared in an alalogous manner. All the melting points given are decomposition points.

The $R_f$-values were determined on thin-layer chromatography plates manufactured by Messrs. E. Merck-/Darmstadt, F.R.G. (cellulose/0.1N hydrochloric acid). The $R_f$-values were generally higher than those of the starting tetracyclines.

EXAMPLE 2

N-(1-n-butoxycarbonyl-1-dimethylamino-methyl)-tetracycline

Melting point: 103°C; $R_f$-value = 0.78, C₃₀H₃₉N₃O₁₀ . H₂O (619.6), calculated: C 58.2 H 6.7 N 6.8 O 28.4, found: C 58.7 H 7.0 N 6.1 O 27.9.

EXAMPLE 3

N-(1-ethoxycarbonyl-1-pyrrolidyl(1)-methyl)-tetracycline

Melting point: 157°C, C₃₀H₃₇N₃O₁₀ (598.6), calculated: C 60.0 H 6.1 N 7.0, found: C 59.6 H 6.9 N 7.3.

EXAMPLE 4

N-(1-n-butoxycarbonyl-1-pyrrolidyl(1)-methyl)-tetracycline

Melting point: 97°C; $R_f$-value = 0.81, C₃₂H₄₁N₃O₁₀ . H₂O (645.6), calculated: C 59.5 H 6.7 N 6.5, found: C 60.0 H 7.4 N 6.3.

EXAMPLE 5

N-(1-ethoxycarbonyl-1-piperidyl(1)-methyl)-tetracycline

Melting point: 130°C; $R_f$-value = 0.82, C₃₁H₃₉N₃O₁₀ (613.7), calculated: C 60.7 H 6.4 N 6.9, found: C 60.5 H 6.9 N 7.1.

In the H¹-NMR (in CDCl₃), this compound showed, besides other typical absorption values, a characteristical absorption at 5.1 ppm for

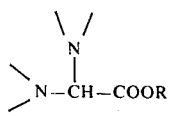

EXAMPLE 6

N-(1-n-butoxycarbonyl-1-piperidyl(1)-methyl)-tetracycline

Melting point: 110°C; $R_f$-value = 0.70, $C_{33}H_{43}N_3O_{10}$ . $H_2O$ (659.6), calculated: C 60.1 H 6.9 N 6.4 O 26.7, found: C 59.5 H 7.3 N 5.8 O 27.6.

EXAMPLE 7

N-(1-ethoxycarbonyl-1-morpholinyl(4)-methyl)-tetracycline

Melting point: 135°–145°C ''; $R_f$-value = 0.70, $C_{30}H_{37}N_3O_{11}$ . $H_2O$ (633.6), calculated: C 56.8 H 6.2 N 6.6, found: C 56.8 H 6.5 N 6.6.

EXAMPLE 8

N-[1-ethoxycarbonyl-1-(4-β-hydroxyethyl-piperazyl(1)-methyl]-tetracycline

Melting point: 133°–137°C, $C_{32}H_{42}N_4O_{11}$ . $H_2O$ (676.7), calculated: C 56.8 H 6.7 N 8.3, found: C 56.8 H 7.0 N 8.7.

EXAMPLE 9

N-(1-ethoxycarbonyl-1-dimethylamino-methyl)-oxytetracycline

4 Grams of the ethyl semiacetal of ethyl glyoxylate and 2 ml of liquified dimethylamine were dissolved in 100 ml of dimethylformamide, and after 15 minutes 4.6 g of oxytetracycline base were added. The limpid solution was stirred for 5 hours at room temperature under nitrogen and then concentrated by evaporation at greatly reduced pressure and at a maximum temperature of 50°C. The oily residue was dissolved in about 30 ml of ethyl acetate, filtered and the reaction product was precipitated with diisopropyl ether.

Upon drying at room temperature under greatly reduced pressure, 2.5 g of N-(1-ethoxycarbonyl-1-dimethylamino-methyl)-oxytetracycline were obtained; decomposition point 105°C; $R_f$-value = 0.79.

In an analogous manner, the compounds indicated in Examples 10 to 13 were prepared.

EXAMPLE 10

N-(1-n-butoxycarbonyl-1-dimethylamino-methyl)-oxytetracycline

Melting point: 105°–108°C; $R_f$-value = 0.76, $C_{30}H_{39}N_3O_{11}$ . $H_2O$ (635.7), calculated: C 56.7 H 6.5 N 6.6, found: C 56.4 H 7.0 N 6.2.

EXAMPLE 11

N-(1-ethoxycarbonyl-1-pyrrolidyl(1)-methyl)-oxytetracycline

Melting point: 150°C, $C_{30}H_{37}N_3O_{11}$ . $H_2O$ (633.7), calculated: C 57.0 H 6.2 N 6.6, found: C 56.7 H 6.3 N 6.8.

EXAMPLE 12

N-(1-butoxycarbonyl-1-pyrrolidyl(1)-methyl)-oxytetracycline

Melting point: 86°–90°C, $C_{32}H_{41}N_3O_{11}$ (643.7), calculated: C 59.7 H 6.4 N 6.5, found: C 59.4 H 6.7 N 6.3.

EXAMPLE 13

N-(1-ethoxycarbonyl-1-piperidyl(1)-methyl)-oxytetracycline

Melting point: 160°C; $R_f$-value = 0.81, $C_{31}H_{37}N_3O_{11}$ . $H_2O$ (645.7), calculated: C 57.7 H 6.1 N 6.5, found: C 57.6 H 6.7 N 6.4.

In the $H^1$-NMR (in $CDCl_3$), the compound showed, besides other typical absorption values, a characteristical absorption at 5.1 ppm for

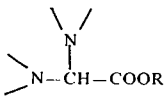

EXAMPLE 14

N-(1-ethoxycarbonyl-1-dimethylamino-methyl)-chlorotetracycline 1.5 Milliliters of dimethylamine and 2.2 g of ethyl semiacetal of ethyl glyoxylate were successively dissolved in 75 ml of dimethylformamide and, after 1 hour, 4.6 g of 7-chlorotetracycline base were added. The mixture was then stirred for 4 hours at room temperature under nitrogen, concentrated by evaporation at greatly reduced pressure and at a maximum temperature of 50°C, and the oily residue was dissolved in dichloromethane. The reaction product was precipitated by adding the solution dropwise to diisopropyl ether, the precipitate was filtered and dried at room temperature under greatly reduced pressure.

Yield: 4.5 g; decomposition point: 137°C, $C_{28}H_{34}ClN_3O_{10}$ (608.1), calculated: C 55.3 H 5.6 N 6.9, found: C 55.3 H 6.3 N 7.2.

In the $H^1$-NMR (in $CDCl_3$), the compound showed inter alia a characteristical absorption at 5.4 ppm for

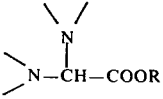

Examples 15 – 18 were carried out in analogous manner.

EXAMPLE 15

N-(1-n-butoxycarbonyl-1-dimethylamino-methyl)-chlorotetracycline

Melting point: 100°C, $C_{30}H_{38}ClN_3O_{10}$ (636.1), calculated: C 56.6 H 6.0 Cl 5.6 N 6.6, found: C 55.5 H 6.3 Cl 5.8 N 6.7.

EXAMPLE 16

N-(1-ethoxycarbonyl-1-pyrrolidyl(1)-methyl)-chlorotetracycline

Melting point: 122°–127°C; $R_f$-value = 0.81, $C_{30}H_{38}ClN_3O_{10}$ (634.1), calculated: C 56.8 H 5.7 Cl 5.6 N 6.6, found: C 56.8 H 6.2 Cl 5.7 N 7.3.

EXAMPLE 17

N-(1-n-butoxycarbonyl-1-pyrrolidyl(1)-methyl)-chlorotetracycline

Melting point: 95°C; $R_f$-value = 0.75, $C_{32}H_{40}ClN_3O_{10}$ (662.2), calculated: C 58.0 H 6.1 Cl 5.4 N 6.4, found: C 58.5 H 6.0 Cl 5.4 N 6.3.

EXAMPLE 18

N-(1-ethoxycarbonyl-1-piperidyl(1)-methyl)-chlorotetracycline

Melting point: 177°C $C_{31}H_{38}ClN_3O_{10} \cdot H_2O$ (666.1) calculated: C 55.9 H 6.0 N 6.3 found: C 56.1 H 6.6 N 6.9.

EXAMPLE 19

N-(1-ethoxycarbonyl-1-dimethylamino-methyl)-7-chloro-6-desmethyl-tetracycline

1 Milliliter of liquified dimethylamine and 5 g of ethyl semiacetal of ethyl glyoxylate were dissolved successively in 100 ml of dimethylformamide, and after 1 hour 4.7 g of 7chloro-6-desmethyl-tetracycline base were added. The mixture was then stirred for 3 hours at room temperature under nitrogen and then concentrated by evaporation under greatly reduced pressure at a maximum temperature of 50°C; the residue was dissolved in about 30 ml of ethyl acetate, and N-(1-ethoxycarbonyl-1-dimethylamino-methyl)-7-chloro-6-desmethyl-tetracycline was precipitated with diisopropyl ether.

Yield: 4.8 grams; decomposition point: 109°–114°C. In the H¹-NMR (in CDCl₃), the compound showed inter alia a characteristical absorption at 5.4 ppm for

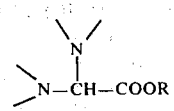

The Examples 20 – 23 were carried out in an analogous manner.

EXAMPLE 20

N-(1-n-butoxycarbonyl-1-dimethylamino-methyl)-7-chloro-6-desmethyl-tetracycline

Melting point: 100°–105°C; $R_f$-value = 0.68, $C_{29}H_{36}ClN_3O_{10}$ (622.1), calculated: C 56.1 H 5.8 Cl 5.7 N 6.8, found: C 55.5 H 6.3 Cl 5.8 N 6.1.

EXAMPLE 21

N-(1-ethoxycarbonyl-1-pyrrolidyl(1)-methyl)-7-chloro-6-desmethyl-tetracycline

Melting point: 134°–137°C, $C_{29}H_{34}ClN_3O_{10}$ (620.1), calculated: C 56.2 H 5.5 Cl 5.7 N 6.8, found: C 55.4 H 6.1 Cl 5.4 N 6.5.

EXAMPLE 22

N-(1-n-butoxycarbonyl-1-pyrrolidyl(1)-methyl)-7-chloro-6-desmethyl-tetracycline

Melting point: 102°C; $R_f$-value = 0.76, $C_{31}H_{36}ClN_3O_{10}$ (648.1), calculated: C 57.4 H 5.0 Cl 5.5 N 6.5, found: C 57.8 H 6.3 Cl 5.1 N 6.6.

EXAMPLE 23

N-(1-ethoxycarbonyl-1-piperidyl(1)-methyl)-7-chloro-6-desmethyl-tetracycline

Melting point: 117°–119°C, $C_{30}H_{36}ClN_3O_{10}$ (652.1), calculated: C 55.1 H 5.8 Cl 5.4 N 6.4, found: C 54.9 H 5.8 Cl 5.8 N 5.7.

We claim:

1. A 2-carboxamido-substituted tetracycline of the general formula I

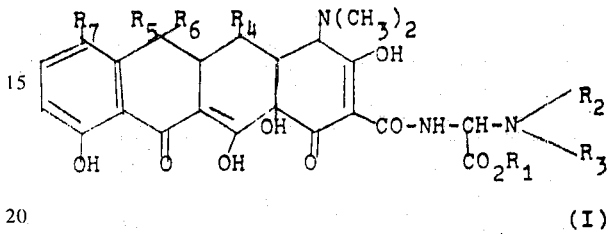

(I)

in which $R_1$ is lower, optionally branched alkyl, $R_2$ and $R_3$ may be identical or different and each is hydrogen, optionally branched alkyl of 1 to 6 carbon atoms which may carry one or more identical or different substituents selected from the group consisting of hydroxy, lower dialkylamino, lower dialkylcarbamoyl, lower alkoxycarbonyl, phenyl, a heterocyclic group, especially a 5- or 6-membered ring which may include oxygen and/or nitrogen, and carboxyl, in this latter case the alkyl moiety may also carry amino; or cycloalkyl of 5 to 7 carbon atoms, and in which $R_2$ and $R_3$ may also be closed to form a saturated or unsaturated 5- or 6-membered ring which may include nitrogen or oxygen and may carry one or more substituents selected from the group consisting of lower alkyl, lower hydroxyalkyl, lower carboxyalkyl, hydroxyl or carboxyl, $R_4$ and $R_5$ may be identical or different and each is hydrogen or hydroxy, $R_6$ is hydrogen or methyl, $R_5$ and $R_6$ together are methylene, and $R_7$ is hydrogen, chlorine, bromine, dimethylamino or diethylamino.

2. A compound of claim 1 which is N-(1-ethoxycarbonyl-1-dimethylamino-methyl)-tetracycline.
3. A compound of claim 1 which is N-(1-n-butoxycarbonyl-1-dimethylamino-methyl)-tetracycline.
4. A compound of claim 1 which is N-(1-ethoxycarbonyl-1-pyrrolidyl(1)-methyl)-tetracycline.
5. A compound of claim 1 which is N-(1-n-butoxycarbonyl-1-pyrrolidyl(1)-methyl)-tetracycline.
6. A compound of claim 1 which is N-(1-ethoxycarbonyl-1-piperidyl(1)-methyl)-tetracycline.
7. A compound of claim 1 which is N-(1-n-butoxycarbonyl-1-piperidyl(1)-methyl)-tetracycline.
8. A compound of claim 1 which is N-(1-ethoxycarbonyl-1-morpholinyl(4)-methyl)-tetracycline.
9. A compound of claim 1 which is N-[1-ethoxycarbonyl-1-(4-β-hydroxyethylpiperazyl(1)-methyl]-tetracycline.
10. A compound of claim 1 which is N-(1-ethoxycarbonyl-1-dimethylamino-methyl)-oxytetracycline.
11. A compound of claim 1 which is N-(1-n-butoxycarbonyl-1-dimethylamino-methyl)-oxytetracycline.
12. A compound of claim 1 which is N-(1-ethoxycarbonyl-1-pyrrolidyl(1)-methyl)-oxytetracycline.
13. A compound of claim 1 which is N-(1-n-butoxycarbonyl-1-pyrrolidyl(1)-methyl)-oxytetracycline.
14. A compound of claim 1 which is N-(1-ethoxycarbonyl-1-piperidyl(1)-methyl)-oxytetracycline.

15. A compound of claim 1 which is N-(1-ethoxycarbonyl-1-dimethylamino-methyl)-chlorotetracycline.

16. A compound of claim 1 which is N-(1-n-butoxycarbonyl-1-dimethylamino-methyl)-chlorotetracycline.

17. A compound of claim 1 which is N-(1-ethoxycarbonyl-1-pyrrolidyl(1)-methyl)-chlorotetracycline.

18. A compound of claim 1 which is N-(1-n-butoxycarbonyl-1-pyrrolidyl(1)-methyl)-chlorotetracycline.

19. A compound of claim 1 which is N-(1-ethoxycarbonyl-1-piperidyl(1)-methyl)-chlorotetracycline.

20. A compound of claim 1 which is N-(1-ethoxycarbonyl-1-dimethylamino-methyl)-7-chloro-6-desmethyl-tetracycline.

21. A compound of claim 1 which is N-(1-n-butoxycarbonyl-1-dimethylamino-methyl)-7-chloro-6-desmethyl-tetracycline.

22. A compound of claim 1 which is N-(1-ethoxycarbonyl-1-pyrrolidyl(1)-methyl)-7-chloro-6-desmethyl-tetracycline.

23. A compound of claim 1 which is N-(1-n-butoxycarbonyl-1-pyrrolidyl(1)-methyl)-7-chloro-6-desmethyl-tetracycline.

24. A compound of claim 1 which is N-(1-ethoxycarbonyl-1-piperidyl(1)-methyl)-7-chloro-6-desmethyl-tetracycline.

25. A pharmaceutical composition having antibacterial activity which comprises an effective amount of a compound of formula I as the active substance.

* * * * *